US012723074B2

(12) United States Patent
Okano et al.

(10) Patent No.: US 12,723,074 B2

(45) Date of Patent: Sep. 1, 2026

(54) MEDICAMENT FOR TREATMENT AND/OR PREVENTION OF CANCER

(71) Applicant: TORAY INDUSTRIES, INC., Tokyo (JP)

(72) Inventors: Fumiyoshi Okano, Kamakura (JP); Daisuke Akazawa, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 653 days.

Patent file contains an affidavit/declaration under 37 CFR 1.130(b).

(21) Appl. No.: 17/910,538

(22) PCT Filed: Mar. 11, 2021

(86) PCT No.: PCT/JP2021/009798

§ 371 (c)(1),
(2) Date: Sep. 9, 2022

(87) PCT Pub. No.: WO2021/182573

PCT Pub. Date: Sep. 16, 2021

(65) Prior Publication Data

US 2023/0129035 A1 Apr. 27, 2023

(30) Foreign Application Priority Data

Mar. 12, 2020 (JP) ................................ 2020-043021

(51) Int. Cl.

| | |
|---|---|
| ***C07K 16/28*** | (2006.01) |
| ***A61K 31/337*** | (2006.01) |
| ***A61P 35/00*** | (2006.01) |
| ***C07K 16/22*** | (2006.01) |

(52) U.S. Cl.

CPC ............ *C07K 16/28* (2013.01); *A61K 31/337* (2013.01); *A61P 35/00* (2018.01); *C07K 16/22* (2013.01); *C07K 16/2863* (2013.01)

(58) Field of Classification Search

CPC ........ C07K 16/28; A61P 35/00; A61K 31/337

See application file for complete search history.

(56) References Cited

U.S. PATENT DOCUMENTS

| | | | |
|---|---|---|---|
| 5,595,756 | A | 1/1997 | Bally et al. |
| 8,709,418 | B2 | 4/2014 | Okano et al. |
| 8,828,398 | B2 | 9/2014 | Kobayashi et al. |
| 8,911,740 | B2 | 12/2014 | Saito et al. |
| 8,937,160 | B2 | 1/2015 | Kobayashi et al. |
| 9,115,200 | B2 | 8/2015 | Okano et al. |
| 9,175,074 | B2 | 11/2015 | Okano et al. |
| 9,180,187 | B2 | 11/2015 | Ido et al. |
| 9,180,188 | B2 | 11/2015 | Kobayashi et al. |
| 9,181,334 | B2 | 11/2015 | Kobayashi et al. |
| 9,181,348 | B2 | 11/2015 | Kobayashi et al. |
| 9,260,513 | B2 | 2/2016 | Kobayashi et al. |
| 9,266,958 | B2 | 2/2016 | Kobayashi et al. |
| 9,273,128 | B2 | 3/2016 | Okano et al. |
| 9,273,130 | B2 | 3/2016 | Kobayashi et al. |
| 9,412,192 | B2 | 8/2016 | Mandel et al. |
| 9,416,192 | B2 | 8/2016 | Okano et al. |
| 9,416,193 | B2 | 8/2016 | Saito et al. |
| 9,428,581 | B2 | 8/2016 | Saito et al. |
| 9,473,993 | B2 | 10/2016 | Sachs et al. |
| 9,573,993 | B2 | 2/2017 | Okano et al. |
| 9,862,774 | B2 | 1/2018 | Okano et al. |
| 9,982,059 | B2 | 5/2018 | Okano et al. |
| 10,946,093 | B2 | 3/2021 | Junttila |
| 12,274,745 | B2 | 4/2025 | Okano et al. |
| 2005/0019845 | A1 | 1/2005 | Harkins et al. |
| 2011/0256144 | A1 | 10/2011 | Okano et al. |
| 2012/0294860 | A1 | 11/2012 | Ido et al. |
| 2012/0301471 | A1 | 11/2012 | Kobayashi et al. |
| 2012/0301476 | A1* | 11/2012 | Okano .................... A61P 35/02 424/139.1 |
| 2012/0321641 | A1 | 12/2012 | Okano et al. |
| 2013/0045210 | A1 | 2/2013 | Kobayashi et al. |
| 2013/0071398 | A1 | 3/2013 | Saito et al. |
| 2014/0154261 | A1 | 6/2014 | Okano et al. |
| 2014/0178373 | A1 | 6/2014 | Kobayashi et al. |
| 2014/0186359 | A1 | 7/2014 | Okano et al. |

(Continued)

FOREIGN PATENT DOCUMENTS

| | | | |
|---|---|---|---|
| EP | 2 322 221 | A1 | 5/2011 |
| EP | 2 324 842 | A1 | 5/2011 |

(Continued)

OTHER PUBLICATIONS

Chan et al., Annals of Oncology. vol. 21: 2305-2315. (Year: 2010).*

"A Study of TRK-950 in Combinations With Anti-Cancer Treatment Regimens in Patients With Advanced Solid Tumors," ClinicalTrials.gov, NCT03872947, Mar. 13, 2019, pp. 1-10.

"A Study of TRK-950 in Combinations With Anti-Cancer Treatment Regimens in Patients With Advanced Solid Tumors," ClinicalTrials.gov, NCT03872947, Unique Protocol ID 950P1V02, Aug. 28, 2019, 12 pages total.

Extended European Search Report for European Application No. 21767020.7, dated Apr. 8, 2024.

Extended European Search Report for European Application No. 21768178.2, dated Apr. 9, 2024.

Extended European Search Report for European Application No. 21768433.1, dated Feb. 28, 2024.

(Continued)

*Primary Examiner* — Sue X Liu

(74) *Attorney, Agent, or Firm* — Birch, Stewart, Kolasch & Birch, LLP

(57) ABSTRACT

An object of the preset invention is to provide a medicament for treatment and/or prevention of cancer. The present invention relates to a medicament for treatment and/or prevention of cancer in a cancer patient with a previous history of another cancer treatment, comprising an antibody or a fragment thereof haying an immunological reactivity with CAPRIN-1 protein, and an angiogenesis inhibitor or an angiogenesis inhibitor and a taxane-based drug together or separately in combination.

12 Claims, No Drawings

Specification includes a Sequence Listing.

(56) References Cited

U.S. PATENT DOCUMENTS

2014/0193434 A1 7/2014 Kobayashi et al.
2014/0199311 A1 7/2014 Kobayashi et al.
2014/0271634 A1 9/2014 Silwkowski et al.
2015/0004171 A1 1/2015 Kobayashi et al.
2015/0044221 A1 2/2015 Kobayashi et al.
2015/0050283 A1 2/2015 Okano et al.
2015/0299314 A1 10/2015 Saito et al.
2016/0297889 A1* 10/2016 Okano .................... A61P 35/00
2016/0354499 A1 12/2016 Ghanbari et al.
2017/0002090 A1 1/2017 Wang et al.
2017/0095571 A1 4/2017 Ponte et al.
2018/0000865 A1 1/2018 Weissman et al.
2018/0094322 A1 4/2018 Dalerba et al.
2018/0169230 A1 6/2018 Adams et al.
2018/0312603 A1 11/2018 Okano et al.
2018/0362443 A1 12/2018 Lavallee et al.
2020/0054762 A1 2/2020 Okano et al.
2021/0121562 A1 4/2021 Okano et al.
2022/0072167 A1 3/2022 Ludwig et al.
2023/0129035 A1 4/2023 Okano et al.
2023/0139178 A1 5/2023 Okano
2023/0140155 A1 5/2023 Okano
2023/0159635 A1 5/2023 Okano
2023/0165957 A1 6/2023 Okano et al.
2025/0228937 A1 7/2025 Okano et al.

FOREIGN PATENT DOCUMENTS

EP 2 532 367 A1 12/2012
EP 2 301 528 B1 4/2013
EP 2 818 481 A1 12/2014
EP 2 818 482 A1 12/2014
EP 2 832 365 A1 2/2015
EP 2 832 366 A1 2/2015
EP 2 818 481 B1 8/2019
EP 3 777 888 A1 2/2021
EP 4 119 156 A1 1/2023
EP 4 119 158 A1 1/2023
JP 2005-512961 A 5/2005
JP 2007-527403 A 9/2007
JP 2015-502958 A 1/2015
JP 2015-127308 A 7/2015
JP 2017-510548 A 4/2017
JP 2017-535548 A 11/2017
JP 2018-502892 A 2/2018
JP 2018-516263 A 6/2018
JP 2018-518476 A 7/2018
JP 2018-527383 A 9/2018
JP 2019-504029 A 2/2019
JP 2019-527698 A 10/2019
JP 2022-516170 A 2/2022
KR 10-2014-0130670 A 11/2014
WO WO 03/024442 A2 3/2003
WO WO 2009/142810 A2 11/2009
WO WO 2010/016526 A1 2/2010
WO WO 2010/080345 A1 7/2010
WO WO 2011/096517 A1 8/2011
WO WO 2011/096519 A1 8/2011
WO WO 2011/096528 A1 8/2011
WO WO 2011/096533 A1 8/2011
WO WO 2011/096534 A1 8/2011
WO WO 2011/096535 A1 8/2011
WO WO 2013/018883 A1 2/2013
WO WO 2013/018889 A1 2/2013
WO WO 2013/018891 A1 2/2013
WO WO 2013/018892 A1 2/2013
WO WO 2013/018894 A1 2/2013
WO WO 2013/086260 A2 6/2013
WO WO 2013/125630 A1 8/2013
WO WO 2013/125636 A1 8/2013
WO WO 2013/125654 A1 8/2013
WO WO 2013/147176 A1 10/2013
WO WO 2014/195852 A1 12/2014
WO WO 2015/020212 A1 2/2015
WO WO 2015/112749 A2 7/2015
WO WO 2016/004875 A1 1/2016
WO WO 2016/077227 A2 5/2016
WO WO 2016/193955 A1 12/2016
WO WO 2017/031367 A1 2/2017
WO WO 2017/112838 A1 6/2017
WO WO 2018/023197 A1 2/2018
WO WO 2018/079740 A1 5/2018
WO WO 2018/213302 A1 11/2018
WO WO 2018/234879 A1 12/2018
WO WO 2019/155448 A1 8/2019
WO WO 2019/189780 A1 10/2019
WO WO 2020/000704 A1 1/2020
WO WO 2021/154761 A1 8/2021
WO WO 2021/182570 A1 9/2021
WO WO 2021/182571 A1 9/2021
WO WO 2021/182572 A1 9/2021
WO WO 2021/182573 A1 9/2021
WO WO 2021/182574 A1 9/2021
WO WO 2022/270523 A1 12/2022
WO WO 2022/270524 A1 12/2022
WO WO 2023/008459 A1 2/2023
WO WO 2023/008461 A1 2/2023
WO WO 2023/008462 A1 2/2023
WO WO 2023/033129 A1 3/2023
WO WO 2025/058000 A1 3/2025

OTHER PUBLICATIONS

Hanna et al., "A Ph-Ib study of TRK-950 combined with anti-cancer treatment regimens in patients with advanced solid tumors," European Journal of Cancer, 34th EORTC-NCI-AACR Symposium, vol. 174S1, Oct. 26, 2022, pp. S32-S33.
"A Study of TRK-950 in Combinations With Anti-Cancer Treatment Regimens in Patients With Advanced Solid Tumors", ClinicalTrials.gov, [online], Mar. 13, 2019, total 12 pages.
"A Study of TRK-950 in Combinations With Anti-Cancer Treatment Regimens in Patients With Advanced Solid Tumors", ClinicalTrials.gov, Mar. 13, 2019, total 12 pages. https://Clinicaltrials.gov/ct2/show/NCT03872947?term=TRK-950&draw=2&rank=2.
International Search Report, issued in PCT/JP2021/009798, PCT/ISA/210, dated Apr. 20, 2021.
Kadowaki et al., "Multicenter phase I/II study of nivolumab combined with paclitaxel plus ramucirumab as the second-line treatment in patients with advanced gastric cancer", the ESMO World Congress on Gastrointestinal Cancer 2019, Abstract #SO-001, total 1 page.
Wilke et al., "Ramucirumab plus paclitaxel versus placebo plus paclitaxel in patients with previously treated advanced gastric or gastro-oesophageal junction adenocarcinoma (RAINBOW): a double-blind, randomised phase 3 trial", Lancet Oncology, 2014, vol. 15, No. 11, p. 1224-1235.
Written Opinion of the International Searching Authority, issued in PCT/JP2021/009798, PCT/ISA/237, dated Apr. 20, 2021.
International Search Report for International Application No. PCT/JP2023/024125, dated Sep. 12, 2023.
Australian Office Action for Australian Application No. 2019242520, dated Feb. 17, 2025.
"Imiquimod and Pembrolizumab in Treating Patients With Stage IIIB-IV Melanoma," ClinicalTrials.gov, Sep. 8, 2017, 9 pages total.
Aghajanian et al., "OCEANS: A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer," Journal of Clinical Oncology, vol. 30, No. 17, 2012, pp. 2039-2045.
Alt et al., "Enfortumab Vedotin in urothelial cancer," Therapeutic Advances in Urology, vol. 12, 2020; pp. 1-10.
Anonymous, "History of Changes for Study: NCT03276832, Imiquimod and Pembrolizumab in Treating Patients With Stage IIIB-IV Melanoma", ClinicalTrials.gov, Dec. 20, 2017, pp. 1-5.
Auerbach et al., "Angiogenesis assays: Problems and pitfalls," Cancer and Metastasis Reviews, vol. 19, 2000, pp. 167-172.
Barth et al., "Prognostic Factors in 1,521 Melanoma Patients With Distant Metastases," Journal of the American College of Surgeons, vol. 181, No. 3, 1995, pp. 193-201.

(56) References Cited

OTHER PUBLICATIONS

Berman et al., "Novel Dermatologic Uses of the Immune Response Modifier Imiquimod 5% Cream", Skin Therapy Letter, vol. 7, No. 9, 2002, pp. 1-6.
Brown et al., "Tolerance to Single, but Not Multiple, Amino Acid Replacements in Antibody VH CDR2—A Means of Minimizing B Cell Wastage from Somatic Hypermutation?," Journal of Immunology, vol. 156, 1996, pp. 3285-3291.
Campione et al., "Lack of efficacy of imiquimod in patients with basal cell carcinoma previously treated with rituximab for B cell lymphoma: two case reports," Journal of Medical Case Reports, vol. 10, No. 57, 2016, pp. 1-3.
Christiansen et al., "Biological impediments to monoclonal antibody-based cancer immunotherapy," Molecular Cancer Therapeutics, vol. 3, No. 11, 2004, pp. 1493-1501.
Ciardiello et al., "Antitumor Activity of Sequential Treatment with Topotecan and Anti-Epidermal Growth Factor Receptor Monoclonal Antibody C225," Clinical Cancer Research, vol. 5, No. 4, 1999, pp. 909-916.
Cohen et al., "Treatment of Extramammary Paget Disease with Topical Imiquimod Cream: Case Report and Literature Review," Southern Medical Journal, vol. 99, pp. 396-402. 2006.
Colombo et al., "Treatment of recurrent ovarian cancer relapsing 6-12 months post platinum-based chemotherapy," Critical Reviews in Oncology/Hematology, vol. 64, 2007, pp. 129-138.
Corraliza-Gorjón et al., "New Strategies Using Antibody Combinations to Increase Cancer Treatment Effectiveness," Frontiers in Immunology, vol. 8, 2017, pp. 1-31.
Douillard et al., "Irinotecan combined with fluorouracil compared with fluorouracil alone as first-line treatment for metastatic colorectal cancer: a multicentre randomised trial," The Lancet, vol. 355, 2000, pp. 1041-1047.
Dummer et al., "Imiquimod in basal cell carcinoma: how does it work?," British Journal of Dermatology, vol. 149; Suppl. 66, 2003, pp. 57-58.
Extended European Search Report for European Application No. 19774904.7, dated Oct. 29, 2021.
Ferrandina et al., "Phase III Trial of Gemcitabine Compared With Pegylated Liposomal Doxorubicin in Progressive or Recurrent Ovarian Cancer," Journal of Clinical Oncology, vol. 26, No. 6, 2008, pp. 890-896.
Gordon et al., "Recurrent Epithelial Ovarian Carcinoma: A Randomized Phase III Study of Pegylated Liposomal Doxorubicin Versus Topotecan," Journal of Clinical Oncology, vol. 19, No. 14, 2001, pp. 3312-3322.
Greenshields et al., "Imiquimod induces reactive oxygen species- and caspase-independent cell cycle arrest and apoptosis in MDA-MB-468 breast cancer cells," Molecular Cancer Therapeutics, vol. 8, Issue 12, supplement, abstract C88, 2009, 2 pages total.
Gura, "Systems for Identifying New Drugs Are Often Faulty," Science, vol. 278, 1997, pp. 1041-1042.
Hammond et al., "Pharmacologic resistance in colorectal cancer: a review," Therapeutic Advances in Medical Oncology, vol. 8, No. 1, 2016, pp. 57-84.
Henriques et al., "Imiquimod in the Treatment of Breast Cancer Skin Metastasis," Journal of Clinical Oncology, vol. 32, No. 8, 2014, pp. e22-e25.
Hogenesch et al., "Challenges in pre-clinical testing of anti-cancer drugs in cell culture and in animal models," Journal of Controlled Release, vol. 164, No. 2, 2012, pp. 183-186.
Hou et al., "Tunicamycin Potentiates Cisplatin Anticancer Efficacy through the DPAGT1/Akt/ABCG2 Pathway in Mouse Xenograft Models of Human Hepatocellular Carcinoma," Molecular Cancer Therapeutics, vol. 12, No. 12, 2013, pp. 2874-2884.
Imai, "HDAC inhibitors for treatment of multiple myeloma," Hematology, vol. 78, No. 1, 2019, pp. 18-24, with a partial English translation.
International Search Report for International Application No. PCT/JP2019/014044, dated May 21, 2019.
International Search Report for International Application No. PCT/JP2021/009795, dated Apr. 20, 2021.
International Search Report for International Application No. PCT/JP2021/009796, dated Apr. 20, 2021.
International Search Report for International Application No. PCT/JP2021/009797, dated Apr. 20, 2021.
International Search Report for International Application No. PCT/JP2021/009799, dated Apr. 20, 2021.
International Search Report for International Application No. PCT/JP2022/024812, dated Sep. 13, 2022.
International Search Report for International Application No. PCT/JP2022/024814, dated Sep. 13, 2022.
International Search Report for International Application No. PCT/JP2022/028871, dated Sep. 27, 2022.
International Search Report for International Application No. PCT/JP2022/028877, dated Oct. 18, 2022.
International Search Report for International Application No. PCT/JP2022/028878, dated Oct. 18, 2022.
Ishida et al., "Regimen Selection for First-line FOLFIRI and FOLFOX Based on UGT1A1 Genotype and Physical Background is Feasible in Japanese Patients with Advanced Colorectal Cancer," Japanese Journal of Clinical Oncology, vol. 41, No. 5, 2011, pp. 617-623.
Ishii, "MEK/RAF, Big-name cancer molecular targets that have finally came—R&D of MAPK pathway inhibitors," Folia Pharmacologica Japonica, vol. 141, 2013, pp. 15-21, with an English translation.
Jain et al., "Current ADC Linker Chemistry," Pharmaceutical Research, vol. 32, 2015, pp. 3526-3540.
Jain, "Barriers to Drug Delivery in Solid Tumors," Scientific American, 1994, pp. 58-65.
Joseph et al., "Treatment of in-transit and metastatic melanoma in two patients treated with ipilimumab and topical imiquimod," Melanoma Research, vol. 26, No. 4, 2016, pp. 409-412.
Kitchen et al., "Comment on The efficacy and toxicity of gemcitabine, carboplatin and bevacizumab in metastatic breast cancer," British Journal of Cancer, vol. 109, 2013, pp. 526-528.
Komiyama et al., "Japan Society of Gynecologic Oncology guidelines 2015 for the treatment of ovarian cancer including primary peritoneal cancer and fallopian tube cancer," International Journal of Clinical Oncology, vol. 21, 2016, pp. 435-446.
Kussie et al., "A Single Engineered Amino Acid Substitution Changes Antibody Fine Specificity," Journal of Immunology, 1994, pp. 146-152.
Larkin et al., "Five-Year Survival with Combined Nivolumab and Ipilimumuab in Advanced Melanoma," New England Journal of Medicine, vol. 381, 2019, pp. 1535-1546.
Lee et al., "Targeting MAPK Signaling in Cancer: Mechanisms of Drug Resistance and Sensitivity," International Journal of Molecular Sciences, vol. 21, 2020, pp. 1-29.
Li et al., "Glycosylation and stabilization of programmed death ligand-1 suppresses T-cell activity," Nature Communications, vol. 7, 2016, pp. 1-11.
Li et al., "HDACs and HDAC Inhibitors in Cancer Development and Therapy," Cold Spring Harbor Perspectives in Medicine, vol. 6, 2016, pp. 1-34.
Lito et al., "Tumor adaptation and resistance to RAF inhibitors," Nature Medicine, vol. 19, No. 11, 2013, pp. 1401-1409.
Liu et al., "BRAF/MEK inhibitors promote CD47 expression that is reversible by ERK inhibition in melanoma," Oncotarget, vol. 8, No. 41, 2017, pp. 69477-69492.
Mereiter et al., "Glycosylation in the Era of Cancer-Targeted Therapy: Where Are We Heading?," Cancer Cell, vol. 36, 2019, pp. 6-16.
Metzger-Filho et al., "Dissecting the Heterogeneity of Triple-Negative Breast Cancer," Journal of Clinical Oncology, vol. 30, 2012, pp. 1879-1887.
Mitachi et al., "DPAGT1 Inhibitors of Capuramycin Analogues and Their Antimigratory Activities of Solid Tumors," Journal of Medicinal Chemistry, vol. 63, 2020, pp. 10855-10878.
Omura et al., "Phase III Trial of Paclitaxel at Two Dose Levels, the Higher Dose Accompanied by Filgrastim at Two Dose Levels in

(56) References Cited

OTHER PUBLICATIONS

Platinum-Pretreated Epithelial Ovarian Cancer: An Intergroup Study," Journal of Clinical Oncology, vol. 21, No. 15, 2003, pp. 2843-2848.
Park et al., "A short guide to histone deacetylases including recent progress on class II enzymes," Experimental & Molecular Medicine, vol. 52, 2020, pp. 204-212.
Peyssonnaux et al., "The Raf/MEK/ERK pathway: new concepts of activation," Biology of the Cell, vol. 93, 2001, pp. 53-62.
Peyton et al., "Downstaging and Survival Outcomes Associated With Neoadjuvant Chemotherapy Regimens Among Patients Treated With Cystectomy for Muscle-Invasive Bladder Cancer," JAMA Oncology, vol. 4, No. 11, 2018, pp. 1535-1542.
Pfisterer et al., "Bevacizumab and platinum-based combinations for recurrent ovarian cancer: a randomised, open-label, phase 3 trial," Lancet Oncology, vol. 21, 2020, pp. 699-709.
Pujade-Lauraine et al., "Bevacizumab Combined With Chemotherapy for Platinum-Resistant Recurrent Ovarian Cancer: The AURELIA Open-Label Randomized Phase III Trial," Journal of Clinical Oncology, vol. 32, No. 13, 2014, pp. 1302-1308.
Rose et al., "Prolonged Oral Etoposide as Second-Line Therapy for Platinum-Resistant and Platinum-Sensitive Ovarian Carcinoma: A Gynecologic Oncology Group Study," Journal of Clinical Oncology, vol. 16, No. 2, 1998, pp. 405-410.
Rowinsky et al., "Review of Phase I Clinical Studies With Topotecan," Seminars in Oncology, vol. 24, No. 6, 1997, pp. S20-3-S20-10.
Salazar et al., "Topical Imiquimod Plus Nab-paclitaxel for Breast Cancer Cutaneous Metastases—A Phase 2 Clinical Trial," JAMA Oncology, vol. 3, No. 7, 2017, pp. 969-973.
Shroff et al., "Gemcitabine, Cisplatin, and nab-Paclitaxel for the Treatment of Advanced Biliary Tract Cancers—A Phase 2 Clinical Trial," JAMA Oncology, vol. 5, No. 6, 2019, pp. 824-830.
Siegel et al., "Colorectal Cancer Statistics, 2014," CA: A Cancer Journal for Clinicians, vol. 64, 2014, pp. 104-117.
Sporn et al., "Chemoprevention of cancer," Carcinogenesis, vol. 21, No. 3, 2000, pp. 525-530.
Study NCT03276832. National Cancer Institute (NCI): Imiquimod and Pembrolizumab in Treating Patients With Stage IIIB-IV Melanoma—ClinicalTrials.gov, Dec. 20, 2017 (v2), URL: https://clinicaltrials.gov/ct2/history/NCT03276832?V_2=View#StudyPageTop.
Sun et al., "Targeting glycosylated PD-1 induces potent anti-tumor immunity," Cancer Research, vol. 80, No. 11, 2020, pp. 2298-2310.
Suraweera et al., "Combination Therapy With Histone Deacetylase Inhibitors (HDACi) for the Treatment of Cancer: Achieving the Full Therapeutic Potential of HDACi," Frontiers in Oncology, vol. 8, 2018, pp. 1-15.
Thomas et al., "Antibody-drug conjugates for cancer therapy," Lancet Oncology, vol. 17, No. 6, 2016, pp. e254-e262.
Topp et al., "Antibody transport in cultured tumor cell layers," Journal of Controlled Release, vol. 53, 1998, pp. 15-23.
Vajdos et al., "Comprehensive Functional Maps of the Antigen-binding Site of an Anti-ErbB2 Antibody Obtained with Shotgun Scanning Mutagenesis," Journal of Molecular Biology, vol. 320, 2002, pp. 415-428.
Wojtowicz et al., "Inhibition of protein glycosylation reverses the MDR phenotype of cancer cell lines," Biomedicine & Pharmacotherapy, vol. 74, 2015, pp. 49-56.
Wu et al., "Tunicamycin specifically aggravates ER stress and overcomes chemoresistance in multidrug-resistant gastric cancer cells by inhibiting N-glycosylation," Journal of Experimental & Clinical Cancer Research, vol. 37, No. 272, 2018, pp. 1-12.
Yuan et al., "The MAPK and AMPK signalings: interplay and implication in targeted cancer therapy," Journal of Hematology & Oncology, vol. 13, No. 113, 2020, pp. 1-19.
Zechmeister, "Progress in the Chemistry of Organic Natural Products," Springer Chemistry, 1997, 86 pages total.
Amodio et al., "EGFR Blockade Reverts Resistance to KRASG12C Inhibition in Colorectal Cancer," Cancer Discovery, vol. 10, Aug. 2020, pp. 1129-1139.
Du et al., "Inhibition of ERAD synergizes with FTS to eradicate pancreatic cancer cells," BMC Cancer, vol. 21, No. 237, 2021, pp. 1-13.
Extended European Search Report for European Application No. 22849523.0, dated Oct. 15, 2025.
Golas et al., "SKI-606, a Src/Abl Inhibitor with In vivo Activity in Colon Tumor Xenograft Models," Cancer Research, vol. 65, No. 12, Jun. 15, 2005, pp. 5358-5364.
Hochster et al., "Phase II study of selumetinib (AZD6244, ARRY-142886) plus irinotecan as second-line therapy in patients with K-RAS mutated colorectal cancer," Cancer Chemother Pharmacol, vol. 75, 2015, pp. 17-23.
Jain et al., "Inotuzumab ozogamicin with bosutinib for relapsed or refractory Philadelphia chromosome positive acute lymphoblastic leukemia or lymphoid blast phase of chronic myeloid leukemia," Am J Hematol., vol. 96, 2021, pp. 1000-1007.
Kim et al., "Targeting KRAS(G12C): From Inhibitory Mechanism to Modulation of Antitumor Effects in Patients," Cell, vol. 183, Nov. 12, 2020, pp. 850-859.
Kunnimalaiyaan et al., "Neuroendocrine tumor cell growth inhibition by ZM336372 through alterations in multiple signaling pathways," Surgery, vol. 142, No. 6, Dec. 2007, pp. 959-964.
Liang et al., "SCH 66336 (Lonafarnib), a farnesyl transferase inhibitor, demonstrates enhanced antitumor efficacy in combination with the alkylating agent Temozolomide, Cisplatin, and Carboplatin," Proceedings of the American Association for Cancer Research, vol. 44, 2nd Edition, #807, Jul. 2003, p. 158.
Pal R et al., "Stem-like colorectal cancer cell lines show response to the ERK1/2 inhibitor, SCH772984, alone and in combination with neratinib," EMBASE, Accession No. EMB-619155942, Jul. 1, 2017, 4 pages total.
Sanz-Garcia et al., "BRAF mutant colorectal cancer: prognosis, treatment, and new perspectives," Annals of Oncology, vol. 28, Issue 11, 2017, pp. 2648-2657.
U.S. Office Action for U.S. Appl. No. 17/910,549, dated Nov. 13, 2025.
Wong et al., "Lonafarnib for cancer and progeria," Expert Opinion on Investigational Drugs, vol. 21, No. 7, 2012, pp. 1043-1055.
"A Study of TRK-950 in Combinations With Anti-Cancer Treatment Regimens in Patients With Advanced Solid Tumors," National Library of Medicine, ClinicalTrials.gov, NCT03872947, Version 1, Mar. 13, 2019, pp. 1-18.
Azmy et al., "Gemcitabine Plus Carboplatin in Patients with Advanced Hepatocellular Carcinoma: Results of a Phase II Study," ISRN Oncology, vol. 2012, Article ID 420931, 2012, pp. 1-5.
Eisenhauer et al., "A phase II study of gemcitabine, carboplatin and bevacizumab for the treatment of platinum-sensitive recurrent ovarian cancer," Gynecologic Oncology, vol. 134, 2014, pp. 262-266.
Pignata et al., "Treatment of recurrent ovarian cancer," Annals of Oncology, vol. 28 (Supplement 8), Nov. 2017, pp. viii51-viii56.
Suresh et al., "Gemcitabine and carboplatin in the treatment of metastatic cholangiocarcinoma and gallbladder cancer," Journal of Clinical Oncology, vol. 25, No. 18 Suppl, 2007, pp. 1-2, abstract provided only.
U.S. Office Action for U.S. Appl. No. 17/910,544, dated Sep. 17, 2025.
Lloyd et al., "Modelling the Human Immune Response: Performance of a $10^{11}$ Human Antibody Repertoire Against a Broad Panel of Therapeutically Relevant Antigens," Protein Engineering, Design and Selection, vol. 22, No. 3, Oct. 29, 2008, pp. 159-168.
U.S. Office Action for U.S. Appl. No. 17/910,532, dated Aug. 25, 2025.
Wikipedia, "List of Cancer Types," 2020, pp. 1-7.
"What is Cancer?", National Cancer Institute, 2020, pp. 1-8.
Extended European Search Report for European Application No. 22828440.2, dated May 27, 2025.
Okano et al., "Identification of Membrane-expressed CAPRIN-1 as a Novel and Universal Cancer Target, and Generation of a Therapeutic Anti-CAPRIN-1 Antibody TRK-950," Cancer Research Communications, vol. 3, No. 4, XP093277915, Apr. 2023, pp. 640-658.
U.S. Office Action for U.S. Appl. No. 17/910,544, dated Jun. 17, 2025.

(56) References Cited

OTHER PUBLICATIONS

Vanderbeeken et al., "Topoisomerase Inhibitors in Metastatic Breast Cancer: Overview of Current Practice and Future Development," Current Breast Cancer Reports, vol. 5, XP035340237, 2013, pp. 31-41.
Banerjee et al., "Benefits and Pitfalls of a Glycosylation Inhibitor Tunicamycin in the Therapeutic Implication of Cancers," Cells, vol. 13, No. 5, XP093285590, Feb. 25, 2024, pp. 1-16.
Esko et al., "Chapter 40—Natural and Synthetic Inhibitors of Glycosylation," Essentials of Glycobiology, XP093285359, Jan. 1, 1999, pp. 1-18.
Extended European Search Report for European Application No. 22849522.2, dated Jul. 14, 2025.
Han et al., "Tunicamycin enhances the antitumor activity of trastuzumab on breast cancer in vitro and in vivo," Oncotarget, vol. 6, No. 36, XP093285591, Oct. 12, 2015, pp. 38912-38925.
"A Study of TRK-950 in Combinations With Anti-Cancer Treatment Regimens in Patients With Advanced Solid Tumors," National Library of Medicine, NCT03872947, Aug. 3, 2025, 24 pages total.
Australian Office Action for Australian Application No. 2019242520, dated Jan. 16, 2026.
Korean Office Action for Korean Application No. 10-2022-7035177, dated Jan. 9, 2026.
Lipman et al., "Monoclonal Versus Polyclonal Antibodies: Distinguishing Characteristics, Applications, and Information Resources," ILAR Journal, vol. 46, No. 3, 2005, pp. 258-268.
Pfisterer et al., "Gemcitabine Plus Carboplatin Compared With Carboplatin in Patients With Platinum-Sensitive Recurrent Ovarian Cancer: An Intergroup Trial of the AGO-OVAR, the NCIC CTG, and the EORTC GCG," Journal of Clinical Oncology, vol. 24, No. 29, Oct. 10, 2006, pp. 4699-4707.
Ha et al., "Mycophenolic acid inhibits mesangial cell activation through p38 MAPK inhibition," Life Sciences, vol. 79, 2006, pp. 1561-1567.
Hatzivassiliou et al., "Mechanism of MEK inhibition determines efficacy in mutant KRAS-versus BRAF-driven cancers," Nature, vol. 501, 2013, pp. 1-5 (6 pages total).
Li et al., "MEK Inhibitor Augments Antitumor Activity of B7-H3-Redirected Bispecific Antibody," Frontiers in Oncology, vol. 10, Article 1527, Aug. 25, 2020, pp. 1-15.
Moreno et al., "Combined treatment with dabrafenib and trametinib with immune-stimulating antibodies for BRAF mutant melanoma," OncoImmunology, vol. 5, Issue 7, Jul. 2016, pp. e1052212-1-e1052212-8.
Partial Supplementary European Search Report for European Application No. 22828439.4, dated Jun. 20, 2025.
Partial Supplementary European Search Report for European Application No. 22849523.0, dated Jun. 20, 2025.
Toray Industries, "A Study of TRK-950 in Combinations With Anti-Cancer Treatment Regimens in Patients With Advanced Solid Tumors," ClinicalTrials.gov, NCT03872947, Mar. 27, 2020, pp. 1-19.
Xie et al., "Systemic treatment options for advanced biliary tract carcinoma," The Japanese Society of Gastroenterology, vol. 55, 2020, pp. 944-957.
Abdelaziz et al., "A purified and lyophilized Pseudomonas aeruginosa derived pyocyanin induces promising apoptotic and necrotic activities against MCF-7 human breast adenocarcinoma," Microbial Cell Factories, vol. 21, Article 262, 2022, pp. 1-16.
Aikawa et al., "Cell death induced by dorsomorphin in adult T-cell leukemia/lymphoma is AMPK-independent," The FEBS Journal, vol. 287, No. 18, 2020, pp. 4005-4015.
Duffy et al., "GSK3 Inhibitors Regulate MYCN mRNA Levels and Reduce Neuroblastoma Cell Viability through Multiple Mechanisms, Including p53 and Wnt Signaling," Molecular Cancer Therapeutics, vol. 13, No. 2, Feb. 2014, pp. 454-467.
English translation of the International Search Report for International Application No. PCT/JP2024/012990, dated Jun. 18, 2024.
Gong et al., "Caprin-1 is a novel microRNA-223 target for regulation the proliferation and invasion of human breast cancer cells," Biomedicine & Pharmacotherapy, vol. 67, No. 7, 2013, pp. 629-636.
He et al., "Baicalein and Ly294002 induces liver cancer cells apoptosis via regulating phosphatidyl inositol 3-kinase/Akt signaling pathway," Journal of Cancer Research and Therapeutics, vol. 14, Supplement Issue 2, 2018, pp. S519-S525.
Katoh, "Canonical and non-canonical WNT signaling in cancer stem cells and their niches: Cellular heterogeneity, omics reprogramming, targeted therapy and tumor plasticity (Review)," International Journal of Oncology, vol. 51, No. 5, 2017, pp. 1357-1369.
Liu et al., "The AMPK Inhibitor Compound C Is a Potent AMPK-Independent Antiglioma Agent," Molecular Cancer Therapeutics, vol. 13, No. 3, Mar. 2014, pp. 596-605.
Shin, "Laboratory of Molecular and Cellular Biology, Graduate School of Biostudies," Overview of Graduate School and Faculty of Pharmaceutical Sciences, Kyoto University, Sep. 2018, p. 43 (4 pages total), with partial English translation.
Wang et al., "Dynasore-induced potent ubiquitylation of the exon 19 deletion mutant of epidermal growth factor receptor suppresses cell growth and migration in non-small cell lung cancer," International Journal of Biochemistry and Cell Biology, vol. 105, 2018, pp. 1-12.
Wehbe et al., "Pifithrin-α Enhances Chemosensitivity by a p38 Mitogen-Activated Protein Kinase-Dependent Modulation of the Eukaryotic Initiation Factor 4E in Malignant Cholangiocytes," The Journal of Pharmacology and Experimental Therapeutics, vol. 319, No. 3, 2006, pp. 1153-1161.
Yin et al., "Glycogen Synthase Kinase 3β Inhibition as a Therapeutic Approach in the Treatment of Endometrial Cancer," International Journal of Molecular Sciences, vol. 14, No. 8, Aug. 12, 2013, pp. 16617-16637.
Yue et al., "Gain-of-function mutant p53 activates small GTPase Rac1 through SUMOylation to promote tumor progression," Genes & Development, vol. 31, No. 16, 2017, pp. 1641-1654 (15 pages total).
"Cancer Risk and Prevention," American Cancer Society, https://www.cancer.org/cancer/risk-prevention.html, Nov. 13, 2025, pp. 1-7.
Edwards et al., "The Remarkable Flexibility of the Human Antibody Repertoire; Isolation of Over One Thousand Different Antibodies to a Single Protein, BLyS," Journal of Molecular Biology, vol. 334, 2003, pp. 103-118.
Muro et al., "Irinotecan plus S-1 (IRIS) versus fluorouracil and folinic acid plus irinotecan (FOLFIRI) as second-line chemotherapy for metastatic colorectal cancer: a randomised phase 2/3 non-inferiority study (FIRIS study)," www.thelancet.com/oncology, vol. 11, Sep. 2010, pp. 853-860.
Schultheis et al., "Regorafenib in combination with FOLFOX or FOLFIRI as first- or second-line treatment of colorectal cancer: results of a multicenter, phase Ib study," Annals of Oncology, vol. 24, 2013, pp. 1560-1567.
Sela-Culang et al., "The structural basis of antibody-antigen recognition," Frontiers in Immunology, vol. 4, Article 302, Oct. 2013, pp. 1-13.
U.S. Office Action for U.S. Appl. No. 17/910,522, dated Nov. 28, 2025.
English translation of the International Search Report for International Application No. PCT/JP2024/032627, dated Dec. 3, 2024.
Lewington et al., "Bone-Seeking Radionuclides for Therapy," The Journal of Nuclear Medicine, vol. 46, No. 1 (Suppl), Jan. 2005, pp. 38S-47S.
Reubi et al., "Candidates for Peptide Receptor Radiotherapy Today and in the Future," The Journal of Nuclear Medicine, vol. 46, No. 1 (Suppl), Jan. 2005, pp. 67S-75S.

* cited by examiner

MEDICAMENT FOR TREATMENT AND/OR PREVENTION OF CANCER

TECHNICAL FIELD

The present invention relates to a medicament for treatment and/or prevention of cancer, comprising an antibody against CAPRIN-1 protein, or a fragment thereof, and an angiogenesis inhibitor and a taxane-based drug.

BACKGROUND ART

Various antibody medicines targeting specific antigen proteins on cancer cells are applied as therapeutic agents for cancers with fewer side effects to cancer treatment because of their cancer specificity. For example, cytoplasmic-activation and proliferation-associated protein 1 (CAPRIN-1) is expressed on cell membrane surfaces of many solid cancers. Antibodies against this CAPRIN-1 protein are known to be promising in pharmaceutical uses for treatment and/or prevention of cancers (Patent Literature 1).

In recent years, treatment methods using combinations of pluralities of therapeutic agents for cancer have been clinically used as standard treatment methods in order to enhance the effectiveness of the therapeutic agents for cancers. It has been performed in common to treat using a plurality of anticancer agents, for example, colon cancer is treated by a treatment method using a combination of irinotecan, folinic acid, and fluorouracil; breast cancer is treated by a treatment method using a combination of doxorubicin and cyclophosphamide or a combination of paclitaxel, trastuzumab, and Pertuzumab; and gastric cancer is treated using a plurality of anticancer agents such as carboplatin and fluorouracil. Therapeutic agents for cancers comprising anti-CAPRIN-1 antibodies as active ingredients have also been confirmed to have therapeutic effects on the cancers by combinations with chemotherapeutics (Patent Literature 2). However, treatment of a cancer by a combination of chemotherapeutics is not effectiver every cancer to which the treatment is applied, and few combinations of chemotherapeutics synergistically drastically enhance therapeutic effects, though some combinations additively enhance therapeutic effects.

One specific example of the cancer treatment method using a combination of a plurality of therapeutic agents for cancer includes a combination of an angiogenesis inhibitor (e.g., ramucirumab) and a taxane-based drug (e.g., paclitaxel).

The combination of ramucirumab and paclitaxel is a cancer treatment method that is carried out as the second-line treatment mainly for unresectable gastric cancer patients. Its usefulness for metastatic gastric cancer patients has also been reported. In the combined administration trial of ramucirumab and paclitaxel targeting gastroesophageal junction cancer or gastric adenocarcinoma patients (RAINBOW trial), the median overall survival of patients in a group given paclitaxel alone was 7.4 months (their median progression-free survival was 2.9 months), whereas the median overall survival of patients in a group given ramucirumab and paclitaxel was 9.6 months (their median progression-free survival was 4.4 months) (Non Patent Literature 1). As shown in this result, the combination of ramucirumab and paclitaxel slightly improves survival and is therefore regarded as a recommended treatment for gastric cancer.

In recent years, treatment using a combination of nivolumab, an immune checkpoint inhibitor, in addition to ramucirumab and paclitaxel has been. reported as to unresectable or relapsed gastroesophageal junction cancer patients, and in this treatment, patients who had become resistant after first-line treatment with a fluoropyridine-based drug and a platinum-based drug were treated by second-line treatment, resulting in 6-month progression-free survival rate of only 46% (Non Patent Literature 2).

CITATION LIST

Patent Literature

Patent literature 1: WO2010/016526
Patent literature 2: WO2011/096535

Non Patent Literature

Non Patent Literature 1: Hansjochen Wilke et al., Lancet Oncology, 2014, 15 (11), 1224-1235
Non Patent Literature 2: Shigenori Kadowaki et al., The ESMO World Congress on Gastrointestinal Cancer 2019, Abstract #SO-001

SUMMARY OF INVENTION

Technical Problem

An object of the present invention is to provide a medicament for treatment and/or prevention of cancer specifically expressing CAPRIN-1 protein on a cell surface.

Solution to Problem

As a result of intensive studies, the present inventors have found that a combination of an antibody against CAPRIN-1 protein, or a fragment thereof, having an immunological reactivity with cancer cells, and an angiogenesis inhibitor or an angiogenesis inhibitor and a taxane-based drug exerts a very strong antitumor effect on a cancer patient, in particular, a cancer patient with a previous history of cancer treatment with a medicament other than this combination therapy. On the basis of these findings, the present invention has been completed.

Specifically, the present invention relates to the following embodiments (1) to (18):

(1) A medicament for treatment and/or prevention of cancer, comprising an antibody or a fragment thereof having an immunological reactivity with CAPRIN-1 protein, and an angiogenesis inhibitor or an angiogenesis inhibitor and a taxane-based drug together or separately in combination.

(2) The medicament according to (1), wherein the angiogenesis inhibitor is an anti-VEGF inhibitor and/or an anti-vascular endothelial growth factor receptor (VEGFR) inhibitor.

(3) The medicament according to (1) or (2), wherein the angiogenesis inhibitor is bevacizumab and/or ramucirumab.

(4) The medicament according to any of (1) to (3), wherein the angiogenesis inhibitor is bevacizumab, ramucirumab and/or axitinib.

(5) The medicament according to any of (1) to (4), wherein the taxane-based drug is paclitaxel, docetaxel, nab-paclitaxel and/or a derivative of the drug.

(6) The medicament according to any of (1) to (5), wherein the cancer is cancer in a cancer patient who has not responded to cancer treatment with a medicament other than cancer treatment with a medicament comprising an antibody or a fragment thereof having an immunological reactivity with CAPRIN-1 protein, and an angiogenesis inhibitor or an angiogenesis inhibitor and a taxane-based drug together or separately in combination.

(7) The medicament according to any of (1) to (6), wherein the antibody or the fragment thereof has an immunological reactivity with CAPRIN-1 protein having an amino acid sequence represented by any one of the even numbered SEQ ID NOs: 2 to 30, or an amino acid sequence having 80% or more sequence identity with the amino acid sequence.

(8) The medicament according to any of (1) to (7), wherein the antibody or the fragment thereof has an immunological reactivity with an extracellular region of a CAPRIN-1 protein present on a cancer cell surface.

(9) The medicament according to any of (1) to (8), wherein the antibody or the fragment thereof has an immunological reactivity with a partial polypeptide of CAPRIN-1 protein, the partial polypeptide having an amino acid sequence represented by any one of SEQ ID NOs: 31 to 35, 296 to 299, 308 and 309, or an amino acid sequence having 80% or more sequence identity with the amino acid sequence.

(10) The medicament according to any of (1) to (9), wherein the antibody is a monoclonal antibody or a polyclonal antibody.

(11) The medicament according to any of (1) to (10), wherein the antibody or the fragment thereof is any one of the following (A) to (M):

(A) an antibody or a fragment thereof comprising a heavy-chain variable region comprising complementarity determining regions of SEQ ID NOs: 36, 37 and 38 (CDR1, CDR2 and CDR3, respectively) and a light-chain variable region comprising complementarity determining regions of SEQ ID NOs: 40, 41 and 42 (CDR1, CDR2 and CDR3, respectively), and having an immunological reactivity with CAPRIN-1 protein;

(B) an antibody or a fragment thereof comprising a heavy-chain variable region comprising complementarity determining regions of SEQ ID NOs: 44, 45 and 46 (CDR1, CDR2 and CDR3, respectively) and a light-chain variable region comprising complementarity determining regions of SEQ ID NOs: 48, 49 and 50 (CDR1, CDR2 and CDR3, respectively), and having an immunological reactivity with CAPRIN-1 protein;

(C) an antibody or a fragment thereof comprising a heavy-chain variable region comprising complementarity determining regions of SEQ ID NOs: 52, 53 and 54 (CDR1, CDR2 and CDR3, respectively) and a light-chain variable region comprising complementarity determining regions of SEQ ID NOs: 56, 57 and 58 (CDR1, CDR2 and CDR3, respectively), and having an immunological reactivity with CAPRIN-1 protein;

(D) an antibody or a fragment thereof comprising a heavy-chain variable region comprising complementarity determining regions of SEQ ID NOs: 60, 61 and 62 (CDR1, CDR2 and CDR3, respectively) and a light-chain variable region comprising complementarity determining regions of SEQ ID NOs: 64, 65 and 66 (CDR1, CDR2 and CDR3, respectively), and having an immunological reactivity with CAPRIN-1 protein;

(E) an antibody or a fragment thereof comprising a heavy-chain variable region comprising complementarity determining regions of SEQ ID NOs: 170, 171 and 172 (CDR1, CDR2 and CDR3, respectively) and a light-chain variable region comprising complementarity determining regions of SEQ ID NOs: 173, 174 and 175 (CDR1, CDR2 and CDR3, respectively), and having an immunological reactivity with CAPRIN-1 protein;

(F) an antibody or a fragment thereof comprising a heavy-chain variable region comprising complementarity determining regions of SEQ ID NOs: 176, 177 and 178 (CDR1, CDR2 and CDR3, respectively) and a light-chain variable region comprising complementarity determining regions of SEQ ID NOs: 179, 180 and 181 (CDR1, CDR2 and CDR3, respectively), and having an immunological reactivity with CAPRIN-1 protein;

(G) an antibody or a fragment thereof comprising a heavy-chain variable region comprising complementarity determining regions of SEQ ID NOs: 182, 183 and 184 (CDR1, CDR2 and CDR3, respectively) and a light-chain variable region comprising complementarity determining regions of SEQ ID NOs: 185, 186 and 187 (CDR1, CDR2 and CDR3, respectively), and having an immunological reactivity with CAPRIN-1 protein;

(H) an antibody or a fragment thereof comprising a heavy-chain variable region comprising complementarity determining regions of SEQ ID NOs: 188, 189 and 190 (CDR1, CDR2 and CDR3, respectively) and a light-chain variable region comprising complementarity determining regions of SEQ ID NOs: 191, 192 and 193 (CDR1, CDR2 and CDR3, respectively), and having an immunological reactivity with CAPRIN-1 protein;

(I) an antibody or a fragment thereof comprising a heavy-chain variable region comprising complementarity determining regions of SEQ ID NOs: 146, 147 and 148 (CDR1, CDR2 and CDR3, respectively) and a light-chain variable region comprising complementarity determining regions of SEQ ID NOs: 149, 150 and 151 (CDR1, CDR2 and CDR3, respectively), and having an immunological reactivity with CAPRIN-1 protein;

(J) an antibody or a fragment thereof comprising a heavy-chain variable region comprising complementarity determining regions of SEQ ID NOs: 272, 273 and 274 (CDR1, CDR2 and CDR3, respectively) and a light-chain variable region comprising complementarity determining regions of SEQ ID NOs: 275, 276 and 277 (CDR1, CDR2 and CDR3, respectively), and having an immunological reactivity with CAPRIN-1 protein;

(K) an antibody or a fragment thereof comprising a heavy-chain variable region comprising complementarity determining regions of SEQ ID NOs: 290, 291 and 292 (CDR1, CDR2 and CDR3, respectively) and a light-chain variable region comprising complementarity determining regions of SEQ ID NOs: 293, 294 and 295 (CDR1, CDR2 and CDR3, respectively), and having an immunological reactivity with CAPRIN-1 protein;

(L) an antibody or a fragment thereof comprising a heavy-chain variable region comprising complementarity determining regions of SEQ ID NOs: 300, 301, and 302 (CDR1, CDR2 and CDR3, respectively) and a light-chain variable region comprising complementarity determining regions of SEQ ID NOs: 304, 305, and 306 (CDR1, CDR2 and CDR3, respectively), and having an immunological reactivity with CAPRIN-1 protein; and (M) an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with CAPRIN-1 protein.

(12) The medicament according to any of (1) to (11), wherein the antibody or the fragment thereof is any one of the following (a) to (al):

(a) an antibody or a fragment thereof comprising a heavy-chain variable region comprising the amino acid sequence of SEQ ID NO: 39 and a light-chain variable region comprising the amino acid sequence of SEQ ID NO: 43;

(b) an antibody or a fragment thereof comprising a heavy-chain variable region comprising the amino acid sequence of SEQ ID NO: 47 and a light-chain variable region comprising the amino acid sequence of SEQ ID NO: 51;

(c) an antibody or a fragment thereof comprising a heavy-chain variable region comprising the amino acid sequence of SEQ ID NO: 55 and a light-chain variable region comprising the amino acid sequence of SEQ ID NO: 59;

(d) an antibody or a fragment thereof comprising a heavy-chain variable region comprising the amino acid sequence of SEQ ID NO: 63 and a light-chain variable region comprising the amino acid sequence of SEQ ID NO: 67;

(e) an antibody or a fragment thereof comprising a heavy-chain variable region comprising the amino acid sequence of SEQ ID NO: 68 and a light-chain variable region comprising the amino acid sequence of SEQ ID NO: 69;

(f) an antibody or a fragment thereof comprising a heavy-chain variable region comprising the amino acid sequence of SEQ ID NO: 70 and a light-chain variable region comprising the amino acid sequence of SEQ ID NO: 71;

(g) an antibody or a fragment thereof comprising a heavy-chain variable region comprising the amino acid sequence of SEQ ID NO: 72 and a light-chain variable region comprising the amino acid sequence of SEQ ID NO: 73;

(h) an antibody or a fragment thereof comprising a heavy-chain variable region comprising the amino acid sequence of SEQ ID NO: 74 and a light-chain variable region comprising the amino acid sequence of SEQ ID NO: 75;

(i) an antibody or a fragment thereof comprising a heavy-chain variable region comprising the amino acid sequence of SEQ ID NO: 76 and a light-chain variable region comprising the amino acid sequence of SEQ ID NO: 77;

(j) an antibody or a fragment thereof comprising a heavy-chain variable region comprising the amino acid sequence of SEQ ID NO: 78 and a light-chain variable region comprising the amino acid sequence of SEQ ID NO: 79;

(k) an antibody or a fragment thereof comprising a heavy-chain variable region comprising the amino acid sequence of SEQ ID NO: 80 and a light-chain variable region comprising the amino acid sequence of SEQ ID NO: 81;

(l) an antibody or a fragment thereof comprising a heavy-chain variable region comprising the amino acid sequence of SEQ ID NO: 82 and a light-chain variable region comprising the amino acid sequence of SEQ ID NO: 83;

(m) an antibody or a fragment thereof comprising a heavy-chain variable region comprising the amino acid sequence of SEQ ID NO: 84 and a light-chain variable region comprising the amino acid sequence of SEQ ID NO: 85;

(n) an antibody or a fragment thereof comprising a heavy-chain variable region comprising the amino acid sequence of SEQ ID NO: 86 and a light-chain variable region comprising the amino acid sequence of SEQ ID NO: 87;

(o) an antibody or a fragment thereof comprising a heavy-chain variable region comprising the amino acid sequence of SEQ ID NO: 88 and a light-chain variable region comprising the amino acid sequence of SEQ ID NO: 89;

(p) an antibody or a fragment thereof comprising a heavy-chain variable region comprising the amino acid sequence of SEQ ID NO: 90 and a light-chain variable region comprising the amino acid sequence of SEQ ID NO: 91;

(q) an antibody or a fragment thereof comprising a heavy-chain variable region comprising the amino acid sequence of SEQ ID NO: 92 and a light-chain variable region comprising the amino acid sequence of SEQ ID NO: 93;

(r) an antibody or a fragment thereof comprising a heavy-chain variable region comprising the amino acid sequence of SEQ ID NO: 94 and a light-chain variable region comprising the amino acid sequence of SEQ ID NO: 95;

(s) an antibody or a fragment thereof comprising a heavy-chain variable region comprising the amino acid sequence of SEQ ID NO: 96 and a light-chain variable region comprising the amino acid sequence of SEQ ID NO: 97;

(t) an antibody or a fragment thereof comprising a heavy-chain variable region comprising the amino acid sequence of SEQ ID NO: 98 and a light-chain variable region comprising the amino acid sequence of SEQ ID NO: 99;

(u) an antibody or a fragment thereof comprising a heavy-chain variable region comprising the amino acid sequence of SEQ ID NO: 100 and a light-chain variable region comprising the amino acid sequence of SEQ ID NO: 101;

(v) an antibody or a fragment thereof comprising a heavy-chain variable region comprising the amino acid sequence of SEQ ID NO: 102 and a light-chain variable region comprising the amino acid sequence of SEQ ID NO: 103;

(w) an antibody or a fragment thereof comprising a heavy-chain variable region comprising the amino acid sequence of SEQ ID NO: 104 and a light-chain variable region comprising the amino acid sequence of SEQ ID NO: 105;

(x) an antibody or a fragment thereof comprising a heavy-chain variable region comprising the amino acid sequence of SEQ ID NO: 106 and a light-chain variable region comprising the amino acid sequence of SEQ ID NO: 107;

(y) an antibody or a fragment thereof comprising a heavy-chain variable region comprising the amino acid sequence of SEQ ID NO: 108 and a light-chain variable region comprising the amino acid sequence of SEQ ID NO: 109;

(z) an antibody or a fragment thereof comprising a heavy-chain variable region comprising the amino acid sequence of SEQ ID NO: 110 and a light-chain variable region comprising the amino acid sequence of SEQ ID NO: 111;

(aa) an antibody or a fragment thereof comprising a heavy-chain variable region comprising the amino acid sequence of SEQ ID NO: 112 and a light-chain variable region comprising the amino acid sequence of SEQ ID NO: 113;

(ab) an antibody or a fragment thereof comprising a heavy-chain variable region comprising the amino acid sequence of SEQ ID NO: 114 and a light-chain variable region comprising the amino acid sequence of SEQ ID NO: 115;

(ac) an antibody or a fragment thereof comprising a heavy-chain variable region comprising the amino acid sequence of SEQ ID NO: 116 and a light-chain variable region comprising the amino acid sequence of SEQ ID NO: 117;

(ad) an antibody or a fragment thereof comprising a heavy-chain variable region comprising the amino acid sequence of SEQ ID NO: 118 and a light-chain variable region comprising the amino acid sequence of SEQ ID NO: 119;

(ae) an antibody or a fragment thereof comprising a heavy-chain variable region comprising the amino acid sequence of SEQ ID NO: 120 and a light-chain variable region comprising the amino acid sequence of SEQ ID NO: 121;

(af) an antibody or a fragment thereof comprising a heavy-chain variable region comprising the amino acid sequence of SEQ ID NO: 122 and a light-chain variable region comprising the amino acid sequence of SEQ ID NO: 123;

(ag) an antibody or a fragment thereof comprising a heavy-chain variable region comprising the amino acid sequence of SEQ ID NO: 124 and a light-chain variable region comprising the amino acid sequence of SEQ ID NO: 125;

(ah) an antibody or a fragment thereof comprising a heavy-chain variable region comprising the amino acid sequence of SEQ ID NO: 126 and a light-chain variable region comprising the amino acid sequence of SEQ ID NO: 127;

(ai) an antibody or a fragment thereof comprising a heavy-chain variable region comprising the amino acid sequence of SEQ ID NO: 128 and a light-chain variable region comprising the amino acid sequence of SEQ ID NO: 129;

(aj) an antibody or a fragment thereof comprising a heavy-chain variable region comprising the amino acid sequence of SEQ ID NO: 130 and a light-chain variable region comprising the amino acid sequence of SEQ ID NO: 131;

(ak) an antibody or a fragment thereof comprising a heavy-chain variable region comprising the amino acid sequence of SEQ ID NO: 132 and alight-chain variable region comprising the amino acid sequence of SEQ ID NO: 133; and (al) an antibody or a fragment thereof comprising a heavy-chain variable region comprising the amino acid sequence of SEQ ID NO: 303 and a light-chain variable region comprising the amino acid sequence of SEQ ID NO: 307.

(13) The medicament according to any of (1) to (12), wherein the antibody is a human antibody, a humanized antibody, a chimeric antibody or a single chain antibody.

(14) The medicament according to any of (1) to (13), wherein the cancer is cancer expressing CAPRIN-1 protein on a cell membrane surface.

(15) The medicament according to any of (1) to (14), wherein the cancer is gastric cancer, breast cancer, kidney cancer, pancreatic cancer, colon cancer, bile duct cancer, melanoma, lung cancer, renal cell carcinoma, Hodgkin's lymphoma, head and neck cancer, mesothelioma, colorectal cancer, esophageal cancer, gastroesophageal junction cancer, hepatocellular carcinoma, glioblastoma, urothelial carcinoma, ovarian cancer, urinary bladder cancer, uterine cancer, primary central nervous system lymphoma, primary testicular lymphoma, biliary tract cancer, brain tumor, prostate cancer, leukemia, lymphoma, liver cancer, sarcoma, fibrosarcoma, mastocytoma, adrenocortical carcinoma, Ewing's tumor, multiple myeloma, testicular cancer, thyroid cancer, basal cell carcinoma, Paget's disease or skin cancer.

(16) An agent increasing drug efficacy of a pharmaceutical composition for treatment and/or prevention of cancer comprising an antibody or a fragment thereof having an immunological reactivity with CAPRIN-1 protein as an active ingredient, wherein the agent comprises an angiogenesis inhibitor or an angiogenesis inhibitor and a taxane-based drug, as active ingredients.

(17) An agent increasing drug efficacy of a pharmaceutical composition for treatment and/or prevention of cancer comprising an angiogenesis inhibitor or an angiogenesis inhibitor and a taxane-based drug as active ingredients, wherein the agent comprises an antibody or a fragment thereof having an immunological reactivity with CAPRIN-1 protein, as an active ingredient.

(18) A method for treating and/or preventing cancer, comprising administering an antibody or a fragment thereof having an immunological reactivity with CAPRIN-1 protein, and an angiogenesis inhibitor or an angiogenesis inhibitor and a taxane-based drug together or separately to a subject.

The present specification encompasses the contents disclosed in Japanese Patent Application No. 2020-043021 on which the priority of the present application is based.

Advantageous Effects of Invention

The combination of an antibody against CAPRIN-1 protein, or a fragment thereof, and an angiogenesis inhibitor or an angiogenesis inhibitor and a taxane-based drug according to the present invention exerts a stronger antitumor effect than that of the antibody against CAPRIN-1 protein alone or an existing chemotherapeutic (a combination of an angiogenesis inhibitor and a taxane-based drug). The combination of an antibody against CAPRIN-1 protein, or a fragment thereof, and an angiogenesis inhibitor or a drug comprising an angiogenesis inhibitor and a taxane-based drug according to the present invention exhibits a stronger antitumor effect than that of existing anticancer agent therapy or treatment with the antibody against CAPRIN-1 protein alone. Thus, the combination of the antibody against CAPRIN-1 protein, or the fragment thereof, and an angiogenesis inhibitor or an angiogenesis inhibitor and a taxane-based drug is effective for treatment or prevention of cancer.

DESCRIPTION OF EMBODIMENTS

The antitumor activity of the combination of an antibody against CAPRIN-1 protein or a fragment thereof (hereinafter, referred to as an "anti-CAPRIN-1 antibody"), and an angiogenesis inhibitor or an angiogenesis inhibitor and a taxane-based drug (hereinafter, these are collectively referred to as an "angiogenesis inhibitor, etc." used in the present invention can be evaluated by examining in vivo the inhibition of tumor grow a tumor-bearing animal as mentioned later.

The term "combination" described herein refers to simultaneous administration or administration in a predetermined interval of the anti-CAPRIN-1 antibody and an angiogenesis inhibitor, etc. as independent active ingredients to the same organism. The interval may be simultaneous administration or may be 30 minutes later, 1 hour later, 3 hours later, 6 hours later, 12 hours later, 1 day later, 3 days later, 5 days later, 7 days later, 2 weeks later, 3 weeks later, or 4 weeks later. The anti-CAPRIN-1 antibody or an angiogenesis inhibitor, etc. may be administered when another active ingredient exhibits its activity in vivo. The anti-CAPRIN-1 antibody may be administered first, or the angiogenesis inhibitor, etc. may be administered first.

The term "comprising together or separately in combination" described herein refers to comprising a plurality of drugs in a form that allows the drugs to be administered simultaneously or separately to a patient. The form may be, for example, the form of a so-called mixed formulation in which a plurality of drugs is mixed, or may be the form of a so-called kit formulation (pharmaceutical kit) comprising a plurality of drugs as individual formulations. The form also encompasses the form of a kit formulation comprising a plurality of drugs in any combination in two or more of formulations.

Such a kit formulation according to the present invention may be, for example, a kit formulation comprising a formulation (or a pharmaceutical composition) comprising the anti-CAPRIN-1 antibody, and a formulation (or a pharmaceutical composition) comprising an angiogenesis inhibitor. As another example, the kit formulation according to the present invention may be a kit formulation comprising a formulation (or a pharmaceutical composition) comprising the anti-CAPRIN-1 antibody, a formulation (or a pharmaceutical composition) comprising an angiogenesis inhibitor, and a formulation (or a pharmaceutical composition) comprising a taxane-based drug. As an alternative example, the kit formulation according to the present invention may be a kit formulation comprising: (i) a formulation (or a pharmaceutical composition) comprising the anti-CAPRIN-1 antibody and an angiogenesis inhibitor; and/or (ii) a formulation (or a pharmaceutical composition) comprising the anti-CAPRIN-1 antibody and a taxane-based drug; and (iii) a formulation (or a pharmaceutical composition) comprising other active ingredients.

The anti-CAPRIN-1 antibody according to the present invention may be a monoclonal antibody or a polyclonal antibody and is preferably a monoclonal antibody, The antibody of the present invention may be any type of antibody, as long as it can exhibit antitumor activity. The antibody is a recombinant antibody, a human antibody, a humanized antibody, a chimeric antibody, or a non-human animal antibody.

Subjects in need of treatment and/or prevention of cancer according to the present invention are mammals such as human, pet animals, livestock animals, or sport animals. The preferred subject is a human.

Medicaments comprising an anti-CAPRIN-1 antibody and an angiogenesis inhibitor, etc. as active ingredients, and methods for treating and/or preventing cancer, related to the present invention, will be explained below.

Anti-CAPRIN-1 Antibody

Among CAPRIN-1 proteins having an amino acid sequence shown in any one of the even numbered SEQ ID NOs: 2 to 30, which are specific examples of antigens having an immunological reactivity with the anti-CAPRIN-1 antibody used in the present invention, the amino acid sequences shown in SEQ ID NOs: 6, 8, 10, 12 and 14 are amino acid sequences of canine CAPRIN-1 proteins; the amino acid sequences shown in SEQ ID NOs: 2 and 4 are amino acid sequences of human CAPRIN-1 proteins; the amino acid sequence shown in SEQ ID NO: 16 is an amino acid sequence of a bovine CAPRIN-1 protein; the amino acid sequence shown in SEQ ID NO: 18 is an amino acid sequence of a horse CAPRIN-1 protein; the amino acid sequences shown in SEQ ID NOs: 20, 22, 24, 26 and 28 are amino acid sequences of mouse CAPRIN-1 proteins; and the amino acid sequence shown in SEQ ID NO: 30 is an amino acid sequence of a chicken CAPRIN-1 protein.

The anti-CAPRIN-1 antibody used in the present invention may have an immunological reactivity with a CAPRIN-1 protein variant having 80% or more, preferably 90% or more, more preferably 95% or more, and further preferably 99% or more sequence identity to the amino acid sequence shown in any one of the even numbered SEQ ID NOs: 2 to 30. The term "% sequence identity" as used herein means a percentage of the number of identical amino acids (or nucleotides) to the total number of amino acids (or nucleotides) in the case that two sequences are aligned such that maximum similarity can be achieved with or without introduction of gaps.

In the present invention, the anti-CAPRIN-1 antibody refers to an antibody or a fragment (antigen binding fragment) thereof having an immunological reactivity with a full-length CAPRIN-1 protein or a fragment thereof. The term "immunological reactivity" used herein indicates the characteristics of an antibody specifically binding in vivo or in vitro to a CAPRIN-1 protein or a partial polypeptide thereof.

The anti-CAPRIN-1 antibody used in the present invention may be a monoclonal antibody or a polyclonal antibody.

Polyclonal antibodies haying an immunological reactivity with a full-length CAPRIN-1 protein or a fragment thereof (anti-CAPRIN-1 polyclonal antibodies) can be obtained, for example, in a manner described below. Mice, human antibody-producing mice, rats, rabbits, chickens, or the like are immunized using a naturally occurring CAPRIN-1 protein or a protein fused with GST or the like, or a partial peptide thereof, followed by obtainment of serum, and then by purification from the obtained serum via ammonium sulfate precipitation, protein A, protein G, DEAE ion-exchange columns, affinity columns to which a CAPRIN-1 protein or a partial peptide is coupled, or the like.

Nucleotide sequences and amino acid sequences of CAPRIN-1 and homologs thereof used in the immunization can be obtained by, for example, accessing the website of GenBank (NCBI, USA) and using the BLAST or FASTA algorithm (Karlin and Altschul, Proc. Natl, Acad. Sci, USA, 90: 5873-5877, 1993 and Altschul et at, Nucleic Acids Res. 25: 3389-3402, 1997). Methods for producing CAPRIN-1 protein can be obtained with reference to WO2014/012479 or may employ cells or the like expressing CAPRIN-1 protein.

Monoclonal antibodies having an immunological reactivity with a full-length CAPRIN-1 protein or a fragment thereof (anti-CAPRIN-1 monoclonal antibodies) can be obtained, for example, in a manner described below. Breast cancer cells SK-BR-3 expressing CAPRIN-1, a full-length CAPRIN-1 protein or a fragment thereof, or the like is administered to mice for immunization. Splenocytes separated from the mice are fused with myeloma cells. Clones capable of producing anti-CAPRIN-1 monoclonal antibodies can be selected from the obtained fusion cells (hybridomas) to obtain these antibodies. The antibodies produced from the selected hybridomas can be obtained in the same way as the aforementioned method for purifying polyclonal antibodies.

The antibody used in the present invention includes human antibodies, humanized antibodies, chimeric antibodies, and non-human animal antibodies.

For human antibodies, human lymphocytes infected with EB virus are sensitized with a protein, protein-expressing cells, or a lysate thereof. The sensitized lymphocytes are fused with human-derived myeloma cells such as U266 cells. Antibodies having an immunological reactivity with a full-length CAPRIN-1 protein or a fragment thereof can be obtained from the obtained fusion cells.

A humanized antibody is a modified antibody, and it is sometimes referred to as a reshaped human antibody. It is known that a humanized antibody is constructed by transplanting complementarity determining regions of an immunized animal-derived antibody into complementarity determining regions of a human antibody. In addition, a general gene recombinant technique therefor is well known. Specifically, a DNA sequence designed in a manner that allows complementarity determining regions of mouse or rabbit antibody to be ligated to human antibody framework regions is synthesized by the PCR method using several oligonucleotides prepared in such a manner that the oligonucleotides have portions overlapping each other at one end of each thereof. A humanized antibody can be obtained by ligating the above obtained DNA to DNA encoding a human antibody constant region, incorporating the resultant into an expression vector, and introducing the vector into a host for antibody production (see EP-A-239400 and WO96/02576). Framework regions of human antibody ligated to each other via complementarity determining regions are selected on the assumption that complementarity determining regions can form an effective antigen binding site. If necessary, amino acids in framework regions of an antibody variable region may be substituted in such a manner that complementarity determining regions in a reshaped human antibody form an appropriate antigen binding site (Sato K. et al., Cancer Research 1993, 53: 851-856). In addition, the framework regions may be substituted with framework regions from a different human antibody (see WO99/51743).

In general, antibodies are heteromultimeric glycoproteins each comprising at least two heavy chains and two light chains. Antibodies each comprise two identical light chains and two identical heavy chains. Each heavy chain has a heavy-chain variable region at one end thereof, to which some constant regions are bound in series. Each light chain has a light-chain variable region at one end thereof to which some constant regions are bound in series. Variable regions have a specific variable region, which is called complementarity determining region (CDR) and imparts binding specificity to an antibody. A relatively conserved portion in a variable region is called a framework region (FR). A complete heavy-chain or light-chain variable region comprises 4 FRs connected to each other via 3 CDRs (CDR1 to CDR3).

Sequences of human-derived heavy-chain and light-chain constant regions and variable regions can be obtained from, for example, NCBI (USA; GenBank, UniGene, etc.). For example, for a human IgG1 heavy-chain constant region, see registration No. J00228; for a human IgG2 heavy-chain constant region, see registration No. J00230; for a human light chain κ constant region, see sequences such as registration Nos. V00557, X64135, and X64133; and for a human light chain λ constant region, see sequences such as registration Nos. X64132 and X64134.

A chimeric antibody is an antibody produced by combining sequences from different animals. An example thereof is an antibody consisting of mouse antibody heavy-chain and light-chain variable regions and human antibody heavy-chain and light-chain constant regions. Such a chimeric antibody can be produced by a known method. For example, it can be obtained by ligating DNA encoding an antibody V region to DNA encoding a human antibody C region, incorporating the resultant into an expression vector, and introducing the vector into a host for antibody production.

Non-human animal antibodies are obtained by immunizing animals with sensitizing antigens according to a known method or by intraperitoneally, intracutaneously, or subcutaneously injecting sensitizing antigens into animals such as mice as a general method. For injecting sensitizing antigens, an appropriate amount of various adjuvants including CFA (complete Freund's adjuvant) is mixed therewith and the mixture is administered to animals several times. After immunization of animals and confirmation of an anti-CAPRIN-1 antibody contained in serum, the serum is obtained and a non-human animal antibody can be obtained by purification via ammonium sulfate precipitation, protein A, protein G, DEAE ion-exchange columns, affinity columns to which a CAPRIN-1 protein or a partial peptide is coupled, or the like, as mentioned above. In the case of obtaining monoclonal antibodies from non-human animals, a monoclonal antibody is obtained by collecting immune cells from the immunized animals and subjecting them to cell fusion with myeloma cells. The cell fusion of immune cells with myeloma cells can be carried out according to a known method (see Kohler, G. and Milstein, C. Methods Enzymol. (1981) 73, 3-46).

The antibody used in the present invention can also be obtained as a gene recombinant antibody produced by cloning an antibody gene front a hybridoma, incorporating the clone into an adequate vector, introducing the vector into a host, and producing the antibody by using a gene recombinant technique (see Carl, A. K. Borrebaeck, James, W. Larrick, THERAPEUTIC MONOCLONAL ANTIBODIES, Published in the United Kingdom by MACMILLAN PUBLISHERS LTD, 1990).

Amino acids in a variable region (e.g., FR) or a constant region in the anti-CAPRIN-1 antibody used in the present invention may be substituted with different amino acids. The amino acid substitution is a substitution of 1 or several, for example, less than 15, less than 10, not more than 8, not more than 6, not more than 5, not more than 4, not more than 3, or not more than 2 amino acids, preferably 1 to 9 amino acids. A substituted antibody should have characteristics of specifically binding to the antigen and binding affinity for the antigen equivalent to or higher than those of an unsubstituted antibody and should be an antibody that causes no rejection when applied to humans. The amino acid substitution is preferably a conservative amino acid substitution, which is a substitution between amino acids haying similar characteristics in terms of charge, side chains, polarity, aromaticity, and the like. For example, characteristically similar amino acids can be classified into the following types: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched-chain amino acids (threonine, valine, isoleucine); and aromatic amino acids (phenylalanine, tyrosine, tryptophan, and histidine).

The anti-CAPRIN-1 antibody used in the present invention is expected to have a stronger antitumor effect when having higher binding affinity for CAPRIN-1 protein on the cancer cell surface. Association constant (affinity constant) Ka (kon/koff) is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $00^{13}$ $M^{-1}$.

The anti-CAPRIN-1 antibody used in the present invention may be chemically modified. Examples of such an antibody modifier can include antibodies bound to various molecules such as polyethylene glycol (PEG) and antitumor compounds (for example, antitumor agents listed below). Regarding antibody modifiers of the present invention, substances that bind to an antibody are not limited. Such an antibody modifier can be obtained by chemically modifying an obtained antibody. Methods of such modification have been already established in the field related to the present invention.

The binding strength of the anti-CAPRIN-1 antibody used in the present invention against effector cells can be improved by substituting 1, 2 or several amino acids in the heavy-chain constant region of the antibody or by removing fucose bound to N-acetylglucosamine in a N-glycoside-linked sugar chain bound to the heavy-chain constant region. The anti-CAPRIN-1 antibody described above may have the amino acid substitution alone or may be a composition with an antibody bound to fucose.

Antibodies in which 1, 2 or several amino acids in the heavy-chain constant region have been substituted can be produced with reference to, for example, WO2004/063351, WO2011/120135, U.S. Pat. No. 8,388,955, WO2011/005481, U.S. Pat. No. 6,737,056, and WO2005/063351.

Antibodies in which fucose bound to N-acetylglucosamine in a N-glycoside-linked sugar chain in the heavy-chain constant region has been removed, or producing cells thereof can be produced with reference to U.S. Pat. No. 6,602,684, EP Patent No. 1914244, and U.S. Pat. No. 7,579,170. Compositions of antibodies in which fucose bound to N-acetylglucosamine in a N-glycoside-linked sugar chain bound to the heavy-chain constant region has been removed, with antibodies bound to fucose, or producing cells thereof can be produced with reference to, for example, U.S. Pat. No. 8,642,292.

The anti-CAPRIN-1 polyclonal antibody and the anti-CAPRIN-1 monoclonal antibody used in the present invention, methods for producing or purifying antibodies and methods for producing a CAPRIN-1 protein or partial polypeptide thereof used in immunization can be obtained with reference to WO2010/016526. WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125630, WO2013/125640, WO2013/147169, WO2013/147176 and WO2015/020212.

Specific examples of the anti-CAPRIN-1 antibody according to the present invention include anti-CAPRIN-1 antibodies described in WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125630, WO2013/125640, WO2013/147169, WO2013/147176 and WO2015/020212 mentioned above. Preferred examples of the anti-CAPRIN-1 antibody include the following.

An antibody or a fragment thereof having an immunological reactivity with a partial polypeptide of a CAPRIN-1 protein having the amino acid sequence shown in SEQ ID NO: 2 or SEQ ID NO: 4 or an amino acid sequence having 80% or more (preferably 85% or more, more preferably 90% or more, further preferably 95% or more, and still further preferably 99% or more) sequence identity to the amino acid sequence.

An antibody or a fragment thereof having an immunological reactivity with a partial polypeptide of CAPRIN-1 protein, the partial polypeptide having the amino acid sequence shown in SEQ ID NO: 31 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 36, and 38 (CDR1, CDR2 and CDR3, respectively) and a light-chain variable region comprising complementarity determining regions of SEQ ID NOs: 40, 41 and 42 (CDR1, CDR2 and CDR3, respectively), and having an immunological reactivity with a CAPRIN-1 protein, an antibody or a fragment thereof comprising a heavy-chain variable region comprising complementarity determining regions of SEQ ID NOs: 140, 141 and 142 (CDR1, CDR2 and CDR3, respectively) and a light-chain variable region comprising complementarity determining regions of SEQ ID NOs: 143, 144 and 145 (CDR1, CDR2 and CDR3, respectively), and having an immunological reactivity with a CAPRIN-1 protein, or an antibody or a fragment thereof comprising a heavy-chain variable region comprising complementarity determining regions of SEQ ID NOs: 164, 165 and 166 (CDR1, CDR2 and CDR3, respectively) and a light-chain variable region comprising complementarity determining regions of SEQ ID NOs: 167, 168 and 169 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 39 and a light-chain variable region comprising the amino acid sequence of SEQ ID NO: 43, an antibody or a fragment thereof comprising a heavy-chain variable region comprising the amino acid sequence of SEQ ID NO: 70 and a light-chain variable region comprising the amino acid sequence of SEQ ID NO: 71, or an antibody or a fragment thereof comprising a heavy-chain variable region comprising the amino acid sequence of SEQ ID NO: 78 and a light-chain variable region comprising the amino acid sequence of SEQ ID NO: 79.

An antibody or a fragment thereof having an immunological reactivity with a partial polypeptide of CAPRIN-1 protein, the partial polypeptide having the amino acid sequence shown in SEQ ID NO: 33 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 60, 61 and 62 (CDR1, CDR2 and CDR3, respectively) and a light-chain variable region comprising complementarity determining regions of SEQ ID NOs: 64, 65 and 66 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 63 and a light-chain variable region comprising the amino acid sequence of SEQ ID NO: 67.

An antibody or a fragment thereof having an immunological reactivity with a partial polypeptide of CAPRIN-1 protein, the partial polypeptide having the amino acid sequence shown in SEQ ID NO: 32 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 52, 53 and 54 (CDR1, CDR2 and CDR3, respectively) and a light-chain variable region comprising complementarity determining regions of SEQ ID NOs: 56, 57 and 58 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 55 and a light-chain variable region comprising the amino acid sequence of SEQ ID NO: 59.

An antibody or a fragment thereof having an immunological reactivity with a partial polypeptide of CAPRIN-1 protein, the partial polypeptide having the amino acid sequence shown in SEQ ID NO: 34 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 170, 171 and 172 (CDR1, CDR2 and CDR3, respectively) and a light-chain variable region comprising complementarity determining regions of SEQ ID NOs: 173, 174 and 175 (CDR1, CDR2 and CDR3, respectively), and having an immunological reactivity with a CAPRIN-1 protein, or an antibody or a fragment thereof comprising a heavy-chain variable region comprising complementarity determining regions of SEQ ID NOs: 176, 177 and 178 (CDR1, CDR2 and CDR3, respectively) and a light-chain variable region comprising complementarity determining regions of SEQ ID NOs: 179, 180 and 181 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 80 and a light-chain variable region comprising the amino acid sequence of SEQ ID NO: 81, or an antibody or a fragment thereof comprising a heavy-chain variable region comprising the amino acid sequence of SEQ ID NO: 82 and a light-chain variable region comprising the amino acid sequence of SEQ ID NO: 83.

An antibody or a fragment thereof having an immunological reactivity with a partial polypeptide of CAPRIN-1 protein, the partial polypeptide having the amino acid sequence shown in SEQ ID NO: 35 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 182, 183 and 184 (CDR1, CDR2 and CDR3, respectively) and a light-chain variable region comprising complementarity determining regions of SEQ ID NOs: 185, 186 and 187 (CDR1, CDR2 and CDR3, respectively), and having an immunological reactivity with a CAPRIN-1 protein, or an antibody or a fragment thereof comprising a heavy-chain variable region comprising complementarity determining regions of SEQ ID NOs: 188, 189 and 190 (CDR1, CDR2 and CDR3, respectively) and a light-chain variable region comprising complementarity determining regions of SEQ ID NOs: 191, 192 and 193 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 84 and a light-chain variable region comprising the amino acid sequence of SEQ ID NO: 85, or an antibody or a fragment thereof comprising a heavy-chain variable region comprising the amino acid sequence of SEQ ID NO: 86 and a light-chain variable region comprising the amino acid sequence of SEQ ID NO: 87.

An antibody or a fragment thereof comprising a heavy-chain variable region comprising complementarity determining regions of SEQ ID NOs: 44, 45 and 46 (CDR1, CDR2 and CDR3, respectively) and a light-chain variable region comprising complementarity determining regions of SEQ ID NOs: 48, 49 and 50 (CDR1, CDR2 and CDR3, respectively), and having an immunological reactivity with a CAPRIN-1 protein, and preferably an antibody or a fragment thereof comprising a heavy-chain variable region comprising the amino acid sequence of SEQ ID NO: 47 and a light-chain variable region comprising the amino acid sequence of SEQ ID NO: 51.

An antibody or a fragment thereof having an immunological reactivity with a partial polypeptide of CAPRIN-1 protein, the partial polypeptide having the amino acid sequence shown in SEQ ID NO: 296 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 146, 147 and 148 (CDR1, CDR2 and CDR3, respectively) and a light-chain variable region comprising complementarity determining regions of SEQ ID NOs: 149, 150 and 151 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 72 and a light-chain variable region comprising the amino acid sequence of SEQ ID NO: 73.

An antibody or a fragment thereof having an immunological reactivity with a partial polypeptide of CAPRIN-1 protein, the partial polypeptide having the amino acid sequence shown in SEQ ID NO: 297 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 272, 273 and 274 (CDR1, CDR2 and CDR3, respectively) and a light-chain variable region comprising complementarity determining regions of SEQ ID NOs: 275, 276 and 277 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 114 and a light-chain variable region comprising the amino acid sequence of SEQ ID NO: 115.

An antibody or a fragment thereof having an immunological reactivity with a partial polypeptide of CAPRIN-1 protein, the partial polypeptide having the amino acid sequence shown in SEQ ID NO: 298 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 290, 291 and 292 (CDR1, CDR2 and CDR3, respectively) and a light-chain variable region comprising complementarity determining regions of SEQ ID NOs: 293, 294 and 295 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 120 and a light-chain variable region comprising the amino acid sequence of SEQ ID NO: 121.

An antibody or a fragment thereof having an immunological reactivity with a partial polypeptide of CAPRIN-1 protein, the partial polypeptide having the amino acid sequence shown in SEQ ID NO: 299 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 300, 301, and 302 (CDR1, CDR2 and CDR3, respectively) and a light-chain variable region comprising complementarity determining regions of SEQ ID NOs: 304, 305, 306 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 303 and a light-chain variable region comprising the amino acid sequence of SEQ ID NO: 307.

An antibody or a fragment thereof having an immunological reactivity with a partial polypeptide of CAPRIN-1 protein, the partial polypeptide having the amino acid sequence shown in SEQ ID NO: 308 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 68 and a light-chain variable region comprising the amino acid sequence of SEQ ID NO: 69.

An antibody or a fragment thereof having an immunological reactivity with a partial polypeptide of CAPRIN-1 protein, the partial polypeptide having the amino acid sequence shown in SEQ ID NO: 309 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 68 and a light-chain variable region comprising the amino acid sequence of SEQ ID NO: 69.

In addition, the following anti-CAPRIN-1 antibodies are preferably used.

An antibody or a fragment thereof comprising a heavy-chain variable region comprising the amino acid sequence of SEQ ID NO: 68 and a light-chain variable region comprising the amino acid sequence of SEQ ID NO: 69.

An antibody or a fragment thereof comprising a heavy-chain variable region comprising the amino acid sequence of SEQ ID NO: 70 and a light-chain variable region comprising the amino acid sequence of SEQ ID NO: 71.

An antibody or a fragment thereof comprising a heavy-chain variable region comprising the amino acid sequence of SEQ ID NO: 72 and a light-chain variable region comprising the amino acid sequence of SEQ ID NO: 73.

An antibody or a fragment thereof comprising a heavy-chain variable region comprising the amino acid sequence of SEQ ID NO: 74 and a light-chain variable region comprising the amino acid sequence of SEQ ID NO: 75.

An antibody or a fragment thereof comprising a heavy-chain variable region comprising the amino acid sequence of SEQ ID NO: 76 and a light-chain variable region comprising the amino acid sequence of SEQ ID NO: 77.

An antibody or a fragment thereof comprising a heavy-chain variable region comprising the amino acid sequence of SEQ ID NO: 78 and a light-chain variable region comprising the amino acid sequence of SEQ ID NO: 79.

An antibody or a fragment thereof comprising a heavy-chain variable region comprising the amino acid sequence of SEQ ID NO: 80 and a light-chain variable region comprising the amino acid sequence of SEQ ID NO: 81.

An antibody or a fragment thereof comprising a heavy-chain variable region comprising the amino acid sequence of SEQ ID NO: 82 and a light-chain variable region comprising the amino acid sequence of SEQ ID NO: 83.

An antibody or a fragment thereof comprising a heavy-chain variable region comprising the amino acid sequence of SEQ ID NO: 84 and a light-chain variable region comprising the amino acid sequence of SEQ ID NO: 85.

An antibody or a fragment thereof comprising a heavy-chain variable region comprising the amino acid sequence of SEQ ID NO: 86 and a light-chain variable region comprising the amino acid sequence of SEQ ID NO: 87.

An antibody or a fragment thereof comprising a heavy-chain variable region comprising the amino acid sequence of SEQ ID NO: 88 and a light-chain variable region comprising the amino acid sequence of SEQ ID NO: 89.

An antibody or a fragment thereof comprising a heavy-chain variable region comprising the amino acid sequence of SEQ ID NO: 90 and a light-chain variable region comprising the amino acid sequence of SEQ ID NO: 91.

An antibody or a fragment thereof comprising a heavy-chain variable region comprising the amino acid sequence of SEQ ID NO: 92 and a light-chain variable region comprising the amino acid sequence of SEQ ID NO: 93.

An antibody or a fragment thereof comprising a heavy-chain variable region comprising the amino acid sequence of SEQ ID NO: 94 and a light-chain variable region comprising the amino acid sequence of SEQ ID NO: 95.

An antibody or a fragment thereof comprising a heavy-chain variable region comprising the amino acid sequence of SEQ ID NO: 96 and a light-chain variable region comprising the amino acid sequence of SEQ ID NO: 97.

An antibody or a fragment thereof comprising a heavy-chain variable region comprising the amino acid sequence of SEQ ID NO: 98 and a light-chain variable region comprising the amino acid sequence of SEQ ID NO: 99.

An antibody or a fragment thereof comprising a heavy-chain variable region comprising the amino acid sequence of SEQ ID NO: 100 and a light-chain variable region comprising the amino acid sequence of SEQ ID NO: 101.

An antibody or a fragment thereof comprising a heavy-chain variable region comprising the amino acid sequence of SEQ ID NO: 102 and a light-chain variable region comprising the amino acid sequence of SEQ ID NO: 103.

An antibody or a fragment thereof comprising a heavy-chain variable region comprising the amino acid sequence of SEQ ID NO: 104 and a light-chain variable region comprising the amino acid sequence of SEQ ID NO: 105.

An antibody or a fragment thereof comprising a heavy-chain variable region comprising the amino acid sequence of SEQ ID NO: 106 and a light-chain variable region comprising the amino acid sequence of SEQ ID NO: 107.

An antibody or a fragment thereof comprising a heavy-chain variable region comprising the amino acid sequence of SEQ ID NO: 108 and a light-chain variable region comprising the amino acid sequence of SEQ ID NO: 109.

An antibody or a fragment thereof comprising a heavy-chain variable region comprising the amino acid sequence of SEQ ID NO: 110 and a light-chain variable region comprising the amino acid sequence of SEQ ID NO: 111.

An antibody or a fragment thereof comprising a heavy-chain variable region comprising the amino acid sequence of SEQ ID NO: 112 and a light-chain variable region comprising the amino acid sequence of SEQ ID NO: 113.

An antibody or a fragment thereof comprising a heavy-chain variable region comprising the amino acid sequence of SEQ ID NO: 114 and a light-chain variable region comprising the amino acid sequence of SEQ ID NO: 115.

An antibody or a fragment thereof comprising a heavy-chain variable region comprising the amino acid sequence of SEQ ID NO: 116 and a light-chain variable region comprising the amino acid sequence of SEQ ID NO: 117.

An antibody or a fragment thereof comprising a heavy-chain variable region comprising the amino acid sequence of SEQ ID NO: 118 and a light-chain variable region comprising the amino acid sequence of SEQ ID NO: 119.

An antibody or a fragment thereof comprising a heavy-chain variable region comprising the amino acid sequence of SEQ ID NO: 120 and a light-chain variable region comprising the amino acid sequence of SEQ ID NO: 121.

An antibody or a fragment thereof comprising a heavy-chain variable region comprising the amino acid sequence of SEQ ID NO: 122 and a light-chain variable region comprising the amino acid sequence of SEQ ID NO: 123.

An antibody or a fragment thereof comprising a heavy-chain variable region comprising the amino acid sequence of SEQ ID NO: 124 and a light-chain variable region comprising the amino acid sequence of SEQ ID NO: 125.

An antibody or a fragment thereof comprising a heavy-chain variable region comprising the amino acid sequence of SEQ ID NO: 126 and a light-chain variable region comprising the amino acid sequence of SEQ ID NO: 127.

An antibody or a fragment thereof comprising a heavy-chain variable region comprising the amino acid sequence of SEQ ID NO: 128 and a light-chain variable region comprising the amino acid sequence of SEQ ID NO: 129.

An antibody or a fragment thereof comprising a heavy-chain variable region comprising the amino acid sequence of SEQ ID NO: 130 and a light-chain variable region comprising the amino acid sequence of SEQ ID NO: 131.

An antibody or a fragment thereof comprising a heavy-chain variable region comprising the amino acid sequence of SEQ ID NO: 132 and a light-chain variable region comprising the amino acid sequence of SEQ ID NO: 133.

An antibody or a fragment thereof comprising a heavy-chain variable region comprising the amino acid sequence of SEQ ID NO: 303 and a light-chain variable region comprising the amino acid sequence of SEQ ID NO: 307.

In Examples mentioned later, a polyclonal antibody or a monoclonal antibody against full-length CAPRIN-1 protein or a polypeptide of a portion of an extracellular region expressed on the cell membrane surface of cancer cells, combined with an angiogenesis inhibitor, etc., was confirmed to have its strong antitumor effect in tumor-bearing animals.

Angiogenesis Inhibitor

The angiogenesis inhibitor is a drug that inhibits angiogenesis by suppressing migration or growth of vascular endothelial cells, and is preferably an anti-vascular endothelial growth factor (VEGF) inhibitor and/or an anti-vascular endothelial growth factor receptor (VEGFR) inhibitor. Specific examples of the anti-VEGF inhibitor include bevacizumab, ranibizumab, lenvatinib mesilate, and ziv-aflibercept. Specific examples of the anti-vascular endothelial growth factor receptor (VEGFR) inhibitor include ramucirumab, axitinib, regorafenib, sorafenib, sunitinib, vandetanib, pazopanib, and cabozantinib. The angiogenesis inhibitor can be preferably bevacizumab, ramucirumab, and/or axitinib.

Taxane-Based Drug

The taxane-based drug may be any compound as long as the drug exerts an antitumor effect by inhibiting microtubule depolymerization during cell division and causing excessive formation of microtubules, and thereby inhibiting cell division. Taxol, a taxane-based drug, is a tetracyclic diterpene compound which has a highly distorted structure where an oxetane ring is bonded to the C-ring of a tricyclic taxane skeleton and the B-ring is bent such that the A-ring and the C-ring face each other. This compound has a N-benzoylphenylisoserine side chain in the A-ring and has an acyl side chain bonded to a hydroxy group at position 13, which plays an important role in the antitumor activity of taxol. Other examples of the taxane-based drug include paclitaxel, docetaxel, larotaxel, nab-paclitaxel and their derivatives, which are preferably used in the present invention.

Other Drugs

The anti-CAPRIN-1 antibody, and the drug comprising an angiogenesis inhibitor and a taxane-based drug serving as active ingredients in the medicament of the present invention may be combined with an antitumor agent known in literatures, etc. Specific examples of known antitumor agents include, but are not particularly limited to, doxorubicin, daunorubicin, cyclophosphamide, methotrexate, thiotepa, busulfan, improsulfan, piposulfan, benzodopa, carboquone, meturedopa, uredopa, altretamine, triethylenemelamine, triethylenephosphoramide, triethilenethiophosphorainide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperarnicin, aclacinomycin, actinomycin, authramycin, azaserine, Neomycin, cactinomycin, carabicin, carminomycin, carzinophilin, chromomycin, dactinomycin, detorbicin, 6-diazo-5-oxo-L-norleucine, adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, dideoxyuridine, enocitabine, floxuridine, androgens such as calusterone, dromostanolone propionate, epitiostanol, tnepitiostane, testolactone, aminoglutethimide, mitotane, trilostane, frolinic acid, aceglatone, aldophosphamide glycoside, aminolevulinic acid, enluracil, amsacrine, bestrabucil, bisantrene, defofamine, demecolcine, diaziquone, elfomithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethyihydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, 6-thioguanine, mercaptopurine, oxaliplatin, vinblastine, etoposide, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, and pharmacologically acceptable (known) salts or (known) derivatives thereof.

Antitumor Effect of Present Invention

A combination of the anti-CAPRIN-1 antibody and an angiogenesis inhibitor, etc. of the present invention has cytotoxic activity in vivo. Accordingly, the antitumor effect of the present invention can be determined by examining cytotoxic activity against cancer. The cytotoxic activity can be evaluated by administering the anti-CAPRIN-1 antibody and a drug comprising an angiogenesis inhibitor, etc. to an organism having cancer, measuring the size of a tumor after the administration, and examining the size of the cancer over time. Also, the antitumor effect of the present invention can be evaluated by examining a survival rate. Alternatively, the antitumor effect of the present invention may be evaluated by examining the ability to produce cytokines or chemokines. The antitumor effect of the combination of the anti-CAPRIN-1 antibody and the angiogenesis inhibitor, etc. according to the present invention, or the antitumor effect of the combination of the anti-CAPRIN-1 antibody, the drug comprising the angiogenesis inhibitor, and one or more additional drugs according to the present invention can be further determined by examining prevention of cancer, prevention of metastasis or prevention of recurrence.

The anti-CAPRIN-1 antibody used in the present invention can be expected to have a stronger antitumor effect when having higher binding affinity for CAPRIN-1 protein on cancer cell surfaces. Association constant (affinity constant) Ka (kon/koff) is preferably at least $10^7$ $M^{-1}$, at least $10^8$ $M^{-1}$, at least $5\times10^8$ $M^{-1}$, at least $10^9$ $M^{-1}$, at least $5\times10$ $M^{-1}$, at least $10^{10}$ $M^{-1}$, at least $5\times10^{10}$ $M^{-1}$, at least $10^{11}$ $M^{-1}$, at least$5\times10^{11}$ $M^{-1}$, at least $10^{12}$ $M^{-1}$, or at least $10^{13}$ $M^{-1}$.

An ability of an anti-CAPRIN-1 antibody used in the present invention to bind to CAPRIN-1 can be specified via binding assays using, for example, ELISA. Western blot, immunofluorescence, or flowcytometry analysis.

Administration of a combination of the anti-CAPRIN-1 antibody and an angiogenesis inhibitor, etc. according to the present invention to an organism having cancer increases an antitumor effect as compared with an anti-CAPRIN-1 antibody alone, as mentioned above. The rate of increase is preferably 30% or more, more preferably 40% or more, further preferably 50% or more, still further preferably 55% or more, even further preferably 60% or more, even further preferably 65% or more, and most preferably 70% or more. The rate of increase in antitumor effect by administration of a combination of an anti-CAPRIN-1 antibody and an angiogenesis inhibitor, etc. according to the present invention with respect to administration of the anti-CAPRIN-1 antibody alone can be calculated by administering their respective effective amounts to cancer-bearing mice under the same conditions, and comparing tumor volumes on 7 days or later after the start of administration.

Medicament for Treatment and/or Prevention of Cancer

A medicament of the present invention is aimed at treating and/or preventing cancer. A cancer targeted by the medicament of the present invention is not particularly limited as long as it is cancer (cells) expressing CAPRIN-1 protein.

The term "treatment" used herein refers to treatment of cancer based on an antitumor effect mentioned above. The term "prevention" used herein refers to not only prevention of development of cancer but prevention of metastasis or recurrence of cancer.

Both the terms "tumor" and "cancer" used herein refer to malignant neoplasm, and thus they are used in an exchangeable manner.

A cancer patient that can be a target in the present invention is not particularly limited and is preferably a cancer patient with a previous history of cancer treatment with a medicament other than cancer treatment with a medicament comprising an antibody or a fragment thereof having an immunological reactivity with CAPRIN-1 protein, and an angiogenesis inhibitor or an angiogenesis inhibitor and a taxane-based drug together or separately in combination. The cancer patient also includes a patient treated with a chemotherapeutic, a molecular targeted drug, or hormone therapy in the past. Examples thereof include cancer patients who have undergone cancer treatment in accordance with "NCCN Clinical Practice Guidelines in Oncology", "ESMO Clinical Practice Guidelines" or "Clinical Practice Guideline". A cancer patient with a previous history of cancer treatment with an angiogenesis inhibitor and/or a taxane-based drug is preferred.

The patient is preferably a cancer patient who has not responded to cancer treatment with a medicament other than cancer treatment with a medicament comprising an anti-CAPRIN-1 antibody and an angiogenesis inhibitor or an angiogenesis inhibitor and a taxane-based drug together or separately in combination, and more preferably a cancer patient who has not responded to cancer treatment with an angiogenesis inhibitor and/or a taxane-based drug.

The patient is preferably a cancer patient with cancer resistant to cancer treatment with a medicament other than cancer treatment with a medicament comprising an anti-CAPRIN-1 antibody and an angiogenesis inhibitor or an angiogenesis inhibitor and a taxane-based drug together or separately in combination, and more preferably a cancer patient with cancer resistant to cancer treatment with an angiogenesis inhibitor and/or a taxane-based drug. The terms "having not responded to cancer treatment" and "resistant to cancer treatment" described herein are used to have the same meaning.

Cancer that can be a target in the present invention is any cancer as long as the cancer expresses CAPRIN-1 protein on the cell membrane surface. The cancer is preferably gastric cancer, breast cancer, kidney cancer, pancreatic cancer, colon cancer, bile duct cancer, melanoma (including post-operative melanoma), lung cancer (including non-small cell lung cancer and small cell lung cancer), renal cell carcinoma, Hodgkin's lymphoma, head and neck cancer, mesothelioma (including malignant pleural mesothelioma), colorectal cancer (e.g., MSI-high colorectal cancer), esophageal cancer, gastroesophageal junction cancer, hepatocellular carcinoma, glioblastoma, urothelial carcinoma, ovarian cancer, urinary bladder cancer, uterine cancer (including uterine cervical cancer and uterine body cancer), primary central nervous system lymphoma, primary testicular lymphoma, biliary tract cancer, brain tumor, prostate cancer, leukemia, lymphoma, liver cancer, sarcoma, fibrosarcoma, mastocytoma, adrenocortical carcinoma, Ewing's tumor, multiple myeloma, testicular cancer, thyroid cancer, basal cell carcinoma, Paget's disease or skin cancer. These cancers may be primary cancer, metastatic cancer, metastasized cancer or relapsed cancer, postoperative cancer, or unresectable cancer. Melanoma is often used to have the same meaning as malignant melanoma.

Other examples of the cancer that can be a target in the present invention include cancer resistant to known treatment methods. The resistant cancer is not particularly limited and can be cancer derived from a patient with any history of treatment. The resistant cancer is, for example, cancer that is derived from a patient with a history of treatment with 5-FU and has become resistant, has metastasized, or has relapsed after administration.

More specifically, examples of the cancer include, but are not limited to, for example, Bowen's disease, melanoma, prickle cell carcinoma, extramammary Paget's disease, mycosis fungoides, Sezary's syndrome, cutaneous T/NK-cell lymphoma, T-cell leukemia or lymphoma having a lesion only in the skin, cutaneous B-cell lvmnphoma (indolent group), cutaneous T-cell lymphatic breast adenocarcinoma, composite type breast adenocarcinoma, malignant mammary mixed tumor, intraductal papillary adenocarcinoma, lung adenocarcinoma, squamous cell cancer, small cell cancer, large cell cancer, glioma that is a tumor of neuroepithelial tissue, glioblastoma, neuroblastoma, ependymoma, neuronal tumor, embryonal neuroectodermal tumor, schwannoma, neurofibroma, meningioma, chronic lymphocytic leukemia, lymphoma, gastrointestinal lymphoma, digestive lymphoma, small-cell-to-medium-cell lymphoma, cecal cancer, ascending colon cancer, descending colon cancer, transverse colon cancer, sigmoid colon cancer, rectal cancer, ovarian epithelial cancer, germ cell tumor, interstitial cell tumor, pancreatic duct cancer, invasive pancreatic duct cancer, adenocarcinoma of pancreatic cancer, acinar cell carcinoma, adenosquamous carcinoma, giant cell tumor, intraductal papillary mucinous neoplasm, mucinous adenocarcinoma, pancreatoblastoma, pancreatic islet cell tumor, Frantz tumor, serous cystadenocarcinoma, solid pseudopapillary cancer, gastrinoma, glucagonoma, insulinoma, multiple endocrine neoplasia type-1 (Wermer syndrome), nonfunctional islet cell tumor, somatostatinoma, VIPoma, uterine cervical cancer, uterine body cancer, fibrosarcoma, osteosarcoma, joint sarcoma, Ewing sarcoma, Wilms tumor, hepatoblastoma, soft tissue sarcoma, acute leukemia, chronic leukemia, spinal cord tumor, malignant soft tissue tumor, tumors of teratoma group, head and neck cancer including hypopharynx cancer, oropharynx cancer, tongue cancer, nasopharyngeal cancer, oral cavity cancer, lip cancer, nasal and sinus cancer, and laryngeal cancer, cancer of the renal pelvis and ureter, urinary bladder cancer, urethra cancer, testicular tumor, malignant pleural mesothelioma, malignant bone tumor, uterine body cancer, and pediatric malignant solid tumor (rhabdomyosarcoma, neuroblastoma, hepatoblastoma, medulloblastoma, nephroblastoma, retinoblastoma, central nervous system germ cell tumor, and Ewing sarcoma family of tumors). The cancer also includes a palpable cancer, a subcutaneously existing cancer, an intracutaneously existing cancer, a superficial cancer, cancer existing in the dermis and cancer existing in a non-parenchymal organ, advanced cancer, which originate from the cancers described above. The cancer also includes a palpable cancer, a subcutaneously existing cancer, an intracutaneously existing cancer, a superficial cancer, cancer existing in the dermis and cancer existing in a non-parenchymal organ, which originate from the cancers described above and have metastasized and recurred.

A preferable subject (patient) that can be a target is a mammal and is, for example, a mammal including primates, pet animals, livestock animals, and sport animals. Humans, dogs and cats are particularly preferable.

A medicament of the present invention can be formulated by a method known to persons skilled in the art. For instance, the medicament of the present invention can be parenterally used in the form of a parenteral injection of: an aseptic solution in water or a pharmacologically acceptable non-water solution; or a suspension liquid. In the medicament of the present invention, an active ingredient (at least one of an anti-CAPRIN-1 antibody of the present invention, an angiogenesis inhibitor and a taxane-based drug) of each formulation or pharmaceutical composition may be combined with, for example, a pharmacologically acceptable carrier, medium, or additive, specifically, sterilized water, saline, an isotonic solution, a buffering agent (buffer solution, etc.), plant oil, oily liquid, an antioxidant, a dissolution aid, an emulsifier, a suspension, a surfactant, a stabilizer, a fragrance, an excipient, or a binder in an appropriate manner, and preferably, may be formulated by mixing with them in a unit dosage form required for a generally acceptable pharmaceutical formulation. An amount of an active ingredient in a formulation is determined such that an appropriate dosage within an indicated range can be achieved.

An aseptic composition for injection can be prepared in accordance with general formulation practice using a vehicle such as distilled water for injection. An aqueous solution for injection includes, for example, saline or isotonic solutions comprising glucose and other adjuvants such as D-sorbitol, D-mannose, D-mannitol, and sodium chloride. Such solution may be used with an appropriate dissolution aid. Such dissolution aid includes, for example, alcohols such as ethanol and polyalcohol, such as propylene glycol, polyethylene glycol, or nonionic surfactants such as polysorbate 80(TM) and HCO-60. Oily liquid includes, for example, sesame oil or soybean oil. Such oily liquid may be used in combination with a dissolution aid such as benzyl benzoate or benzyl alcohol. In addition, it may be mixed with a buffering agent such as a phosphate buffer solution or a sodium acetate buffer solution, a soothing agent such as procaine hydrochloride, a stabilizer such as benzyl alcohol or phenol, or an antioxidant. In general, a formulated injection solution is introduced into an adequate ample.

The above pharmaceutical composition is orally or parenterally administered. Preferably, it is parenterally administered. Specifically, dosage forms include injectable agents, intranasally-administered agents, transpulmonarily-administered agents, and percutaneously-administered agents. For example, injectable agents can be systemically or locally administered via intravenous injection, intramuscular injection, intraperitoneal injection, subcutaneous injection, or intratumoral injection. The percutaneously-administered agents include, for example, agents called liniments and external medicines. The external medicines include, for example, solid agents, solutions, sprays, ointments, creams, and gels.

The administration method can be appropriately determined depending on age, weight, gender, and symptoms of a patient. A single dose of a pharmaceutical composition comprising at least one of an anti-C APRIN-1 antibody, an angiogenesis inhibitor and a taxane-based drug can be selected within a range of, for example, 0.0001 mg to 1000 mg per kg of body weight as an amount of each active ingredient. Alternatively, the dose of each active ingredient can be selected within a range of, for example, 0.001 to 100000 mg per patient's body or 0.1 mg to 300 mg or 1 mg to 30 mg per kg of patient's body weight; however, it is not necessarily limited thereto. The dose and the administration method are changed depending on patient age, weight, gender, and symptoms. However, persons skilled in the art can appropriately select the dose and the method.

Administration Method

Treatment and/or prevention of cancer with a medicament for treatment and/or prevention of cancer of the present invention includes various modes, in addition to administration as a medicament mentioned above. For example, respective active ingredients in a medicament of the present invention can be administered simultaneously, concurrently, or individually in a staggered manner. As a specific example, active ingredients can be administered within a time interval up to approximately 3 weeks, i.e., the second active ingredient can be administered from immediately up to approximately 3 weeks after administration of the first active ingredient, and the third active ingredient can be administered from immediately up to approximately 3 weeks after administration of the second active ingredient. These administrations may be carried out subsequently to a surgical procedure, or a surgical procedure may be carried out between the administrations of the first and second drugs or between the administrations of the second and third drugs. In addition, the medicament for treatment and/or prevention of cancer of the present invention may be administered according to a plurality of administration cycles. For example, in the case of carrying out simultaneous administration of respective active ingredients in a medicament for treatment and/or prevention of cancer of the present invention, a pharmaceutical composition comprising the active ingredients of the present invention (an anti-CAPRIN-1 antibody and an angiogenesis inhibitor or an angiogenesis inhibitor and a taxane-based drug) is administered for approximately 2 days to approximately 3 weeks as one cycle. Then, this treatment cycle may be repeated, if necessary, according to the judgment of a physician in charge. Likewise, in the case of scheduling a formulation in a staggered manner, respective administration periods of individual agents are adjusted so as to span the same period. The interval between cycles can vary from 0 to 2 months. Respective doses of the active ingredients in the medicament for treatment and/or prevention of cancer of the present invention can be set in the same way as in the respective doses of the active ingredients in the pharmaceutical composition described above.

Pharmaceutical Kit

A medicament for treatment and/or prevention of cancer of the present invention may be in the form of a pharmaceutical kit. The pharmaceutical kit is a package for using active ingredients in the form of separate pharmaceutical compositions (formulations) in a method for treating and/or preventing cancer. The package may comprise an instruction for administering each of the active ingredients. The respective active ingredients in the pharmaceutical compositions for treatment and/or prevention of cancer contained in the pharmaceutical kit can be in the form of pharmaceutical compositions each formulated as described above such that the active ingredients can be administered together or separately. Further, the pharmaceutical kit comprises active ingredients in amounts sufficient for one or more doses such that the active ingredients can be administered according to the administration method described above.

Treatment and/or Prevention Method

On the basis of the contents specifically described above, the present invention provides a method for treating and/or preventing cancer, comprising administering the medicament of the present invention, or the anti-CAPRIN-1 antibody of the present invention and an angiogenesis inhibitor or an angiogenesis inhibitor and a taxane-based drug to a subject (patient). The present invention further provides, for example, a method for treating and/or preventing cancer, comprising administering the medicament of the present invention, etc. to a subject (patient) haying cancer or suspected of having cancer. In the method of the present invention, in addition to the anti-CAPRIN-1 antibody of the present invention and the angiogenesis inhibitor or the angiogenesis inhibitor and the taxane-based drug, other antitumor agents (known antitumor agents, etc.) may be administered to the subject (patient). In this embodiment, the anti-CAPRIN-1 antibody of the present invention (the antibody or the fragment thereof), the angiogenesis inhibitor or the angiogenesis inhibitor and the taxane-based drug, and optionally, an antitumor agent contained in the medicament can be administered simultaneously or separately to the subject (patient).

EXAMPLES

The present invention is hereafter described in detail with reference to the following examples, although the scope of the present invention is not limited thereto.

Example 1

Production of Anti-CAPRIN-1 Antibody

Anti-CAPRIN-1 antibodies having an immunological reactivity with CAPRIN-1 protein, used in the present invention were produced as described below for use.

Polyclonal Antibody

One (1) mgr of a human CAPRIN-1 recombinant protein (SEQ ID NO: 2) produced according to Example 3 of WO2010/016526 was mixed with an incomplete Freund's adjuvant (IFA) solution in an amount equivalent to the recombinant protein. The mixture was subcutaneously administered to a rabbit 4 times every 2 weeks. Subsequently, blood was collected, so that an antiserum containing a polyclonal antibody was obtained. Furthermore, the antiserum was purified using a protein G carrier (GE Healthcare Bio-Sciences) and replaced with PBS(-) and then a polyclonal antibody against CAPRIN-1 protein (anti-CAPRIN-1 polyclonal antibody #1) was obtained.

Monoclonal Antibody

One hundred (100) μg of a human CAPRIN-1 recombinant protein produced according to Example 3 of WO2010/016526 was mixed with a MPL+TDM adjuvant (Sigma) in an amount equivalent to that of the recombinant protein, The mixture was used as an antigen solution per mouse. The antigen solution was administered intraperitoneally to 6-week-old Balb/c mice (Japan SLC Inc.) and then further administered 3 times and 24 times every week for completion of immunization. A spleen was removed on day 3 after the final immunization and then ground between two sterilized glass slides. Spleen cells were obtained by washing with PBS (-) (Nissui Pharmaceutical), centrifuging at 1500 rpm for 10 minutes, and removing supernatant, therein these were repeated 3 times. The obtained spleen cells were mixed with mouse myeloma cell SP2/0 (purchased from ATCC) at a ratio of 10:1. The PEG solution prepared by mixing 200 μl of RPMI1640 medium containing 10% FBS heated at 37° C. and 800 μl of PEG1500 (Boehringer) was added to the cells. The solution was incubated for 5 minutes for cell fusion. Centrifugation was performed at 1700 rpm for 5 minutes to remove supernatants. Cells were suspended in 150 ml of RPMI1640 medium (HAT selective medium) containing 15% FBS, to which 2% equivalent of HAT solution (Gibco) had been added and then seeded onto fifteen 96-well plates (Nunc) at 100 μl per well. Cells were cultured for 7 days under conditions of 37° C. and 5% $CO_2$, so that hybridomas resulting from fusion of spleen cells to myeloma cells were obtained. Hybridomas were selected using binding affinity to CAPRIN-1 protein of the antibody produced by the prepared hybridomas as an indicator. The CAPRIN-1 protein solution (1 μg/ml) was added at 100 μl per well of 96-well plates and then incubated at 4° C. for 18 hours. After each well was washed 3 times with PBS-T, 0.5% Bovine Serum Albumin (BSA) solution (Sigma) was added at 400 μl per well, and then the plates were incubated at room temperature for 3 hours. The solution was removed and then each well was washed 3 times with 400 μl of PBS-T. Each culture supernatant of the hybridomas obtained above was added at 100 μl per well and then incubated at room temperature for 2 hours. After each well was washed 3 times with PBS-T, an HRP-labeled anti-mouse IgG (H+L) antibody (Invitrogen) diluted 5000-fold with PBS was added at 100 μl per well and then incubated at room temperature for 1 hour. After each well was washed 3 times with PBS-T, a TMB substrate solution (Thermo) was added at 100 μl per well and then incubated for 15-30 minutes, so that a color reaction was performed. After color development, 1 N sulfuric acid was added at 100 μl per well to stop the reaction. Absorbance at 450 nm and absorbance at 595 nm were measured using an absorption spectrometer. As a result, a plurality of hybridomas producing antibodies with high absorbances were selected. The selected hybridomas were added at 0.5 hybridomas per well of 96-well plates and then cultured. After 1 week, hybridomas forming a single colony in wells were observed. Cells in these wells were further cultured. Hybridomas were selected using binding affinity to CAPRIN-1 protein of the antibody produced by cloned hybridomas as an indicator. The CAPRIN-1 protein solution (1 μg/ml) was added at 100 μl per well of 96-well plates and then incubated at 4° C. for 18 hours. Each well was washed 3 times with PBS-T, a 0.5% BSA solution was added at 400 μl per well, and then incubated at room temperature for 3 hours. The solution was removed and then each well was washed 3 times with 400 μl of PBS-T. Each culture supernatant of the hybridomas obtained above was added at 100 μl per well and then incubated at room temperature for 2 hours. Each well was washed 3 times with PBS-T, an HRP-labeled anti-mouse IgG (H+L) antibody (Invitrogen) diluted 5000-fold with PBS was added at 100 μl per well and then incubated at room temperature for 1 hour. Each well was washed 3 times with PBS-T, a TMB substrate solution (Thermo) was added at 100 μl per well and then incubated for 15-30 minutes, so that a color reaction was performed. After color development, 1 N sulfuric acid was added at 100 μl per well to stop the reaction. Absorbance at 450 nm and absorbance at 595 nm were measured using an absorption spectrometer. As a result, a plurality of mouse monoclonal antibodies exerting reactivity with CAPRIN-1 protein were obtained.

Reactivity of each monoclonal antibody with human cancer cells confirmed to express CAPRIN-1 protein on the cell membrane surface was further confirmed by flow cytometry. A mouse IgG control antibody exhibiting no reactivity with the cancer cells was used as a negative control. As a result of confirmation, several monoclonal antibodies were obtained which had stronger fluorescence intensity against the cancer cells than that of the mouse IgG control antibody and reacted strongly with the cell membrane surface of the cancer cells expressing CAPRIN-1 on the cell membrane surface. From among them, a monoclonal antibody against CAPRIN-1 described in WO2013/125630, which was an antibody comprising the amino acid sequence of a heavy-chain variable region shown in SEQ ID NO: 114 and the amino acid sequence of a light-chain variable region shown in SEQ ID NO: 115, was selected as a monoclonal antibody exhibiting reactivity with CAPRIN-1 protein.

CDR1 to CDR3 of the heavy-chain variable region of the antibody selected were identified. A nucleotide sequence was designed so as to be able to express a heavy-chain variable region in which framework regions comprising a human antibody sequence. This nucleotide sequence was inserted to a vector for mammalian expression having an insert of a human IgG1 heavy-chain constant region. Likewise, CDR1 to CDR3 of the light-chain variable region were identified. A nucleotide sequence was designed so as to be able to express a light-chain variable region in which framework regions comprised a human antibody sequence. This nucleotide sequence was inserted to a vector for mammalian expression having an insert of a human IgG1 light-chain constant region. These two recombinant expression vectors were introduced to mammalian cells according to a general method and then a culture supernatant containing humanized monoclonal antibody #1 (humanized antibody #1) against CAPRIN-1 was obtained.

The obtained culture supernatant containing the obtained humanized anti-CAPRIN-1 monoclonal antibody #1 was purified using Hitrap Protein A Sepharose FF (GE Healthcare Bio-Sciences) according to a general method, replaced with PBS(-), and filtered through a 0.22 μm filter (Millipore) for preparation of the filtrate.

The specific reactivity of the anti-CAPRIN-1 antibody to CAPRIN-1 protein was detected and confirmed by ELISA using CAPRIN-1 protein immobilized on a plate.

The reactivity of the anti-CAPRIN-1 antibody with cancer cells without permeation treatment of cell membrane was examined by flow cytometry to confirm that a portion of CAPRIN-1 was expressed on the cell membrane surface of cancer cells as shown in Examples given below.

It was confirmed by flow cytometry that, against all of breast cancer cells (BT-474), colon cancer cells (HT-29), lung cancer cells (QG56 and H1650), gastric cancer cells (NCI-N87), uterine cancer cells (HEC-1-A), prostate cancer cells (22Rv1), pancreatic cancer cells (Panc10.5), liver cancer cells (Hep3B), ovarian cancer cells (SKOV3), kidney cancer cells (Caki-2), brain tumor cells (U-87MG), urinary bladder cancer cells (T24), esophageal cancer cells (OE33), leukemia cells (OCI-AIM5), lymphoma cells (Ramos), gallbladder cancer cells (TGBC14TKB), fibrosarcoma cells (HT-1080), and melanoma cells (G-361), which are human cancer cells confirmed to express CAPRIN-1 gene, and mouse kidney cancer cells (Renca) and mouse breast cancer cells (4T1) confirmed to express CAPRIN-1 gene, the humanized antibody #1 had stronger fluorescence intensity than that of a human IgG control antibody and rabbit IgG antibody serving as negative controls exhibiting no reactivity with the cancer cells and reacted strongly with the cell membrane surface of the cancer cells expressing CAPRIN-1. 101451

Likewise, it was confirmed that the anti-CAPRIN-1 antibodies described in WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125640, WO2013/147169, WO2013/147176 and WO2015/020212 also reacted strongly with the cell membrane surface of the cancer cells.

Example 2

Antitumor Effect of Combination of Anti-CAPRIN-1 Antibody and Angiogenesis Inhibitor in Human Cancer Cell-Bearing Mouse Model Next, in vivo antitumor effect in cancer-bearing mouse was evaluated by administering a combination of the anti-CAPRIN-1 antibody (anti-CAPRIN-1 humanized antibody #1) produced in Example 1, and an angiogenesis inhibitor bevacizumab (anti-VEGF antibody).

Specifically, the antitumor effect of the combination of the anti-CAPRIN-1 antibody, and bevacizumab according to the present invention was studied using NOD-SCID mice in which human-derived cancer cells expressing CAPRIN-1 protein were subcutaneously transplanted. Human breast cancer cells BT474 were subcutaneously transplanted at $2\times10^7$ cells per mouse as a mixture with Matrigel (Sigma) and allowed to grow until a tumor became approximately 100 $mm^3$ to prepare cancer-bearing mice. The cancer cells BT474 express CAPRIN-1 protein on the cell membrane surface, and the anti-CAPRIN-1 antibodies produced in Example 1 were confirmed to react with a portion of CAPRIN-1 present on the cell membrane surfaces. Each anti-CAPRIN-1 antibody produced in Example 1 was administered at 10 mg/kg once a week to the tail veins of five cancer-bearing mice described above. To these mice, administration of bevacizumab was started at 1.25 mg/kg once a week simultaneously with the initial administration of the anti-CAPRIN-1 antibody.

For a comparative control group, the same dose of the same anti-CAPRIN-1 antibody as above was administered once a week to cancer-bearing mice. For another comparative control group, bevacizumab was administered at the same administration intervals and dose as above to other individuals of cancer-bearing mice. Cancer-bearing mice in a non-treatment group were used as negative controls. After the start of administration, the sizes of cancers in the cancer-bearing mice were measured over time using calipers. Tumor volumes were calculated according to a standard method using a calculation expression: (Length of the major axis of the tumor)×(Length of the minor axis of the tumor)$^2$×0.5.

As a result of evaluation, the tumor volume was 52% in the group given the anti-CAPRIN-1 humanized antibody #1 produced in Example 1, and approximately 91% in the group given bevacizumab as the comparative control groups on day 41 after cancer bearing, when the tumor volume of the negative control was defined as 100%. On the other hand, the tumor volume was approximately 14% in the group given the combination of the humanized antibody #1 produced in Example 1 and bevacizumab, and was thus reduced from that at the start of administration.

The results of this evaluation demonstrated that administration of a combination of the anti-CAPRIN-1 antibody and the angiogenesis inhibitory antibody bevacizumab has a much stronger antitumor effect than that of administration of the anti-CAPRIN-1 antibody alone or the administration of bevacizumab alone.

Likewise, in vivo antitumor effect in cancer-bearing mouse was evaluated by administering a combination of the anti-CAPRIN-1 antibody (anti-CAPRIN-1 humanized antibody #1) produced in Example 1, and an anti-vascular endothelial growth factor receptor (VEGFR) inhibitor.

Specifically, the antitumor effect of the combination of the anti-CAPRIN-1 antibody and axitinib according to the present invention was studied using NOG mice in which human-derived cancer cells expressing CAPRIN-1 protein were subcutaneously transplanted. Human breast cancer cells BT474 were subcutaneously transplanted at $2\times10^7$ cells per mouse as a mixture with Matrigel and allowed to grow until a tumor became approximately 100 $mm^3$ to prepare cancer-bearing mice. Each anti-CAPRIN-1 antibody produced in Example 1 was administered at 10 mg/kg once a week to the tail veins of five cancer-bearing mice described above. To these mice, administration of axitinib was started simultaneously with the initial administration of the anti-CAPRIN-1 antibody, and the administration was performed at 5 or 25 mg/kg twice a day for 9 days and then once a day for 15 days.

For a comparative control group, the same dose of the same anti-CAPRIN-1 antibody as above was administered once a week to cancer-bearing mice. For another comparative control group, axitinib was administered at the same administration intervals and dose as above to other individuals of cancer-bearing mice. Cancer-bearing mice in a non-treatment group were used as negative controls. After the start of administration, the sizes of cancers in the cancer-bearing mice were measured over time using calipers. Tumor volumes were calculated according to a standard method using a calculation expression: (Length of the major axis of the tumor)×(Length of the minor axis of the tumor)$^2$×0.5.

As a result of evaluation, the tumor volume was 40% in the group given the anti-CAPRIN-1 humanized antibody #1 produced in Example 1, 39% in the group given 5 mg/kg axitinib, and 27% in the group given 25 mg/kg axitinib as the comparative control groups on day 63 after cancer bearing, when the tumor volume of the negative control was defined as 100%. On the other hand, the tumor volume was 18% in the group given the combination of the humanized antibody #1 produced in Example 1 and 5 mg/kg axitinib, and 8% in the group given the combination of this antibody and 25 mg/kg axitinib, and was thus reduced from that at the start of administration.

The results of this evaluation demonstrated that administration of a combination of the anti-CAPRIN-1 antibody and the angiogenesis inhibitor axitinib has a much stronger antitumor effect than that of administration of the anti-CAPRIN-1 antibody alone or the administration of axitinib alone.

Example 3

Antitumor Effect of Combination of Anti-CAPRIN-1 Antibody, and Angiogenesis Inhibitor and Taxane-Based Drug Six cases of gastric cancer patients who had a previous history of existing first-line treatment (cisplatin, 5-FU (fluorouracil), levofolinate, trastuzumab, capecitabine, taxotere, FOLFOX (combination therapy of fluorouracil, folinic acid (levofolinate) and oxaliplatin), FOLFIRI (combination therapy of fluorouracil, folinic acid (levofolinate) and irinotecan), docetaxel or oxaliplatin), etc., and had not received sufficient drug efficacy from the treatment were given a combination of "TRK-950" (anti-CAPRIN-1 antibody under clinical trial as a therapeutic agent for cancer) at a dose of 10 mg/kg in addition to a taxane-based drug paclitaxel and an angiogenesis inhibitor anti-VEGFR antibody (ramucirumab). As a result of evaluation of the tumor sizes of metastatic foci in each patient by CT examination, reduction in total tumor size was confirmed in all the patients after the start of administration (approximately 11 to 44% reduction) and partial response was obtained as drug efficacy in two cases. Thus, treatment of cancer patients with a combination of an anti-CAPRIN-1 antibody, an angiogenesis inhibitor and a taxane-based drug was found to exert very strong drug efficacy which cannot be obtained in existing standard treatment.

All publications, patents and patent applications cited herein are incorporated herein by reference in their entirety.

The invention claimed is:

1. A medicament for treatment of cancer, comprising (i) an antibody or a fragment thereof having an immunological reactivity with CAPRIN-1 protein, (ii) ramucirumab, and (iii) paclitaxel, nab-paclitaxel, or a combination of paclitaxel and nab-paclitaxel, wherein the cancer is cancer expressing CAPRIN-1 protein on a cell membrane surface.

2. The medicament according to claim 1, wherein the antibody or the fragment thereof has an immunological reactivity with CAPRIN-1 protein having an amino acid sequence represented by any one of the even numbered SEQ ID NOs: 2 to 30.

3. The medicament according to claim 1, wherein the antibody or the fragment thereof has an immunological reactivity with an extracellular region of a CAPRIN-1 protein present on a cancer cell surface.

4. The medicament according to claim 1, wherein the antibody or the fragment thereof has an immunological reactivity with a partial polypeptide of CAPRIN-1 protein, the partial polypeptide having an amino acid sequence represented by any one of SEQ ID NOs: 31 to 35, 296 to 299, 308 and 309.

5. The medicament according to claim 1, wherein the antibody is a monoclonal antibody or a polyclonal antibody.

6. The medicament according to claim 1, wherein the antibody or a fragment thereof is any one of the following (A) to (M):

(A) an antibody or a fragment thereof comprising a heavy-chain variable region comprising complementarity determining regions of SEQ ID NOs: 36, 37 and 38 (CDR1, CDR2 and CDR3, respectively) and a light-chain variable region comprising complementarity determining regions of SEQ ID NOs: 40, 41 and 42 (CDR1, CDR2 and CDR3, respectively), and having an immunological reactivity with CAPRIN-1 protein;

(B) an antibody or a fragment thereof comprising a heavy-chain variable region comprising complementarity determining regions of SEQ ID NOs: 44, 45 and 46 (CDR1, CDR2 and CDR3, respectively) and a light-chain variable region comprising complementarity determining regions of SEQ ID NOs: 48, 49 and 50 (CDR1, CDR2 and CDR3, respectively), and having an immunological reactivity with CAPRIN-1 protein;

(C) an antibody or a fragment thereof comprising a heavy-chain variable region comprising complementarity determining regions of SEQ ID NOs: 52, 53 and 54 (CDR1, CDR2 and CDR3, respectively) and a light-chain variable region comprising complementarity determining regions of SEQ ID NOs: 56, 57 and 58 (CDR1, CDR2 and CDR3, respectively), and having an immunological reactivity with CAPRIN-1 protein;

(D) an antibody or a fragment thereof comprising a heavy-chain variable region comprising complementarity determining regions of SEQ ID NOs: 60, 61 and 62 (CDR1, CDR2 and CDR3, respectively) and a light-chain variable region comprising complementarity determining regions of SEQ ID NOs: 64, 65 and 66 (CDR1, CDR2 and CDR3, respectively), and having an immunological reactivity with CAPRIN-1 protein;

(E) an antibody or a fragment thereof comprising a heavy-chain variable region comprising complementarity determining regions of SEQ ID NOs: 170, 171 and 172 (CDR1, CDR2 and CDR3, respectively) and a light-chain variable region comprising complementarity determining regions of SEQ ID NOs: 173, 174 and 175 (CDR1, CDR2 and CDR3, respectively), and having an immunological reactivity with CAPRIN-1 protein;

(F) an antibody or a fragment thereof comprising a heavy-chain variable region comprising complementarity determining regions of SEQ ID NOs: 176, 177 and 178 (CDR1, CDR2 and CDR3, respectively) and a light-chain variable region comprising complementarity determining regions of SEQ ID NOs: 179, 180 and 181 (CDR1, CDR2 and CDR3, respectively), and having an immunological reactivity with CAPRIN-1 protein;

(G) an antibody or a fragment thereof comprising a heavy-chain variable region comprising complementarity determining regions of SEQ ID NOs: 182, 183 and 184 (CDR1, CDR2 and CDR3, respectively) and a light-chain variable region comprising complementarity determining regions of SEQ ID NOs: 185, 186 and 187 (CDR1, CDR2 and CDR3, respectively), and having an immunological reactivity with CAPRIN-1 protein;

(H) an antibody or a fragment thereof comprising a heavy-chain variable region comprising complementarity determining regions of SEQ ID NOs: 188, 189 and 190 (CDR1, CDR2 and CDR3, respectively) and a light-chain variable region comprising complementarity determining regions of SEQ ID NOs: 191, 192 and 193 (CDR1, CDR2 and CDR3, respectively), and having an immunological reactivity with CAPRIN-1 protein;

(I) an antibody or a fragment thereof comprising a heavy-chain variable region comprising complementarity determining regions of SEQ ID NOs: 146, 147 and 148 (CDR1, CDR2 and CDR3, respectively) and a light-chain variable region comprising complementarity determining regions of SEQ ID NOs: 149, 150 and 151 (CDR1, CDR2 and CDR3, respectively), and having an immunological reactivity with CAPRIN-1 protein;

(J) an antibody or a fragment thereof comprising a heavy-chain variable region comprising complementarity determining regions of SEQ ID NOs: 272, 273 and 274 (CDR1, CDR2 and CDR3, respectively) and a light-chain variable region comprising complementarity determining regions of SEQ ID NOs: 275, 276 and 277 (CDR1, CDR2 and CDR3, respectively), and having an immunological reactivity with CAPRIN-1 protein;

(K) an antibody or a fragment thereof comprising a heavy-chain variable region comprising complementarity determining regions of SEQ ID NOs: 290, 291 and 292 (CDR1, CDR2 and CDR3, respectively) and a light-chain variable region comprising complementarity determining regions of SEQ ID NOs: 293, 294 and 295 (CDR1, CDR2 and CDR3, respectively), and having an immunological reactivity with CAPRIN-1 protein;

(L) an antibody or a fragment thereof comprising a heavy-chain variable region comprising complementarity determining regions of SEQ ID NOs: 300, 301 and 302 (CDR1, CDR2 and CDR3, respectively) and a light-chain variable region comprising complementarity determining regions of SEQ ID NOs: 304, 305 and 306 (CDR1, CDR2 and CDR3, respectively), and having an immunological reactivity with CAPRIN-1 protein; and (M) an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with CAPRIN-1 protein.

7. The medicament according to claim 1, wherein the antibody or the fragment thereof is any one of the following (a) to (al):

(a) an antibody or a fragment thereof comprising a heavy-chain variable region comprising the amino acid sequence of SEQ ID NO: 39 and a light-chain variable region comprising the amino acid sequence of SEQ ID NO: 43;

(b) an antibody or a fragment thereof comprising a heavy-chain variable region comprising the amino acid sequence of SEQ ID NO: 47 and a light-chain variable region comprising the amino acid sequence of SEQ ID NO: 51;

(c) an antibody or a fragment thereof comprising a heavy-chain variable region comprising the amino acid sequence of SEQ ID NO: 55 and a light-chain variable region comprising the amino acid sequence of SEQ ID NO: 59;

(d) an antibody or a fragment thereof comprising a heavy-chain variable region comprising the amino acid sequence of SEQ ID NO: 63 and a light-chain variable region comprising the amino acid sequence of SEQ ID NO: 67;

(e) an antibody or a fragment thereof comprising a heavy-chain variable region comprising the amino acid sequence of SEQ ID NO: 68 and a light-chain variable region comprising the amino acid sequence of SEQ ID NO: 69;

(f) an antibody or a fragment thereof comprising a heavy-chain variable region comprising the amino acid sequence of SEQ ID NO: 70 and a light-chain variable region comprising the amino acid sequence of SEQ ID NO: 71;

(g) an antibody or a fragment thereof comprising a heavy-chain variable region comprising the amino acid sequence of SEQ ID NO: 72 and a light-chain variable region comprising the amino acid sequence of SEQ ID NO: 73;

(h) an antibody or a fragment thereof comprising a heavy-chain variable region comprising the amino acid sequence of SEQ ID NO: 74 and a light-chain variable region comprising the amino acid sequence of SEQ ID NO: 75;

(i) an antibody or a fragment thereof comprising a heavy-chain variable region comprising the amino acid sequence of SEQ ID NO: 76 and a light-chain variable region comprising the amino acid sequence of SEQ ID NO: 77;

(j) an antibody or a fragment thereof comprising a heavy-chain variable region comprising the amino acid sequence of SEQ ID NO: 78 and a light-chain variable region comprising the amino acid sequence of SEQ ID NO: 79;

(k) an antibody or a fragment thereof comprising a heavy-chain variable region comprising the amino acid sequence of SEQ ID NO: 80 and a light-chain variable region comprising the amino acid sequence of SEQ ID NO: 81;

(l) an antibody or a fragment thereof comprising a heavy-chain variable region comprising the amino acid sequence of SEQ ID NO: 82 and a light-chain variable region comprising the amino acid sequence of SEQ ID NO: 83;

(m) an antibody or a fragment thereof comprising a heavy-chain variable region comprising the amino acid sequence of SEQ ID NO: 84 and a light-chain variable region comprising the amino acid sequence of SEQ ID NO: 85;

(n) an antibody or a fragment thereof comprising a heavy-chain variable region comprising the amino acid sequence of SEQ ID NO: 86 and a light-chain variable region comprising the amino acid sequence of SEQ ID NO: 87;

(o) an antibody or a fragment thereof comprising a heavy-chain variable region comprising the amino acid sequence of SEQ ID NO: 88 and a light-chain variable region comprising the amino acid sequence of SEQ ID NO: 89;

(p) an antibody or a fragment thereof comprising a heavy-chain variable region comprising the amino acid sequence of SEQ ID NO: 90 and a light-chain variable region comprising the amino acid sequence of SEQ ID NO: 91;

(q) an antibody or a fragment thereof comprising a heavy-chain variable region comprising the amino acid sequence of SEQ ID NO: 92 and a light-chain variable region comprising the amino acid sequence of SEQ ID NO: 93;

(r) an antibody or a fragment thereof comprising a heavy-chain variable region comprising the amino acid sequence of SEQ ID NO: 94 and a light-chain variable region comprising the amino acid sequence of SEQ ID NO: 95;

(s) an antibody or a fragment thereof comprising a heavy-chain variable region comprising the amino acid sequence of SEQ ID NO: 96 and a light-chain variable region comprising the amino acid sequence of SEQ ID NO: 97;

(t) an antibody or a fragment thereof comprising a heavy-chain variable region comprising the amino acid sequence of SEQ ID NO: 98 and a light-chain variable region comprising the amino acid sequence of SEQ ID NO: 99;

(u) an antibody or a fragment thereof comprising a heavy-chain variable region comprising the amino acid sequence of SEQ ID NO: 100 and a light-chain variable region comprising the amino acid sequence of SEQ ID NO: 101;

(v) an antibody or a fragment thereof comprising a heavy-chain variable region comprising the amino acid sequence of SEQ ID NO: 102 and a light-chain variable region comprising the amino acid sequence of SEQ ID NO: 103;

(w) an antibody or a fragment thereof comprising a heavy-chain variable region comprising the amino acid sequence of SEQ ID NO: 104 and a light-chain variable region comprising the amino acid sequence of SEQ ID NO: 105;

(x) an antibody or a fragment thereof comprising a heavy-chain variable region comprising the amino acid sequence of SEQ ID NO: 106 and a light-chain variable region comprising the amino acid sequence of SEQ ID NO: 107;

(y) an antibody or a fragment thereof comprising a heavy-chain variable region comprising the amino acid sequence of SEQ ID NO: 108 and a light-chain variable region comprising the amino acid sequence of SEQ ID NO: 109;

(z) an antibody or a fragment thereof comprising a heavy-chain variable region comprising the amino acid sequence of SEQ ID NO: 110 and a light-chain variable region comprising the amino acid sequence of SEQ ID NO: 111;

(aa) an antibody or a fragment thereof comprising a heavy-chain variable region comprising the amino acid sequence of SEQ ID NO: 112 and a light-chain variable region comprising the amino acid sequence of SEQ ID NO: 113;

(ab) an antibody or a fragment thereof comprising a heavy-chain variable region comprising the amino acid sequence of SEQ ID NO: 114 and a light-chain variable region comprising the amino acid sequence of SEQ ID NO: 115;

(ac) an antibody or a fragment thereof comprising a heavy-chain variable region comprising the amino acid sequence of SEQ ID NO: 116 and a light-chain variable region comprising the amino acid sequence of SEQ ID NO: 117;

(ad) an antibody or a fragment thereof comprising a heavy-chain variable region comprising the amino acid sequence of SEQ ID NO: 118 and a light-chain variable region comprising the amino acid sequence of SEQ ID NO: 119;

(ae) an antibody or a fragment thereof comprising a heavy-chain variable region comprising the amino acid sequence of SEQ ID NO: 120 and a light-chain variable region comprising the amino acid sequence of SEQ ID NO: 121;

(af) an antibody or a fragment thereof comprising a heavy-chain variable region comprising the amino acid sequence of SEQ ID NO: 122 and a light-chain variable region comprising the amino acid sequence of SEQ ID NO: 123;

(ag) an antibody or a fragment thereof comprising a heavy-chain variable region comprising the amino acid sequence of SEQ ID NO: 124 and a light-chain variable region comprising the amino acid sequence of SEQ ID NO: 125;

(ah) an antibody or a fragment thereof comprising a heavy-chain variable region comprising the amino acid sequence of SEQ ID NO: 126 and a light-chain variable region comprising the amino acid sequence of SEQ ID NO: 127;

(ai) an antibody or a fragment thereof comprising a heavy-chain variable region comprising the amino acid sequence of SEQ ID NO: 128 and a light-chain variable region comprising the amino acid sequence of SEQ ID NO: 129;

(aj) an antibody or a fragment thereof comprising a heavy-chain variable region comprising the amino acid sequence of SEQ ID NO: 130 and a light-chain variable region comprising the amino acid sequence of SEQ ID NO: 131;

(ak) an antibody or a fragment thereof comprising a heavy-chain variable region comprising the amino acid sequence of SEQ ID NO: 132 and a light-chain variable region comprising the amino acid sequence of SEQ ID NO: 133; and (al) an antibody or a fragment thereof comprising a heavy-chain variable region comprising the amino acid sequence of SEQ ID NO: 303 and a light-chain variable region comprising the amino acid sequence of SEQ ID NO: 307.

8. The medicament according to claim 1, wherein the antibody is a human antibody, a humanized antibody, a chimeric antibody or a single chain antibody.

9. An agent for increasing drug efficacy of a pharmaceutical composition for treatment of cancer comprising (i) an antibody or a fragment thereof having an immunological reactivity with CAPRIN-1 protein as an active ingredient, wherein the agent further comprises (ii) ramucirumab and (iii) paclitaxel, nab-paclitaxel, or a combination of paclitaxel and nab-paclitaxel, as active ingredients, wherein the cancer is cancer expressing CAPRIN-1 protein on a cell membrane surface.

10. A method for treating cancer, comprising administering (i) an antibody or a fragment thereof having an immunological reactivity with CAPRIN-1 protein, (ii) ramucirumab, and (iii) paclitaxel, nab-paclitaxel, or a combination of paclitaxel and nab-paclitaxel, to a subject in need thereof, wherein the cancer is cancer expressing CAPRIN-1 protein on a cell membrane surface.

11. The method according to claim 10, wherein the cancer is cancer in a cancer patient who has not responded to cancer treatment with a medicament other than cancer treatment with a medicament comprising an antibody or a fragment thereof having an immunological reactivity with CAPRIN-1 protein, an angiogenesis inhibitor, and a taxane-based drug together or separately in combination.

12. The method according to claim 10, wherein the cancer is gastric cancer, breast cancer, kidney cancer, pancreatic cancer, colon cancer, bile duct cancer, melanoma, lung cancer, renal cell carcinoma, Hodgkin's lymphoma, head and neck cancer, mesothelioma, colorectal cancer, esophageal cancer, gastroesophageal junction cancer, hepatocellular carcinoma, glioblastoma, urothelial carcinoma, ovarian cancer, urinary bladder cancer, uterine cancer, primary central nervous system lymphoma, primary testicular lymphoma, biliary tract cancer, brain tumor, prostate cancer, leukemia, lymphoma, liver cancer, sarcoma, fibrosarcoma, mastocytoma, adrenocortical carcinoma, Ewing's tumor, multiple myeloma, testicular cancer, thyroid cancer, basal cell carcinoma, Paget's disease or skin cancer.

* * * * *

SEQUENCE LISTING

```
<160> NUMBER OF SEQ ID NOS: 309

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 1

cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc       327
```

-continued

```
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac      375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat      471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa      615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350
```

-continued

```
gat ccc ctt gtg aga aga cag cga gta caa gac ctt atg gca caa atg      1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat      1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca      1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa      1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca      1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa      1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460

cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670
```

```
cag cag aat ttc aag cga ggc tct ggg cag agt gga cca cgg gga gcc     2247
Gln Gln Asn Phe Lys Arg Gly Ser Gly Gln Ser Gly Pro Arg Gly Ala
                675                 680                 685

cca cga ggt cgt gga ggg ccc cca aga ccc aac aga ggg atg ccg caa     2295
Pro Arg Gly Arg Gly Gly Pro Pro Arg Pro Asn Arg Gly Met Pro Gln
            690                 695                 700

atg aac act cag caa gtg aat taa tctgattcac aggattatgt ttaatcgcca    2349
Met Asn Thr Gln Gln Val Asn
        705

aaaacacact ggccagtgta ccataaatatg ttaccagaag agttattatc tatttgttct   2409

ccctttcagg aaacttattg taaagggact gttttcatcc cataaagaca ggactacaat   2469

tgtcagcttt ctattacctg gatatggaag gaaactattt ttactctgca tgttctgtcc   2529

taagcgtcat cttgagcctt gcacatgata ctcagattcc tcacccttgc ttaggagtaa   2589

aacaatatac tttacagggt gataataatc tccatagtta tttgaagtgg cttgaaaaag   2649

gcaagattga cttttatgac attggataaa atctacaaat cagccctcga gttattcaat   2709

gataactgac aaactaaatt atttccctag aaaggaagat gaaaggagtg gagtgtggtt   2769

tggcagaaca actgcatttc acagcttttc cagttaaatt ggagcactga acgttcagat   2829

gcataccaaa ttatgcatgg gtcctaatca cacatataag gctggctacc agctttgaca   2889

cagcactgtt catctggcca aacaactgtg gttaaaaaca catgtaaaat gctttttaac   2949

agctgatact gtataagaca aagccaagat gcaaaattag gctttgattg gcactttttg   3009

aaaaatatgc aacaaatatg ggatgtaatc cggatggccg cttctgtact taatgtgaaa   3069

tatttagata cctttttgaa cacttaacag tttctttgag acaatgactt ttgtaaggat   3129

tggtactatc tatcattcct tatgacatgt acattgtctg tcactaatcc ttggattttg   3189

ctgtattgtc acctaaattg gtacaggtac tgatgaaaat ctctagtgga taatcataac   3249

actctcggtc acatgttttt ccttcagctt gaaagctttt ttttaaaagg aaaagatacc   3309

aaatgcctgc tgctaccacc cttttcaatt gctatctttt gaaaggcacc agtatgtgtt   3369

ttagattgat ttccctgttt cagggaaatc acggacagta gtttcagttc tgatggtata   3429

agcaaaacaa ataaaacgtt tataaaagtt gtatcttgaa acactggtgt tcaacagcta   3489

gcagcttatg tgattcaccc catgccacgt tagtgtcaca aattttatgg tttatctcca   3549

gcaacatttc tctagtactt gcacttatta tcttttgtct aatttaacct taactgaatt   3609

ctccgtttct cctggaggca tttatattca gtgataattc cttcccttag atgcataggg   3669

agagtctcta aatttgatgg aaatggacac ttgagtagtg acttagcctt atgtactctg   3729

ttggaatttg tgctagcagt ttgagcacta gttctgtgtg cctaggaagt taatgctgct   3789

tattgtctca ttctgacttc atggagaatt aatcccacct ttaagcaaag gctactaagt   3849

taatggtatt ttctgtgcag aaattaaatt ttattttcag catttagccc aggaattctt   3909

ccagtaggtg ctcagctatt taaaaacaaa actattctca aacattcatc attagacaac   3969

tggagttttt gctggttttg taacctacca aaatggatag gctgttgaac attccacatt   4029

caaaagtttt gtagggtggt gggaaatggg ggatcttcaa tgtttatttt aaaataaaat   4089

aaaataagtt cttgactttt ctcatgtgtg gttgtggtac atcatattgg aagggttaac   4149

ctgttacttt ggcaaatgag tattttttttg ctagcacctc cccttgcgtg ctttaaatga   4209

catctgcctg ggatgtacca caaccatatg ttacctgtat cttaggggaa tggataaaat   4269

atttgtggtt tactgggtaa tccctagatg atgtatgctt gcagtcctat ataaaactaa   4329
```

-continued

```
atttgctatc tgtgtagaaa ataatttcat gacatttaca atcaggactg aagtaagttc   4389

ttcacacagt gacctctgaa tcagtttcag agaagggatg ggggagaaaa tgccttctag   4449

gttttgaact tctatgcatt agtgcagatg ttgtgaatgt gtaaaggtgt tcatagtttg   4509

actgtttcta tgtatgtttt ttcaaagaat tgttcctttt tttgaactat aatttttctt   4569

tttttggtta ttttaccatc acagtttaaa tgtatatctt ttatgtctct actcagacca   4629

tatttttaaa ggggtgcctc attatggggc agagaacttt tcaataagtc tcattaagat   4689

ctgaatcttg gttctaagca ttctgtataa tatgtgattg cttgtcctag ctgcagaagg   4749

ccttttgttt ggtcaaatgc atattttagc agagtttcaa ggaaatgatt gtcacacatg   4809

tcactgtagc ctcttggtgt agcaagctca catacaaaat acttttgtat atgcataata   4869

taaatcatct catgtggata tgaaacttct tttttaaaac ttaaaaaggt agaatgttat   4929

tgattacctt gattagggca gttttatttc cagatcctaa taattcctaa aaaatatgga   4989

aaagtttttt ttcaatcatt gtaccttgat attaaaacaa atatccttta agtatttcta   5049

atcagttagc ttctacagtt cttttgtctc cttttatatg cagctcttac gtgggagact   5109

tttccactta aaggagacat agaatgtgtg cttattctca gaaggttcat taactgaggt   5169

gatgagttaa caactagttg agcagtcagc ttcctaagtg ttttaggaca tttgttcatt   5229

atattttccg tcatataact agaggaagtg gaatgcagat aagtgccgaa ttcaaaccct   5289

tcattttatg tttaagctcc tgaatctgca ttccacttgg gttgttttta agcattctaa   5349

attttagttg attataagtt agatttcaca gaatcagtat tgcccttgat cttgtccttt   5409

ttatggagtt aacggggagg aagacccctc aggaaaacga aagtaaattg ttaaggctca   5469

tcttcatacc tttttccatt ttgaatccta caaaaatact gcaaaagact agtgaatgtt   5529

taaaattaca ctagattaaa taatatgaaa gtc                                5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160
```

```
Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575
```

```
Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705


<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)

<400> SEQUENCE: 3

cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac       375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac       423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat       471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa       519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca       567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa       615
Ile Lys Lys Thr Ala Arg Arg Glu Gln Leu Met Arg Glu Glu Ala Glu
            130                 135                 140
```

-continued

```
cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa     1575
Pro Leu Tyr Gln Pro Ser His Ala Thr Glu Gln Arg Pro Gln Lys Glu
```

-continued

```
            450                 455                 460

cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca     1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt     1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag     1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa     1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat     1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct     1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat     2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg     2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt     2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct     2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat     2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc     2247
Gln Gln Asn Phe Lys Arg Gly Ser Gly Gln Ser Gly Pro Arg Gly Ala
                675                 680                 685

cca cga ggt aat att ttg tgg tgg tga tcctagctcc taagtggagc           2294
Pro Arg Gly Asn Ile Leu Trp Trp
            690

ttctgttctg gccttggaag agctgttaat agtctgcatg ttaggaatac atttatcctt   2354

tccagacttg ttgctaggga ttaaatgaaa tgctctgttt ctaaaactta atcttggacc   2414

caaattttaa tttttgaatg atttaatttt ccctgttact atataaactg tcttgaaaac   2474

tagaacatat tctcttctca gaaaaagtgt ttttccaact gaaaattatt tttcaggtcc   2534

taaaacctgc taaatgtttt taggaagtac ttactgaaac atttttgtaa gacatttttg   2594

gaatgagatt gaacatttat ataaatttat tattcctctt tcattttttt gaaacatgcc   2654

tattatattt tagggccaga caccctttaa tggccggata agccatagtt aacatttaga   2714

gaaccattta gaagtgatag aactaatgga atttgcaatg ccttttggac ctctattagt   2774

gatataaata tcaagttatt tctgactttt aaacaaaact cccaaattcc taacttattg   2834
```

```
agctatactt aaaaaaaatt acaggtttag agagtttttt gtttttcttt tactgttgga   2894

aaactacttc ccattttggc aggaagttaa cctatttaac aattagagct agcatttcat   2954

gtagtctgaa attctaaatg gttctctgat ttgagggagg ttaaacatca aacaggtttc   3014

ctctattggc cataacatgt ataaaatgtg tgttaaggag gaattacaac gtactttgat   3074

ttgaatacta gtagaaactg gccaggaaaa aggtacattt ttctaaaaat taatggatca   3134

cttgggaatt actgacttga ctagaagtat caaaggatgt ttgcatgtga atgtgggtta   3194

tgttctttcc caccttgtag catattcgat gaaagttgag ttaactgata gctaaaaatc   3254

tgttttaaca gcatgtaaaa agttatttta tctgttaaaa gtcattatac agttttgaat   3314

gttatgtagt ttctttttaa cagtttaggt aataaggtct gttttcattc tggtgctttt   3374

attaattttg atagtatgat gttacttact actgaaatgt aagctagagt gtacactaga   3434

atgtaagctc catgagagca ggtaccttgt ctgtcttctc tgctgtatct attcccaacg   3494

cttgatgatg gtgcctggca catagtaggc actcaataaa tatttgttga atgaatgaa    3553


<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
```

```
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670
```

```
Asn Phe Lys Arg Gly Ser Gly Gln Ser Gly Pro Arg Gly Ala Pro Arg
        675                 680                 685

Gly Asn Ile Leu Trp Trp
    690


<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)

<400> SEQUENCE: 5

gtcacaaata acttggagtt tgcaaaagaa ttacagagga gtttc atg gca tta agt      57
                                                  Met Ala Leu Ser
                                                  1

caa gat att cag aaa aca ata aag aag act gca cgt cgg gag cag ctt       105
Gln Asp Ile Gln Lys Thr Ile Lys Lys Thr Ala Arg Arg Glu Gln Leu
5                   10                  15                  20

atg aga gag gaa gcg gaa caa aaa cgt tta aaa act gta ctt gag ctc       153
Met Arg Glu Glu Ala Glu Gln Lys Arg Leu Lys Thr Val Leu Glu Leu
                25                  30                  35

cag tat gtt ttg gac aaa ttg gga gat gat gaa gtg aga act gac ctg       201
Gln Tyr Val Leu Asp Lys Leu Gly Asp Asp Glu Val Arg Thr Asp Leu
            40                  45                  50

aag caa ggt ttg aat gga gtg cca ata ttg tct gaa gaa gaa ttg tcg       249
Lys Gln Gly Leu Asn Gly Val Pro Ile Leu Ser Glu Glu Glu Leu Ser
        55                  60                  65

ttg ttg gat gaa ttc tac aaa tta gca gac cct gaa cgg gac atg agc       297
Leu Leu Asp Glu Phe Tyr Lys Leu Ala Asp Pro Glu Arg Asp Met Ser
    70                  75                  80

ttg agg ttg aat gag cag tat gaa cat gct tcc att cac ctg tgg gac       345
Leu Arg Leu Asn Glu Gln Tyr Glu His Ala Ser Ile His Leu Trp Asp
85                  90                  95                  100

ttg ctg gaa gga aag gaa aag tct gta tgt gga aca acc tat aaa gca       393
Leu Leu Glu Gly Lys Glu Lys Ser Val Cys Gly Thr Thr Tyr Lys Ala
                105                 110                 115

cta aag gaa att gtt gag cgt gtt ttc cag tca aat tac ttt gac agc       441
Leu Lys Glu Ile Val Glu Arg Val Phe Gln Ser Asn Tyr Phe Asp Ser
            120                 125                 130

act cac aac cac cag aat ggg cta tgt gag gaa gaa gag gca gcc tca       489
Thr His Asn His Gln Asn Gly Leu Cys Glu Glu Glu Glu Ala Ala Ser
        135                 140                 145

gca cct aca gtt gaa gac cag gta gct gaa gct gag cct gag cca gca       537
Ala Pro Thr Val Glu Asp Gln Val Ala Glu Ala Glu Pro Glu Pro Ala
    150                 155                 160

gaa gaa tac act gaa caa agt gaa gtt gaa tca aca gag tat gta aat       585
Glu Glu Tyr Thr Glu Gln Ser Glu Val Glu Ser Thr Glu Tyr Val Asn
165                 170                 175                 180

aga caa ttt atg gca gaa aca cag ttc agc agt ggt gaa aag gag cag       633
Arg Gln Phe Met Ala Glu Thr Gln Phe Ser Ser Gly Glu Lys Glu Gln
                185                 190                 195

gta gat gag tgg acg gtc gaa aca gtg gag gtg gtg aat tca ctc cag       681
Val Asp Glu Trp Thr Val Glu Thr Val Glu Val Val Asn Ser Leu Gln
            200                 205                 210

cag caa cct cag gct gcg tct cct tca gta cca gag ccc cac tct ttg       729
Gln Gln Pro Gln Ala Ala Ser Pro Ser Val Pro Glu Pro His Ser Leu
        215                 220                 225

act ccg gtg gct cag gca gat ccc ctt gtg aga aga cag cga gtc cag       777
```

```
Thr Pro Val Ala Gln Ala Asp Pro Leu Val Arg Arg Gln Arg Val Gln
    230                 235                 240

gac ctt atg gcg cag atg cag ggg ccc tat aat ttc ata cag gat tca      825
Asp Leu Met Ala Gln Met Gln Gly Pro Tyr Asn Phe Ile Gln Asp Ser
245                 250                 255                 260

atg ctg gat ttt gaa aac cag aca ctc gat cct gcc att gta tct gca      873
Met Leu Asp Phe Glu Asn Gln Thr Leu Asp Pro Ala Ile Val Ser Ala
                265                 270                 275

cag cct atg aat ccg aca caa aac atg gac atg ccc cag ctg gtt tgc      921
Gln Pro Met Asn Pro Thr Gln Asn Met Asp Met Pro Gln Leu Val Cys
            280                 285                 290

cct cca gtt cat tct gaa tct aga ctt gct caa cct aat caa gtt cct      969
Pro Pro Val His Ser Glu Ser Arg Leu Ala Gln Pro Asn Gln Val Pro
        295                 300                 305

gta caa cca gaa gct aca cag gtt cct ttg gtt tca tcc aca agt gag     1017
Val Gln Pro Glu Ala Thr Gln Val Pro Leu Val Ser Ser Thr Ser Glu
    310                 315                 320

ggg tat aca gca tct caa ccc ttg tac cag cct tct cat gct aca gag     1065
Gly Tyr Thr Ala Ser Gln Pro Leu Tyr Gln Pro Ser His Ala Thr Glu
325                 330                 335                 340

caa cga cca caa aag gaa cca att gac cag att cag gca aca atc tct     1113
Gln Arg Pro Gln Lys Glu Pro Ile Asp Gln Ile Gln Ala Thr Ile Ser
                345                 350                 355

tta aat aca gac cag act aca gcg tca tca tcc ctt ccg gct gct tct     1161
Leu Asn Thr Asp Gln Thr Thr Ala Ser Ser Ser Leu Pro Ala Ala Ser
            360                 365                 370

cag cct cag gta ttc cag gct ggg aca agc aaa cca tta cat agc agt     1209
Gln Pro Gln Val Phe Gln Ala Gly Thr Ser Lys Pro Leu His Ser Ser
        375                 380                 385

gga atc aat gta aat gca gct cca ttc caa tcc atg caa acg gtg ttc     1257
Gly Ile Asn Val Asn Ala Ala Pro Phe Gln Ser Met Gln Thr Val Phe
    390                 395                 400

aat atg aat gcc cca gtt cct cct gtt aat gaa cca gaa act ttg aaa     1305
Asn Met Asn Ala Pro Val Pro Pro Val Asn Glu Pro Glu Thr Leu Lys
405                 410                 415                 420

caa caa aat cag tac cag gcc agt tat aac cag agc ttt tct agt cag     1353
Gln Gln Asn Gln Tyr Gln Ala Ser Tyr Asn Gln Ser Phe Ser Ser Gln
                425                 430                 435

cct cac caa gta gaa caa aca gag gga tgc cgc aaa tga acactcagca      1402
Pro His Gln Val Glu Gln Thr Glu Gly Cys Arg Lys
            440                 445

agtgaattaa tctgattcac aggattatgt ttaaacgcca aaaacacact ggccagtgta   1462

ccataatatg ttaccagaag agttattatc tatttgttct ccctttcagg aaacttattg   1522

taaagggact gttttcatcc cataaagaca ggactacaat tgtcagcttt atattacctg   1582

gaaaaaaaaa aaaaaaaaaa aaa                                           1605


<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45
```

```
Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
        275                 280                 285

Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
        355                 360                 365

Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
        435                 440                 445
```

<210> SEQ ID NO 7
<211> LENGTH: 4154

```
<212> TYPE: DNA
<213> ORGANISM: Canis familiaris
<220> FEATURE:
<221> NAME/KEY: CDS
<222> LOCATION: (1)..(2154)

<400> SEQUENCE: 7

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285
```

-continued

```
gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
```

```
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc      2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa              2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttgttct ccctttcagg aaacttattg taaagggact   2274

gttttcatcc cataaagaca ggactacaat tgtcagcttt atattacctg gatatggaag   2334

gaaactattt ttattctgca tgttcttcct aagcgtcatc ttgagccttg cacatgatac   2394

tcagattcct cacccttgct taggagtaaa acataataca ctttacaggg tgatatctcc   2454

atagttattt gaagtggctt ggaaaaagca agattaactt ctgacattgg ataaaaatca   2514

acaaatcagc cctagagtta ttcaaatggt aattgacaaa aactaaaata tttcccttcg   2574

agaaggagtg gaatgtggtt tggcagaaca actgcatttc acagcttttc cggttaaatt   2634

ggagcactaa acgtttagat gcataccaaa ttatgcatgg gcccttaata taaaaggctg   2694

gctaccagct ttgacacagc actattcatc ctctggccaa acaactgtgg ttaaacaaca   2754

catgtaaatt gctttttaac agctgatact ataataagac aaagccaaaa tgcaaaaatt   2814

gggctttgat tggcactttt tgaaaaatat gcaacaaata tgggatgtaa tctggatggc   2874

cgcttctgta cttaatgtga agtatttaga tacctttttg aacacttaac agtttcttct   2934

gacaatgact tttgtaagga ttggtactat ctatcattcc ttataatgta cattgtctgt   2994

cactaatcct cagatcttgc tgtattgtca cctaaattgg tacaggtact gatgaaaata   3054

tctaatggat aatcataaca ctcttggtca catgtttttc ctgcagcctg aaggttttta   3114

aaagaaaaag atatcaaatg cctgctgcta ccaccctttt aaattgctat cttttgaaaa   3174

gcaccagtat gtgttttaga ttgatttccc tattttaggg aaatgacaga cagtagtttc   3234

agttctgatg gtataagcaa aacaaataaa acatgtttat aaaagttgta tcttgaaaca   3294

ctggtgttca acagctagca gcttatgtgg ttcaccccat gcattgttag tgtttcagat   3354

tttatggtta tctccagcag ctgtttctgt agtacttgca tttatctttt gtctaaccct   3414

aatattctca cggaggcatt tatattcaaa gtggtgatcc cttcacttag acgcataggg   3474

agagtcacaa gtttgatgaa gaggacagtg tagtaattta tatgctgttg gaatttgtgc   3534

tagcagtttg agcactagtt ctgtgtgcct atgaacttaa tgctgcttgt catattccac   3594

tttgacttca tggagaatta atcccatcta ctcagcaaag gctatactaa tactaagtta   3654
```

```
atggtatttt ctgtgcagaa attgaatttt gttttattag catttagcta aggaattttt   3714

ccagtaggtg ctcagctact aaagaaaaac aaaaacaaga cacaaaacta ttctcaaaca   3774

ttcattgtta gacaactgga gtttttgctg gttttgtaac ctactaaaat ggataggctg   3834

ttgaacattc cacattcaaa agttttttgt agggtggtgg ggaagggggg gtgtcttcaa   3894

tgtttatttt aaaataaaat aagttcttga cttttctcat gtgtggttgt ggtacatcat   3954

attggaaggg ttatctgttt acttttgcaa atgagtattt ctcttgctag cacctcccgt   4014

tgtgcgcttt aaatgacatc tgcctgggat gtaccacaac catatgttag ctgtatttta   4074

tggggaatag ataaaatatt cgtggtttat tgggtaatcc ctagatgtgt atgcttacaa   4134

tcctatatat aaaactaaat                                               4154
```

```
<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
```

```
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700
```

```
Asn Arg Gly Met Pro Gln Met Asn Thr Gln Gln Val Asn
705                 710                 715


<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)

<400> SEQUENCE: 9

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255
```

-continued

```
act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575
```

-continued

```
gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt aat att ttg tgg tgg tga         2109
Ser Gly Pro Arg Gly Ala Pro Arg Gly Asn Ile Leu Trp Trp
    690                 695                 700

tcctagctcc taagtggagc ttctgttctg gccttggaag agctgttcca tagtctgcat   2169

gtaggttaca tgttaggaat acatttatca ttaccagact tgttgctagg gattaaatga   2229

aatgctctgt ttctaaaact tctcttgaac ccaaatttaa ttttttgaat gactttccct   2289

gttactatat aaattgtctt gaaaactaga acatttctcc tcctcagaaa aagtgttttt   2349

ccaactgcaa attatttttc aggtcctaaa acctgctaaa tgtttttagg aagtacttac   2409

tgaaacattt ttgtaagaca tttttggaat gagattgaac atttatataa atttattatt   2469

attcctcttt catttttgaa catgcatatt atattttagg gtcagaaatc ctttaatggc   2529

caaataagcc atagttacat ttagagaacc atttagaagt gatagaacta actgaaattt   2589

caatgccttt ggatcattaa tagcgatata aatttcaaat tgtttctgac ttttaaataa   2649

aacatccaaa atcctaacta acttcctgaa ctatatttaa aaattacagg tttaaggagt   2709

ttctggtttt ttttctctta ccataggaaa actgtttcct gtttggccag gaagtcaacc   2769

tgtgtaataa ttagaagtag catttcatat gatctgaagt tctaaatggt tctctgattt   2829

aagggaagtt aaattgaata ggtttcctct agttattggc cataacatgt ataaaatgta   2889

tattaaggag gaatacaaag tactttgatt tcaatgctag tagaaactgg ccagcaaaaa   2949

ggtgcatttt atttttaaat taatggatca cttgggaatt actgacttga agtatcaaag   3009

gatatttgca tgtgaatgtg ggttatgttc tttctcacct tgtagcatat tctatgaaag   3069

ttgagttgac tggtagctaa aaatctgttt taacagcatg taaaaagtta ttttatctgt   3129

tacaagtcat tatacaattt tgaatgttat gtagtttctt tttaacagtt taggtaacaa   3189

ggtctgtttt tcattctggt gcttttatta attttgatag tatgatgtta cttactactg   3249

aaatgtaagc tagagtgtac actagaatgt aagctccatg agagcaggta ccttgtctgt   3309

cttcactgct gtatctattt ccaacgcctg atgacagtgc ctgacacata gtaggcactc   3369

aataaatact tgttgaatga atgaatgaat gagtactggt ggaatactcc attagctcta   3429

ctcttctttt agctagagaa catgagcaaa tttgcgcatg acaacttcca ggacaggtga   3489
```

```
acactgaaga attgacctct taaacctaat aatgtggtga caagctgccc acatgcttct   3549
tgacttcaga tgaaaatctg cttgaaggca aagcaaataa tatttgaaag aaaaaccaaa   3609
tgccattttt gtcttctagg tcgtggaggg cccccaagac ccaacagagg gatgccgcaa   3669
atgaacactc agcaagtgaa ttaatctgat tcacaggatt atgtttaaac gccaaaaaca   3729
cactggccag tgtaccataa tatgttacca gaagagttat tatctatttg ttctcccttt   3789
caggaaactt attgtaaagg gactgttttc atcccataaa gacaggacta caattgtcag   3849
ctttatatta cctggatatg gaaggaaact atttttattc tgcatgttct tcctaagcgt   3909
catcttgagc cttgcacatg atactcagat tcctcaccct tgcttaggag taaaacataa   3969
tacactttac agggtgatat ctccatagtt atttgaagtg gcttggaaaa agcaagatta   4029
acttctgaca ttggataaaa atcaacaaat cagccctaga gttattcaaa tggtaattga   4089
caaaaactaa aatatttccc ttcgagaagg agtggaatgt ggtttggcag aacaactgca   4149
tttcacagct tttccggtta aattggagca ctaaacgttt agatgcatac caaattatgc   4209
atgggccctt aatataaaag gctggctacc agctttgaca cagcactatt catcctctgg   4269
ccaaacaact gtggttaaac aacacatgta aattgctttt taacagctga tactataata   4329
agacaaagcc aaaatgcaaa aattgggctt tgattggcac tttttgaaaa atatgcaaca   4389
aatatgggat gtaatctgga tggccgcttc tgtacttaat gtgaagtatt tagatacctt   4449
tttgaacact taacagtttc ttctgacaat gacttttgta aggattggta ctatctatca   4509
ttccttataa tgtacattgt ctgtcactaa tcctcagatc ttgctgtatt gtcacctaaa   4569
ttggtacagg tactgatgaa aatatctaat ggataatcat aacactcttg gtcacatgtt   4629
tttcctgcag cctgaaggtt tttaaaagaa aaagatatca aatgcctgct gctaccaccc   4689
ttttaaattg ctatcttttg aaaagcacca gtatgtgttt tagattgatt tccctatttt   4749
agggaaatga cagacagtag tttcagttct gatggtataa gcaaaacaaa taaaacatgt   4809
ttataaaagt tgtatcttga aacactggtg ttcaacagct agcagcttat gtggttcacc   4869
ccatgcattg ttagtgtttc agattttatg gttatctcca gcagctgttt ctgtagtact   4929
tgcatttatc                                                          4939
```

<210> SEQ ID NO 10
<211> LENGTH: 702
<212> TYPE: PRT
<213> ORGANISM: Canis familiaris

<400> SEQUENCE: 10

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110
```

-continued

```
Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
```

```
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Asn Ile Leu Trp Trp
    690                 695                 700


<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)

<400> SEQUENCE: 11

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140
```

```
atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460
```

```
caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gga tgc cgc aaa tga acactcagca agtgaattaa tctgattcac    2070
Tyr Gln Arg Gly Cys Arg Lys
        675

aggattatgt ttaaacgcca aaaacacact ggccagtgta ccataatatg ttaccagaag   2130

agttattatc tatttgttct ccctttcagg aaacttattg taaagggact gttttcatcc   2190

cataaagaca ggactacaat tgtcagcttt atattacctg gatatggaag gaaactattt   2250

ttattctgca tgttcttcct aagcgtcatc ttgagccttg cacatgatac tcagattcct   2310

caccccttgct taggagtaaa acataataca ctttacaggg tgatatctcc atagttattt  2370

gaagtggctt ggaaaaagca agattaactt ctgacattgg ataaaaatca acaaatcagc   2430

cctagagtta ttcaaatggt aattgacaaa aactaaaata tttcccttcg agaaggagtg   2490

gaatgtggtt tggcagaaca actgcatttc acagcttttc cggttaaatt ggagcactaa   2550

acgtttagat gcataccaaa ttatgcatgg gcccttaata taaaaggctg gctaccagct   2610

ttgacacagc actattcatc ctctggccaa acaactgtgg ttaaacaaca catgtaaatt   2670

gctttttaac agctgatact ataataagac aaagccaaaa tgcaaaaatt gggctttgat   2730
```

```
tggcactttt tgaaaaatat gcaacaaata tgggatgtaa tctggatggc cgcttctgta   2790

cttaatgtga agtatttaga taccttttg aacacttaac agtttcttct gacaatgact   2850

tttgtaagga ttggtactat ctatcattcc ttataatgta cattgtctgt cactaatcct   2910

cagatcttgc tgtattgtca cctaaattgg tacaggtact gatgaaaata tctaatggat   2970

aatcataaca ctcttggtca catgtttttc ctgcagcctg aaggttttta aaagaaaaag   3030

atatcaaatg cctgctgcta ccaccctttt aaattgctat cttttgaaaa gcaccagtat   3090

gtgttttaga ttgatttccc tattttaggg aaatgacaga cagtagtttc agttctgatg   3150

gtataagcaa aacaaataaa acatgtttat aaaagttgta tcttgaaaca ctggtgttca   3210

acagctagca gcttatgtgg ttcaccccat gcattgttag tgtttcagat tttatggtta   3270

tctccagcag ctgtttctgt agtacttgca tttatc                             3306


<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270
```

```
Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
        675
```

```
<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)

<400> SEQUENCE: 13

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
```

-continued

```
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590
```

```
ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttggact gttttcatcc cataaagaca ggactacaat   2274

tgtcagc                                                             2281


<210> SEQ ID NO 14
<211> LENGTH: 717
<212> TYPE: PRT
<213> ORGANISM: Canis familiaris

<400> SEQUENCE: 14

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175
```

-continued

```
Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
```

```
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715


<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)

<400> SEQUENCE: 15

cgcgtctcgc cccgtccacc gattgactcg ccgctcttgt ccttcctccc gctctttctt      60

ctctcccctt acggtttcaa g atg cct tcg gcc acc agc cac agc gga agc      111
                        Met Pro Ser Ala Thr Ser His Ser Gly Ser
                        1               5                   10

ggc agc aag tcg tcc gga ccg cca ccg ccg tcg ggt tcc tcc ggg aat      159
Gly Ser Lys Ser Ser Gly Pro Pro Pro Pro Ser Gly Ser Ser Gly Asn
                15                  20                  25

gag gcg ggg gcc ggg gcc gcc gcg ccg gct tcc caa cac ccc atg acc      207
Glu Ala Gly Ala Gly Ala Ala Ala Pro Ala Ser Gln His Pro Met Thr
            30                  35                  40

ggc acc ggg gct gtc cag acc gag gcc atg aag cag att ctc ggg gtg      255
Gly Thr Gly Ala Val Gln Thr Glu Ala Met Lys Gln Ile Leu Gly Val
        45                  50                  55

atc gac aag aaa ctt cgg aac ctg gag aag aaa aag ggc aag ctt gat      303
Ile Asp Lys Lys Leu Arg Asn Leu Glu Lys Lys Lys Gly Lys Leu Asp
    60                  65                  70

gat tat cag gaa cga atg aac aaa ggg gaa agg ctt aat caa gat cag      351
Asp Tyr Gln Glu Arg Met Asn Lys Gly Glu Arg Leu Asn Gln Asp Gln
75                  80                  85                  90

ctg gat gcc gtg tct aag tac cag gaa gtc aca aat aac ttg gag ttt      399
Leu Asp Ala Val Ser Lys Tyr Gln Glu Val Thr Asn Asn Leu Glu Phe
                95                  100                 105

gca aaa gaa tta cag agg agt ttc atg gca tta agc caa gat att cag      447
Ala Lys Glu Leu Gln Arg Ser Phe Met Ala Leu Ser Gln Asp Ile Gln
            110                 115                 120

aaa aca ata aag aag aca gca cgt cgg gag cag ctt atg aga gag gaa      495
Lys Thr Ile Lys Lys Thr Ala Arg Arg Glu Gln Leu Met Arg Glu Glu
        125                 130                 135

gct gaa cag aaa cgt tta aaa aca gta ctt gag ctg cag tat gtt ttg      543
Ala Glu Gln Lys Arg Leu Lys Thr Val Leu Glu Leu Gln Tyr Val Leu
    140                 145                 150

gac aaa cta gga gat gat gaa gtg aga act gac ctg aag caa ggt ttg      591
Asp Lys Leu Gly Asp Asp Glu Val Arg Thr Asp Leu Lys Gln Gly Leu
155                 160                 165                 170
```

-continued

```
aat gga gtg cca ata ttg tct gaa gag gag ttg tcg ttg tta gat gag      639
Asn Gly Val Pro Ile Leu Ser Glu Glu Glu Leu Ser Leu Leu Asp Glu
                175                 180                 185

ttc tac aaa tta gca gac cct gaa cga gac atg agc ttg agg ttg aat      687
Phe Tyr Lys Leu Ala Asp Pro Glu Arg Asp Met Ser Leu Arg Leu Asn
            190                 195                 200

gag cag tat gaa cat gcc tcc att cac ctg tgg gac ttg ctg gaa gga      735
Glu Gln Tyr Glu His Ala Ser Ile His Leu Trp Asp Leu Leu Glu Gly
        205                 210                 215

aag gaa aaa cct gta tgt gga aca act tat aaa gct cta aag gaa att      783
Lys Glu Lys Pro Val Cys Gly Thr Thr Tyr Lys Ala Leu Lys Glu Ile
    220                 225                 230

gtt gag cgt gtt ttc cag tca aac tac ttt gac agc acc cac aac cac      831
Val Glu Arg Val Phe Gln Ser Asn Tyr Phe Asp Ser Thr His Asn His
235                 240                 245                 250

cag aat ggt ctg tgt gag gaa gag gag gca gcc tca gca cct aca gtt      879
Gln Asn Gly Leu Cys Glu Glu Glu Glu Ala Ala Ser Ala Pro Thr Val
                255                 260                 265

gaa gac cag gca gct gaa gct gaa cct gag cca gtg gaa gaa tat act      927
Glu Asp Gln Ala Ala Glu Ala Glu Pro Glu Pro Val Glu Glu Tyr Thr
            270                 275                 280

gaa caa aat gag gtt gaa tca aca gag tat gta aat aga caa ttt atg      975
Glu Gln Asn Glu Val Glu Ser Thr Glu Tyr Val Asn Arg Gln Phe Met
        285                 290                 295

gca gaa aca cag ttc agc agt ggt gaa aag gag cag gta gat gat tgg     1023
Ala Glu Thr Gln Phe Ser Ser Gly Glu Lys Glu Gln Val Asp Asp Trp
    300                 305                 310

aca gtt gaa aca gtt gag gtg gta aat tca ctc cag cag caa cct cag     1071
Thr Val Glu Thr Val Glu Val Val Asn Ser Leu Gln Gln Gln Pro Gln
315                 320                 325                 330

gct gca tct cct tca gta cca gaa ccc cac tct ttg acc cca gtg gct     1119
Ala Ala Ser Pro Ser Val Pro Glu Pro His Ser Leu Thr Pro Val Ala
                335                 340                 345

caa gcc gat ccc ctc gtg aga aga cag cga gta cag gac ctt atg gca     1167
Gln Ala Asp Pro Leu Val Arg Arg Gln Arg Val Gln Asp Leu Met Ala
            350                 355                 360

caa atg cag ggg ccc tat aat ttc ata cag gat tca atg ttg gat ttt     1215
Gln Met Gln Gly Pro Tyr Asn Phe Ile Gln Asp Ser Met Leu Asp Phe
        365                 370                 375

gaa aac cag aca ctt gat cct gcc att gta tct gca cag ccg atg aat     1263
Glu Asn Gln Thr Leu Asp Pro Ala Ile Val Ser Ala Gln Pro Met Asn
    380                 385                 390

cca gca cag aac atg gac ata ccc cag ctg gtt tgc cct cca gtt cat     1311
Pro Ala Gln Asn Met Asp Ile Pro Gln Leu Val Cys Pro Pro Val His
395                 400                 405                 410

tct gaa tct aga ctt gct caa cct aat caa gtt tct gta cag cca gaa     1359
Ser Glu Ser Arg Leu Ala Gln Pro Asn Gln Val Ser Val Gln Pro Glu
                415                 420                 425

gct aca cag gtt cct ttg gtt tca tcc aca agt gag gga tat aca gca     1407
Ala Thr Gln Val Pro Leu Val Ser Ser Thr Ser Glu Gly Tyr Thr Ala
            430                 435                 440

tct caa ccc ttg tac caa cct tct cat gct act gac caa cga cca caa     1455
Ser Gln Pro Leu Tyr Gln Pro Ser His Ala Thr Asp Gln Arg Pro Gln
        445                 450                 455

aag gaa ccg att gat cag att cag gcg acg atc tct tta aat aca gac     1503
Lys Glu Pro Ile Asp Gln Ile Gln Ala Thr Ile Ser Leu Asn Thr Asp
    460                 465                 470

cag act aca gca tca tca tcc ctt cct gct gct tct cag cct caa gtg     1551
Gln Thr Thr Ala Ser Ser Ser Leu Pro Ala Ala Ser Gln Pro Gln Val
```

```
475                 480                 485                 490

ttc cag gct ggg aca agc aaa cct tta cat agc agt gga atc aat gta     1599
Phe Gln Ala Gly Thr Ser Lys Pro Leu His Ser Ser Gly Ile Asn Val
                495                 500                 505

aat gca gct cca ttc caa tcc atg caa acg gta ttc aat atg aat gcc     1647
Asn Ala Ala Pro Phe Gln Ser Met Gln Thr Val Phe Asn Met Asn Ala
            510                 515                 520

cca gtt cct cct gtt aat gaa cca gaa act tta aaa cag caa aat cag     1695
Pro Val Pro Pro Val Asn Glu Pro Glu Thr Leu Lys Gln Gln Asn Gln
        525                 530                 535

tac cag gcc agt tac aac cag agc ttt tcc agt cag cct cac caa gta     1743
Tyr Gln Ala Ser Tyr Asn Gln Ser Phe Ser Ser Gln Pro His Gln Val
    540                 545                 550

gaa caa aca gag ctt cag caa gaa cag ctt caa aca gtg gtt ggc act     1791
Glu Gln Thr Glu Leu Gln Gln Glu Gln Leu Gln Thr Val Val Gly Thr
555                 560                 565                 570

tat cat ggt tct cag gac cag ccc cat caa gtg act ggt aac cac cag     1839
Tyr His Gly Ser Gln Asp Gln Pro His Gln Val Thr Gly Asn His Gln
                575                 580                 585

cag cct cct cag cag aac act gga ttt cca cgt agc aat cag ccc tat     1887
Gln Pro Pro Gln Gln Asn Thr Gly Phe Pro Arg Ser Asn Gln Pro Tyr
            590                 595                 600

tac aac agt cgt ggt gtg tct cgt gga ggt tcc cgt ggt gct aga ggc     1935
Tyr Asn Ser Arg Gly Val Ser Arg Gly Gly Ser Arg Gly Ala Arg Gly
        605                 610                 615

ttg atg aat gga tac aga gga cct gct aat gga ttc aga gga gga tat     1983
Leu Met Asn Gly Tyr Arg Gly Pro Ala Asn Gly Phe Arg Gly Gly Tyr
    620                 625                 630

gat ggt tac cgc cct tca ttc tct act aac act cca aac agt ggt tat     2031
Asp Gly Tyr Arg Pro Ser Phe Ser Thr Asn Thr Pro Asn Ser Gly Tyr
635                 640                 645                 650

aca caa tct caa ttc agt gct ccc cgg gac tac tct ggc tat cag cgg     2079
Thr Gln Ser Gln Phe Ser Ala Pro Arg Asp Tyr Ser Gly Tyr Gln Arg
                655                 660                 665

gat gga tat cag cag aat ttc aag cga ggc tct ggg cag agt gga cca     2127
Asp Gly Tyr Gln Gln Asn Phe Lys Arg Gly Ser Gly Gln Ser Gly Pro
            670                 675                 680

cgg gga gcc cca cga ggt cgt gga ggg ccc cca aga ccc aac aga ggg     2175
Arg Gly Ala Pro Arg Gly Arg Gly Gly Pro Pro Arg Pro Asn Arg Gly
        685                 690                 695

atg ccg caa atg aac act cag caa gtg aat taa tctgattcac aggattatgt   2228
Met Pro Gln Met Asn Thr Gln Gln Val Asn
    700                 705

ttaatcgcca aaaacacact ggccagtgta ccataatatg ttaccagaag agttattatc   2288

tatttgttct ccctttcagg aaacttattg taaagggact gttttcatcc cataaagaca   2348

ggactacaat tgtcagcttt atattacctg gatatggaag gaaactattt ttactctgca   2408

tgttctgtcc taagcgtcat cttgagcctt gcacatgata ctcagattcc tcacccttgc   2468

ttaggagtaa aacataatat actttaatgg ggtgatatct ccatagttat ttgaagtggc   2528

ttggataaag caagactgac ttctgacatt ggataaaatc tacaaatcag ccctagagtc   2588

attcagtggt aactgacaaa actaaaatat ttcccttgaa aggaagatgg aaggagtgga   2648

gtgtggtttg gcagaacaac tgcatttcac agcttttcca cttaaattgg agcactgaac   2708

atttagatgc ataccgaatt atgcatgggc cctaatcaca cagacaaggc tggtgccagc   2768

cttaggcttg acacggcagt gttcaccctc tggccagacg actgtggttc aagacacatg   2828

taaattgctt tttaacagct gatactgtat aagacaaagc caaaatgcaa aattaggctt   2888
```

```
tgattggcac ttttcgaaaa atatgcaaca attaagggat ataatctgga tggccgcttc   2948

tgtacttaat gtgaaatatt tagatacctt tcaaacactt aacagtttct ttgacaatga   3008

gttttgtaag gattggtagt aaatatcatt ccttatgacg tacattgtct gtcactaatc   3068

cttggatctt gctgtattgt cacctaaatt ggtacaggta ctgatgaaaa tctaatggat   3128

aatcataaca ctcttggtta catgtttttc ctgcagcctg aaagttttta taagaaaaag   3188

acatcaaatg cctgctgctg ccaccctttt aaattgctat cttttgaaaa gcaccagtat   3248

gtgttttaga ttgatttccc tattttaggg aaatgacagt cagtagtttc acttctgatg   3308

gtataagcaa acaaataaaa catgtttata aaaaaaaaaa aaaaaaaaaa aaaaaaaaaa   3368

aaaaaaaaaa aaaaaaaa                                                 3386


<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Glu Gln Asn Glu Val Glu
```

```
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
            660                 665                 670

Phe Lys Arg Gly Ser Gly Gln Ser Gly Pro Arg Gly Ala Pro Arg Gly
        675                 680                 685

Arg Gly Gly Pro Pro Arg Pro Asn Arg Gly Met Pro Gln Met Asn Thr
    690                 695                 700
```

```
Gln Gln Val Asn
705


<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)

<400> SEQUENCE: 17

atg gag ggc aag ctc gat gat tac caa gag cga atg aac aaa gga gaa       48
Met Glu Gly Lys Leu Asp Asp Tyr Gln Glu Arg Met Asn Lys Gly Glu
1               5                   10                  15

agg ctt aat cag gat cag ctg gat gct gtg tct aag tac cag gaa gtc       96
Arg Leu Asn Gln Asp Gln Leu Asp Ala Val Ser Lys Tyr Gln Glu Val
            20                  25                  30

aca aat aac ttg gag ttt gcg aaa gaa ttg cag agg agt ttc atg gcg      144
Thr Asn Asn Leu Glu Phe Ala Lys Glu Leu Gln Arg Ser Phe Met Ala
        35                  40                  45

ttg agt cag gat att cag aaa aca ata aag aag acg gca cgt cgg gag      192
Leu Ser Gln Asp Ile Gln Lys Thr Ile Lys Lys Thr Ala Arg Arg Glu
    50                  55                  60

cag ctt atg aga gaa gaa gct gaa cag aaa cgt tta aaa act gta ctt      240
Gln Leu Met Arg Glu Glu Ala Glu Gln Lys Arg Leu Lys Thr Val Leu
65                  70                  75                  80

gag ctg cag tat gtt ttg gac aaa ttg gga gat gaa gaa gtg cga act      288
Glu Leu Gln Tyr Val Leu Asp Lys Leu Gly Asp Glu Glu Val Arg Thr
                85                  90                  95

gac ctg aaa caa ggt ttg aat gga gtg cca ata ctc tct gaa gaa gag      336
Asp Leu Lys Gln Gly Leu Asn Gly Val Pro Ile Leu Ser Glu Glu Glu
            100                 105                 110

ttg tcg ctg ttg gat gag ttc tac aag tta gca gac cct gta cgg gac      384
Leu Ser Leu Leu Asp Glu Phe Tyr Lys Leu Ala Asp Pro Val Arg Asp
        115                 120                 125

atg agc ttg agg ttg aat gag cag tat gag cat gcc tcc att cac ctg      432
Met Ser Leu Arg Leu Asn Glu Gln Tyr Glu His Ala Ser Ile His Leu
    130                 135                 140

tgg gac ttg ctg gaa ggg aag gaa aaa tct gtc tgt gga aca acc tat      480
Trp Asp Leu Leu Glu Gly Lys Glu Lys Ser Val Cys Gly Thr Thr Tyr
145                 150                 155                 160

aaa gct ctg agg gaa att gtt gag cgt gtt ttc cag tcc aac tac ttt      528
Lys Ala Leu Arg Glu Ile Val Glu Arg Val Phe Gln Ser Asn Tyr Phe
                165                 170                 175

gac agc acc cac aac cac cag aat ggg ctc tgt gag gag gaa gag gct      576
Asp Ser Thr His Asn His Gln Asn Gly Leu Cys Glu Glu Glu Glu Ala
            180                 185                 190

acc tca gct cca aca gct gaa gac cag gga gct gaa gct gaa cct gag      624
Thr Ser Ala Pro Thr Ala Glu Asp Gln Gly Ala Glu Ala Glu Pro Glu
        195                 200                 205

cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
    210                 215                 220

gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240

cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255
```

```
cag cag caa cct cag gct gca tct cct tca gta ccg gag ccc cac tct      816
Gln Gln Gln Pro Gln Ala Ala Ser Pro Ser Val Pro Glu Pro His Ser
            260                 265                 270

ttg act cca gtg gct cag gca gat ccc ctt gtg aga aga cag cga gta      864
Leu Thr Pro Val Ala Gln Ala Asp Pro Leu Val Arg Arg Gln Arg Val
        275                 280                 285

cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300

tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320

gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335

tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350

cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365

gag ggg tat aca gca tct cag ccc ttg tac cag cct tct cat gct aca     1152
Glu Gly Tyr Thr Ala Ser Gln Pro Leu Tyr Gln Pro Ser His Ala Thr
    370                 375                 380

gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400

tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415

tct cag cct cag gtg ttc cag gct ggg aca agc aaa cct tta cac agc     1296
Ser Gln Pro Gln Val Phe Gln Ala Gly Thr Ser Lys Pro Leu His Ser
            420                 425                 430

agt ggg atc aat gta aat gca gcg cca ttc cag tcc atg caa acg gtg     1344
Ser Gly Ile Asn Val Asn Ala Ala Pro Phe Gln Ser Met Gln Thr Val
        435                 440                 445

ttc aac atg aat gcc ccg gtt cct cct gtt aat gaa cca gaa act tta     1392
Phe Asn Met Asn Ala Pro Val Pro Pro Val Asn Glu Pro Glu Thr Leu
    450                 455                 460

aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480

ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495

acg gtg gtt ggt act tac cat gct tcc caa gac cag ccc cat caa gtg     1536
Thr Val Val Gly Thr Tyr His Ala Ser Gln Asp Gln Pro His Gln Val
            500                 505                 510

acc ggt aac cac cag cag cct ccc cag cag aac act ggg ttt cca cgt     1584
Thr Gly Asn His Gln Gln Pro Pro Gln Gln Asn Thr Gly Phe Pro Arg
        515                 520                 525

agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
    530                 535                 540

cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
545                 550                 555                 560

ttc aga gga gga tat gat ggt tac cgc cct tcg ttc tct aac act cca     1728
Phe Arg Gly Gly Tyr Asp Gly Tyr Arg Pro Ser Phe Ser Asn Thr Pro
                565                 570                 575
```

```
aac agc ggt tac aca cag tct cag ttc agt gct ccc cgg gac tac tct     1776
Asn Ser Gly Tyr Thr Gln Ser Gln Phe Ser Ala Pro Arg Asp Tyr Ser
            580                 585                 590

ggc tat cag cgg gat gga tat cag cag aat ttc aag cga ggc tct ggg     1824
Gly Tyr Gln Arg Asp Gly Tyr Gln Gln Asn Phe Lys Arg Gly Ser Gly
        595                 600                 605

cag agt gga ccc cgg gga gcc cca cga ggt cgt gga ggg ccc cca aga     1872
Gln Ser Gly Pro Arg Gly Ala Pro Arg Gly Arg Gly Gly Pro Pro Arg
    610                 615                 620

ccc aac aga ggg atg ccg caa atg aac act cag caa gtg aat taa         1917
Pro Asn Arg Gly Met Pro Gln Met Asn Thr Gln Gln Val Asn
625                 630                 635

tctgattcac aggattatct ttaatcgcca aaacacactg gccagtgtac cataatatgt   1977

taccagaaga gttattatct atttgttctc cctttcagga aacttattgt aaagggactg   2037

ttttcatccc ataaagacag gactacagtt gtcagcttta tattacctgg atatggaagg   2097

aaactatttt tactctgcat gttctgtcct aagcgtcatc ttgagccttg cacatgatac   2157

tcagattcct ttcccttgct taggagtaaa acataatata ctttatgggg tgataatatc   2217

tccatagtta tttgaagtgg cttggaaaaa gcaagattga cttttgacat tggataaaat   2277

ctacaaatca gccctagagt ttcatggtca ttcacaaaac taaaatattt cccttgaaag   2337

gaagatggaa ggactggagt gtggtttggc agaacaactg catttcacag cttttcctat   2397

taaattggag cactgaatgt taaatgcata ccaaattatg catgggccct taatcacaca   2457

tacatggcta ccagctttga cacagcacta ttcatcctct ggccaaacga ctgtggttaa   2517

aaacacgtgt aaattgcttt ttaacagctg atactgtaaa agacaaagct aaaatgcaaa   2577

attaggcttt cattggcact tttcgaaaaa tatgcaacaa atttgggatg taatctggat   2637

ggccacttct gtacttaatg tgaagtattt agataccttt ttgaacactt aacagtttct   2697

tcgacaatga cttttgtaag gattggtagt atatatcatt ccttatgaca tacattgtct   2757

gttgctaatc cttggatctt gctgtattgt cacctaaatt ggtacaggta ctgatgaaaa   2817

tctctcatgg ataaacctaa cactcttcgt cacatgtttt tcctgcagcc tgaaggtttt   2877

taaaaggaaa agatatcaaa tgcctgctgc taccaccctt ttaaattgct atcttttgaa   2937

aagcaccagt atgtgttttt agattgattt ccctatttta gggaaatgac agtcagtagt   2997

ttcagttctg atggtataag caaagcaaat aaaacgtgtt tataaaagtt gtatcttgaa   3057

acactggtgt tcaacagcta gcagcttctg tggttcaccc cctgccttgt tagtgttacc   3117

catttatggt tatctccagc agcaatttct cta                                3150

<210> SEQ ID NO 18
<211> LENGTH: 638
<212> TYPE: PRT
<213> ORGANISM: Equus caballus

<400> SEQUENCE: 18

Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala
        35                  40                  45

Leu Ser Gln Asp Ile Gln Lys Thr Ile Lys Lys Thr Ala Arg Arg Glu
    50                  55                  60
```

```
Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
        275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Pro Val Asn Glu Pro Glu Thr Leu
    450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
```

```
                485                 490                 495

Thr Val Val Gly Thr Tyr His Ala Ser Gln Asp Gln Pro His Gln Val
            500                 505                 510

Thr Gly Asn His Gln Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Gly Pro Pro Arg
    610                 615                 620

Pro Asn Arg Gly Met Pro Gln Met Asn Thr Gln Gln Val Asn
625                 630                 635


<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)

<400> SEQUENCE: 19

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg       370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg       514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca       562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta       610
```

-continued

```
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445
```

```
cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt cgt     2242
Lys Arg Gly Ser Gly Gln Ser Gly Pro Arg Gly Ala Pro Arg Gly Arg
        675                 680                 685

gga ggg ccc cca aga ccc aac aga ggg atg ccg caa atg aac act cag     2290
Gly Gly Pro Pro Arg Pro Asn Arg Gly Met Pro Gln Met Asn Thr Gln
    690                 695                 700

caa gtg aat taa tgtgatacac aggattatgt ttaatcgcca aaaacacact         2342
Gln Val Asn
705

ggccagtgta ccataatatg ttaccagaag agttattatc tatttgttct ccctttcagg   2402

aaacttattg taaagggact gttttcatcc cataaagaca ggactgcaat tgtcagcttt   2462

acattacctg gatatggaag gaaactattt ttattctgca tgttctgtcc taagcgtcat   2522

cttgagcctt gcacacaata caatactcag attcctcacc cttgcttagg agtaaaacat   2582

tatatactta tggggtgata atatctccat agttagttga agtggcttgg aaaaaaaatg   2642

caagattgaa tttttgacct tggataaaat ctacaatcag ccctagaact attcagtggt   2702
```

```
aattgacaaa gttaaagcat tttctttgaa aggaagatgg aaggagtgga gtgtggttta   2762
gcaaaactgc atttcatagc tttcccatta aattggagca ccgacagatt aaaagcatac   2822
caaattatgc atgggtcctt actcacacaa gtgaggctgg ctaccagcct tgacatagca   2882
ctcactagtc ttctggccaa acgactgtga ttaaaacaca tgtaaattgc tctttagtag   2942
tggatactgt gtaagacaaa gccaaattgc aaatcaggct ttgattggct cttctggaaa   3002
atatgcatca aatatggggg ataatctgga tgggctgctg ctgtgctcaa tgtgaactat   3062
ttagatacct ttggaacact taacagtttc tctgaacaat gacttacatg gggattggtc   3122
ctgtttgtca ttcctcacca taattgcatt gtcatcacta atccttggat cttgctgtat   3182
tgttactcaa attggtaata ggtactgatg gaaatcgcta atggatggat aatcataaca   3242
cttttggtca catgttttct cctgcagcct gaaagttctt aaagaaaaag atatcaaatg   3302
cctgctgcta ccaccctttt aaattgctat ctttagaaaa gcaccggtat gtgttttaga   3362
ttcatttccc tgttttaggg aaatgacagg cagtagtttc agttctgatg gcaaaacaaa   3422
taaaaacatg tttctaaaag ttgtatcttg aaacactggt gttcaacagc tagcagctaa   3482
agtaattcaa cccatgcatt gctagtgtca cagcctttgg ttatgtctag tagctgtttc   3542
tgaagtattt tcatttatct tttgtcaaat ttaaccctgt ttgaattctc tcctttcctc   3602
aaggagacac ttatgttcaa agtgttgatt ctttgcctta ggtgcataga gagtagacag   3662
tttggagatg gaaaggttag cagtgactta gccatatgtt ctgtgttgga atttgtgcta   3722
gcagtttgag cactagctct gcgtgcctat gaactgaatg ctgcttgtcc cattccattt   3782
tatgtcatgg agaaataatt ccacttggta acacaaaggc taagttaatg ttattttctg   3842
tacagaaatt aaattttact tttagccttt tgtaaacttt tttttttttt ttccaagccg   3902
gtatcagcta ctcaaaacaa ttctcagata ttcatcatta gacaactgga gtttttgctg   3962
gttttgtagc ctactaaaac tgctgaggct gttgaacatt ccacattcaa aagttttgta   4022
gggtggtgga taatggggaa gcttcaatgt ttattttaaa ataaataaaa taagttcttg   4082
acttttctca tgtgtggtta tggtacatca tattggaagg gttatctgtt tacttttgcc   4142
aagactattt tgccagcacc tacacttgtg tgctttaaaa gacaactacc tgggatgtac   4202
cacaaccata tgttaattgt attttattgg gatggataaa atgtttgtgg tttattggat   4262
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtcttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgccccccc   4802
ctcccccagg tagcatgcca ttgatgactt tttgcttagg gccattttat taccagggcc   4862
ttaatattcc taaaaagatg atttttttttc atcctttctc ctcttttgat cattgtatct   4922
tgatattaaa aacatgacct tccaatgatt gtagtaaatt aacttctata gttcttttgt   4982
ctctatatgt attcatatat atgctattgt atagagactt caaggagaca tggagatgca   5042
```

```
tgcttattct caggttcatt cactaaggtg cttggcagac aaccagtttc taagtgcaga   5102

atgtagttaa gcagcttcat atatgtgcca ggcaatttgt tttgttaaat tttcatctac   5162

ttaaggaaat agggtattgt agcttaggct gatcataccc ttcatttcaa ccttaagctc   5222

tcaacctgca tccatccgac ttgagctatt aagtacttta gttttatcga gtataagtta   5282

acagaaaaag taaattaagc tttgccttta ctattttgaa tttatataca ttctggaaaa   5342

acttagaaac tgttgtatat ttcattagat taaattatat gaaaatgtga ttgtttatag   5402

caaagcctgt gagttgcata caccctaagg aaaactcctt aagtgctcct tgaagagaga   5462

agaaacaatt ctgggtctgg tctttttaag aacaaagcta gactactgta tgttagcact   5522

gtacattaat agtctgttgt gaagcttgag cagtttcctg catagccttg atccttcacc   5582

gttggcattg aaaatagcag tatccctgat gtacttaaaa cttaaagtca ggttttggta   5642

tatttatttg taagtcttaa tttcctctaa atactatatc tctttagcga gacaacctga   5702

aatttattag cacatttggg tatctcttgc ttggcattat ggccagtgtt aactattcag   5762

tggtgaaaaa attacccctc aagacactgg agtgacccca gatgtgtgta gtaagtggca   5822

tggttcaact gtgtggttaa tgataaatat atgacttagt cggtatgatc tggaaagact   5882

tgattgaaag ataattcagc tgacataagg atgagtgagg agtggcaaac tggataaaag   5942

agtcaagaga cctgtattcc agtgactcct gttttgttta agcattagca agatctgtct   6002

ggggaaactg gatagggcag ttttcttcca tgtttagttt ttgtctcaac atttggaagc   6062

tattgaaggt tttaaaatgg tgtgtattgt tttttttgg gggggggtg gccagaatag   6122

tgggtcatct aataaaactg ccatttaaaa gatcaaaaaa aaaaaaaaaa aaaaaaaaa    6181
```

```
<210> SEQ ID NO 20
<211> LENGTH: 707
<212> TYPE: PRT
<213> ORGANISM: Mus musculus

<400> SEQUENCE: 20

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175
```

```
Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
```

```
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)

<400> SEQUENCE: 21

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt       651
```

```
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag       747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa       795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt       843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa       891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag       939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag       987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca      1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca      1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct      1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag      1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa      1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct      1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc      1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475
```

-continued

```
act aca gca tcc tca tcc ctt cct gct gct tct cag cct caa gtg ttc      1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680

gcc cca cga ggt cgt gga ggg ccc cca aga ccc aac aga ggg atg ccg      2235
Ala Pro Arg Gly Arg Gly Gly Pro Pro Arg Pro Asn Arg Gly Met Pro
    685                 690                 695

caa atg aac act cag caa gtg aat taa tgtgatacac aggattatgt          2282
Gln Met Asn Thr Gln Gln Val Asn
700                 705

ttaatcgcca aaaacacact ggccagtgta ccataatatg ttaccagaag agttattatc   2342

tatttgttct ccctttcagg aaacttattg taaagggact gttttcatcc cataaagaca   2402

ggactgcaat tgtcagcttt acattacctg gatatggaag gaaactattt ttattctgca   2462

tgttctgtcc taagcgtcat cttgagcctt gcacacaata caatactcag attcctcacc   2522

cttgcttagg agtaaaacat tatatactta tggggtgata atatctccat agttagttga   2582

agtggcttgg aaaaaaaatg caagattgaa tttttgacct tggataaaat ctacaatcag   2642

ccctagaact attcagtggt aattgacaaa gttaaagcat ttctctttgaa aggaagatgg  2702

aaggagtgga gtgtggttta gcaaaactgc atttcatagc tttcccatta aattggagca   2762

ccgacagatt aaaagcatac caaattatgc atgggtcctt actcacacaa gtgaggctgg   2822

ctaccagcct tgacatagca ctcactagtc ttctggccaa acgactgtga ttaaaacaca   2882
```

```
tgtaaattgc tctttagtag tggatactgt gtaagacaaa gccaaattgc aaatcaggct   2942
ttgattggct cttctggaaa atatgcatca aatatggggg ataatctgga tgggctgctg   3002
ctgtgctcaa tgtgaactat ttagatacct ttggaacact taacagtttc tctgaacaat   3062
gacttacatg ggattggtc ctgtttgtca ttcctcacca taattgcatt gtcatcacta   3122
atccttggat cttgctgtat tgttactcaa attggtaata ggtactgatg gaaatcgcta   3182
atggatggat aatcataaca cttttggtca catgttttct cctgcagcct gaaagttctt   3242
aaagaaaaag atatcaaatg cctgctgcta ccaccctttt aaattgctat ctttagaaaa   3302
gcaccggtat gtgttttaga ttcatttccc tgttttaggg aaatgacagg cagtagtttc   3362
agttctgatg gcaaaacaaa taaaaacatg tttctaaaag ttgtatcttg aaacactggt   3422
gttcaacagc tagcagctaa agtaattcaa cccatgcatt gctagtgtca cagcctttgg   3482
ttatgtctag tagctgtttc tgaagtattt tcatttatct tttgtcaaat ttaaccctgt   3542
ttgaattctc tcctttcctc aaggagacac ttatgttcaa agtgttgatt ctttgcctta   3602
ggtgcataga gagtagacag tttggagatg gaaaggttag cagtgactta gccatatgtt   3662
ctgtgttgga atttgtgcta gcagtttgag cactagctct gcgtgcctat gaactgaatg   3722
ctgcttgtcc cattccattt tatgtcatgg agaaataatt ccacttggta acacaaaggc   3782
taagttaatg ttattttctg tacagaaatt aaattttact tttagccttt tgtaaacttt   3842
tttttttttt ttccaagccg gtatcagcta ctcaaaacaa ttctcagata ttcatcatta   3902
gacaactgga gtttttgctg gttttgtagc ctactaaaac tgctgaggct gttgaacatt   3962
ccacattcaa aagttttgta gggtggtgga taatggggaa gcttcaatgt ttattttaaa   4022
ataaataaaa taagttcttg acttttctca tgtgtggtta tggtacatca tattggaagg   4082
gttatctgtt tacttttgcc aagactattt tgccagcacc tacacttgtg tgctttaaaa   4142
gacaactacc tgggatgtac cacaaccata tgttaattgt attttattgg gatggataaa   4202
atgtttgtgg tttattggat aatccctaga tggtgtgtta cgtgtgtaga atataatttt   4262
atgatagtaa gaaagcaaaa ttgaagaaaa taagtttagt attgaatttg agttctgaag   4322
tgaattcagg gaatgtctca cgtttcgggc ttctacccaa agtgtagggc agaaggtgta   4382
aaagttgttt gtagtttgac ttgtttattt tttaagttgc ttattccttt caacagcaac   4442
atatcattag ctgtcattct accattgcag ttctagtgag ttttaacgtc tgcattcaag   4502
actgttttaa aagcaacctc actggacaga gaactgctaa agtcttttcc ttaagatctg   4562
agtctttgtt actcagtatc ttctataata tgcaaatgct tgtctagagg cagaagacct   4622
tttgtttggt caagtgtgta ttttaccaga gtacagggaa ctgatggtcc tacatgtctc   4682
ttagtgtagt aagactataa aatcttttgt acatgcacaa ttcacagtat gtttagatac   4742
cacgtgtata atgccccccc ctcccccagg tagcatgcca ttgatgactt tttgcttagg   4802
gccattttat taccagggcc ttaatattcc taaaaagatg atttttttc atcctttctc   4862
ctcttttgat cattgtatct tgatattaaa aacatgacct tccaatgatt gtagtaaatt   4922
aacttctata gttcttttgt ctctatatgt attcatatat atgctattgt atagagactt   4982
caaggagaca tggagatgca tgcttattct caggttcatt cactaaggtg cttggcagac   5042
aaccagtttc taagtgcaga atgtagttaa gcagcttcat atatgtgcca ggcaatttgt   5102
tttgttaaat tttcatctac ttaaggaaat agggtattgt agcttaggct gatcataccc   5162
ttcatttcaa ccttaagctc tcaacctgca tccatccgac ttgagctatt aagtacttta   5222
```

```
gttttatcga gtataagtta acagaaaaag taaattaagc tttgccttta ctattttgaa   5282

tttatataca ttctggaaaa acttagaaac tgttgtatat ttcattagat taaattatat   5342

gaaaatgtga ttgtttatag caaagcctgt gagttgcata caccctaagg aaaactcctt   5402

aagtgctcct tgaagagaga agaaacaatt ctgggtctgg tctttttaag aacaaagcta   5462

gactactgta tgttagcact gtacattaat agtctgttgt gaagcttgag cagtttcctg   5522

catagccttg atccttcacc gttggcattg aaaatagcag tatccctgat gtacttaaaa   5582

cttaaagtca ggttttggta tatttatttg taagtcttaa tttcctctaa atactatatc   5642

tctttagcga gacaacctga aatttattag cacatttggg tatctcttgc ttggcattat   5702

ggccagtgtt aactattcag tggtgaaaaa attacccctc aagacactgg agtgacccca   5762

gatgtgtgta gtaagtggca tggttcaact gtgtggttaa tgataaatat atgacttagt   5822

cggtatgatc tggaaagact tgattgaaag ataattcagc tgacataagg atgagtgagg   5882

agtggcaaac tggataaaag agtcaagaga cctgtattcc agtgactcct gttttgttta   5942

agcattagca agatctgtct ggggaaactg gatagggcag ttttcttcca tgtttagttt   6002

ttgtctcaac atttggaagc tattgaaggt tttaaaatgg tgtgtattgt tttttttgg   6062

ggggggggtg gccagaatag tggtcatct aataaaactg ccatttaaaa gatcaaaaaa   6122

aaaaaaaaaa aaaaaaaaa                                                6141
```

```
<210> SEQ ID NO 22
<211> LENGTH: 707
<212> TYPE: PRT
<213> ORGANISM: Mus musculus

<400> SEQUENCE: 22

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205
```

```
Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
```

```
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)

<400> SEQUENCE: 23

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc      171
                    Met Pro Ser Ala Thr Ser His Ser Gly Ser Gly
                    1               5                   10

agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185
```

```
tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag acg ctt gat cct gcc att gta     1275
Met Gln Gly Pro Tyr Asn Phe Ile Gln Thr Leu Asp Pro Ala Ile Val
    365                 370                 375

tcc gca cag cct atg aac cct acc cag aac atg gat atg cct cag ctg     1323
Ser Ala Gln Pro Met Asn Pro Thr Gln Asn Met Asp Met Pro Gln Leu
380                 385                 390                 395

gtt tgc cct cag gtt cat tct gaa tct aga ctt gcc caa tct aat caa     1371
Val Cys Pro Gln Val His Ser Glu Ser Arg Leu Ala Gln Ser Asn Gln
                400                 405                 410

gtt cct gta caa cca gaa gcc aca cag gtt cct ttg gtt tca tcc aca     1419
Val Pro Val Gln Pro Glu Ala Thr Gln Val Pro Leu Val Ser Ser Thr
            415                 420                 425

agt gag ggg tat aca gca tct cag ccc ttg tac cag cca tct cat gct     1467
Ser Glu Gly Tyr Thr Ala Ser Gln Pro Leu Tyr Gln Pro Ser His Ala
        430                 435                 440

acg gag cag cgg ccg cag aaa gag cca atg gat cag att cag gca aca     1515
Thr Glu Gln Arg Pro Gln Lys Glu Pro Met Asp Gln Ile Gln Ala Thr
    445                 450                 455

ata tct ttg aat aca gac cag act aca gca tcc tca tcc ctt cct gct     1563
Ile Ser Leu Asn Thr Asp Gln Thr Thr Ala Ser Ser Ser Leu Pro Ala
460                 465                 470                 475

gct tct cag cct caa gtg ttc cag gct ggg aca agt aaa cct ttg cac     1611
Ala Ser Gln Pro Gln Val Phe Gln Ala Gly Thr Ser Lys Pro Leu His
                480                 485                 490

agc agt gga atc aat gta aat gca gct cca ttc cag tcc atg caa acg     1659
Ser Ser Gly Ile Asn Val Asn Ala Ala Pro Phe Gln Ser Met Gln Thr
```

-continued

```
            495                 500                 505

gtg ttc aat atg aat gct cca gtc cct cct gct aat gaa cca gaa acg      1707
Val Phe Asn Met Asn Ala Pro Val Pro Pro Ala Asn Glu Pro Glu Thr
        510                 515                 520

tta aaa caa cag agt cag tac cag gcc act tat aac cag agt ttt tcc      1755
Leu Lys Gln Gln Ser Gln Tyr Gln Ala Thr Tyr Asn Gln Ser Phe Ser
    525                 530                 535

agt cag cct cac caa gtg gaa caa aca gag ctt caa caa gac caa ctg      1803
Ser Gln Pro His Gln Val Glu Gln Thr Glu Leu Gln Gln Asp Gln Leu
540                 545                 550                 555

caa acg gtg gtt ggc act tac cat gga tcc cag gac cag cct cat caa      1851
Gln Thr Val Val Gly Thr Tyr His Gly Ser Gln Asp Gln Pro His Gln
                560                 565                 570

gtg cct ggt aac cac cag caa ccc cca cag cag aac act ggc ttt cca      1899
Val Pro Gly Asn His Gln Gln Pro Pro Gln Gln Asn Thr Gly Phe Pro
            575                 580                 585

cgt agc agt cag cct tat tac aac agt cgt ggg gta tct cga gga ggg      1947
Arg Ser Ser Gln Pro Tyr Tyr Asn Ser Arg Gly Val Ser Arg Gly Gly
        590                 595                 600

tct cgt ggt gcc aga ggc ttg atg aat gga tac agg ggc cct gcc aat      1995
Ser Arg Gly Ala Arg Gly Leu Met Asn Gly Tyr Arg Gly Pro Ala Asn
    605                 610                 615

gga ttt aga gga gga tat gat ggt tac cgc cct tca ttc tcg aac act      2043
Gly Phe Arg Gly Gly Tyr Asp Gly Tyr Arg Pro Ser Phe Ser Asn Thr
620                 625                 630                 635

cca aac agt ggt tat tca cag tct cag ttc act gct ccc cgg gac tac      2091
Pro Asn Ser Gly Tyr Ser Gln Ser Gln Phe Thr Ala Pro Arg Asp Tyr
                640                 645                 650

tct ggt tac cag cgg gat gga tat cag cag aat ttc aag cga ggc tct      2139
Ser Gly Tyr Gln Arg Asp Gly Tyr Gln Gln Asn Phe Lys Arg Gly Ser
            655                 660                 665

ggg cag agt gga cca cgg gga gcc cca cga ggt cgt gga ggg ccc cca      2187
Gly Gln Ser Gly Pro Arg Gly Ala Pro Arg Gly Arg Gly Gly Pro Pro
        670                 675                 680

aga ccc aac aga ggg atg ccg caa atg aac act cag caa gtg aat taa      2235
Arg Pro Asn Arg Gly Met Pro Gln Met Asn Thr Gln Gln Val Asn
    685                 690                 695

tgtgatacac aggattatgt ttaatcgcca aaaacacact ggccagtgta ccataatatg    2295

ttaccagaag agttattatc tatttgttct ccctttcagg aaacttattg taaagggact    2355

gttttcatcc cataaagaca ggactgcaat tgtcagcttt acattacctg gatatggaag    2415

gaaactattt ttattctgca tgttctgtcc taagcgtcat cttgagcctt gcacacaata    2475

caatactcag attcctcacc cttgcttagg agtaaaacat tatatactta tggggtgata    2535

atatctccat agttagttga agtggcttgg aaaaaaaatg caagattgaa tttttgacct    2595

tggataaaat ctacaatcag ccctagaact attcagtggt aattgacaaa gttaaagcat    2655

tttctttgaa aggaagatgg aaggagtgga gtgtggttta gcaaaactgc atttcatagc    2715

tttcccatta aattggagca ccgacagatt aaaagcatac caaattatgc atgggtcctt    2775

actcacacaa gtgaggctgg ctaccagcct tgacatagca ctcactagtc ttctggccaa    2835

acgactgtga ttaaaacaca tgtaaattgc tctttagtag tggatactgt gtaagacaaa    2895

gccaaattgc aaatcaggct ttgattggct cttctggaaa atatgcatca aatatggggg    2955

ataatctgga tgggctgctg ctgtgctcaa tgtgaactat ttagatacct ttggaacact    3015

taacagtttc tctgaacaat gacttacatg gggattggtc ctgtttgtca ttcctcacca    3075

taattgcatt gtcatcacta atccttggat cttgctgtat tgttactcaa attggtaata    3135
```

```
ggtactgatg gaaatcgcta atggatggat aatcataaca cttttggtca catgttttct   3195
cctgcagcct gaaagttctt aaagaaaaag atatcaaatg cctgctgcta ccaccctttt   3255
aaattgctat ctttagaaaa gcaccggtat gtgttttaga ttcatttccc tgttttaggg   3315
aaatgacagg cagtagtttc agttctgatg gcaaaacaaa taaaaacatg tttctaaaag   3375
ttgtatcttg aaacactggt gttcaacagc tagcagctaa agtaattcaa cccatgcatt   3435
gctagtgtca cagcctttgg ttatgtctag tagctgtttc tgaagtattt tcatttatct   3495
tttgtcaaat ttaaccctgt ttgaattctc tcctttcctc aaggagacac ttatgttcaa   3555
agtgttgatt ctttgcctta ggtgcataga gagtagacag tttggagatg gaaaggttag   3615
cagtgactta gccatatgtt ctgtgttgga atttgtgcta gcagtttgag cactagctct   3675
gcgtgcctat gaactgaatg ctgcttgtcc cattccattt tatgtcatgg agaaataatt   3735
ccacttggta acacaaaggc taagttaatg ttattttctg tacagaaatt aaattttact   3795
tttagccttt tgtaaacttt tttttttttt ttccaagccg gtatcagcta ctcaaaacaa   3855
ttctcagata ttcatcatta gacaactgga gtttttgctg gttttgtagc ctactaaaac   3915
tgctgaggct gttgaacatt ccacattcaa aagttttgta gggtggtgga taatggggaa   3975
gcttcaatgt ttattttaaa ataaataaaa taagttcttg acttttctca tgtgtggtta   4035
tggtacatca tattggaagg gttatctgtt tacttttgcc aagactattt tgccagcacc   4095
tacacttgtg tgctttaaaa gacaactacc tgggatgtac cacaaccata tgttaattgt   4155
attttattgg gatggataaa atgtttgtgg tttattggat aatccctaga tggtgtgtta   4215
cgtgtgtaga atataatttt atgatagtaa gaaagcaaaa ttgaagaaaa taagtttagt   4275
attgaatttg agttctgaag tgaattcagg gaatgtctca cgtttcgggc ttctacccaa   4335
agtgtagggc agaaggtgta aaagttgttt gtagtttgac ttgtttattt tttaagttgc   4395
ttattccttt caacagcaac atatcattag ctgtcattct accattgcag ttctagtgag   4455
ttttaacgtc tgcattcaag actgttttaa aagcaacctc actggacaga gaactgctaa   4515
agtcttttcc ttaagatctg agtctttgtt actcagtatc ttctataata tgcaaatgct   4575
tgtctagagg cagaagacct tttgtttggt caagtgtgta ttttaccaga gtacagggaa   4635
ctgatggtcc tacatgtctc ttagtgtagt aagactataa aatcttttgt acatgcacaa   4695
ttcacagtat gtttagatac cacgtgtata atgccccccc ctcccccagg tagcatgcca   4755
ttgatgactt tttgcttagg gccattttat taccagggcc ttaatattcc taaaaagatg   4815
atttttttttc atcctttctc ctcttttgat cattgtatct tgatattaaa aacatgacct   4875
tccaatgatt gtagtaaatt aacttctata gttcttttgt ctctatatgt attcatatat   4935
atgctattgt atagagactt caaggagaca tggagatgca tgcttattct caggttcatt   4995
cactaaggtg cttggcagac aaccagtttc taagtgcaga atgtagttaa gcagcttcat   5055
atatgtgcca ggcaatttgt tttgttaaat tttcatctac ttaaggaaat agggtattgt   5115
agcttaggct gatcataccc ttcatttcaa ccttaagctc tcaacctgca tccatccgac   5175
ttgagctatt aagtacttta gttttatcga gtataagtta acagaaaaag taaattaagc   5235
tttgccttta ctattttgaa tttatataca ttctggaaaa acttagaaac tgttgtatat   5295
ttcattagat taaattatat gaaaatgtga ttgtttatag caaagcctgt gagttgcata   5355
caccctaagg aaaactcctt aagtgctcct tgaagagaga agaaacaatt ctgggtctgg   5415
tctttttaag aacaaagcta gactactgta tgttagcact gtacattaat agtctgttgt   5475
```

```
gaagcttgag cagtttcctg catagccttg atccttcacc gttggcattg aaaatagcag   5535
tatccctgat gtacttaaaa cttaaagtca ggttttggta tatttatttg taagtcttaa   5595
tttcctctaa atactatatc tctttagcga gacaacctga aatttattag cacatttggg   5655
tatctcttgc ttggcattat ggccagtgtt aactattcag tggtgaaaaa attacccctc   5715
aagacactgg agtgacccca gatgtgtgta gtaagtggca tggttcaact gtgtggttaa   5775
tgataaatat atgacttagt cggtatgatc tggaaagact tgattgaaag ataattcagc   5835
tgacataagg atgagtgagg agtggcaaac tggataaaag agtcaagaga cctgtattcc   5895
agtgactcct gttttgttta agcattagca agatctgtct ggggaaactg gatagggcag   5955
ttttcttcca tgtttagttt ttgtctcaac atttggaagc tattgaaggt tttaaaatgg   6015
tgtgtattgt tttttttgg ggggggggtg gccagaatag tgggtcatct aataaaactg   6075
ccatttaaaa gatcaaaaaa aaaaaaaaaa aaaaaaaaa                          6114
```

```
<210> SEQ ID NO 24
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
```

```
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
                405                 410                 415

Glu Ala Thr Gln Val Pro Leu Val Ser Ser Thr Ser Glu Gly Tyr Thr
            420                 425                 430

Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Ser Gln Pro His Gln
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
            660                 665                 670

Arg Gly Ala Pro Arg Gly Arg Gly Gly Pro Pro Arg Pro Asn Arg Gly
        675                 680                 685
```

```
Met Pro Gln Met Asn Thr Gln Gln Val Asn
    690                 695


<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)

<400> SEQUENCE: 25

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc cccctcggc tgcccactcc agacgtccag cggctccgcg cgcgcacg        178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg       370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg       514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca       562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta       610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat       658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg       706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat       754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc       802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt       850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag       898
Gly Thr Thr Tyr Lys Ala Leu Lys Glu Ile Val Glu Arg Val Phe Gln
```

```
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
```

-continued

```
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt aat     2242
Lys Arg Gly Ser Gly Gln Ser Gly Pro Arg Gly Ala Pro Arg Gly Asn
        675                 680                 685

ata ttg tgg tgg tga tcctagctcc tatgtggagc ttctgttctg gccttggaag     2297
Ile Leu Trp Trp
    690

aactgttcat agtccgcatg taggttacat gttaggaata catttatctt ttccagactt   2357

gttgctaaag attaaatgaa atgctctgtt tctaaaattt catcttgaat ccaaatttta   2417

atttttgaat gactttccct gctgttgtct tcaaaatcag aacattttct ctgcctcaga   2477

aaagcgtttt tccaactgga aatttatttt tcaggtctta aaacctgcta aatgttttta   2537

ggaagtacct actgaaactt tttgtaagac atttttggaa cgagcttgaa catttatata   2597

aatttattac cctctttgat ttttgaaaca tgcatattat atttaggctg agaagccctt   2657

caaatggcca gataagccac agttttagct agagaaccat ttagaattga cataactaat   2717

ctaaacttga acacttttag gaccaatgtt agtgttctaa ataccaacat atttctgatg   2777

tttaaacaga tctcccaaat tcttaggacc ttgatgtcat taaaatttag aatgacaagc   2837

ttaagaggct ttagtttcat ttgtttttca agtaatgaaa aataatttct tacatgggca   2897

gatagttaat ttgttgaaca attacaggta gcatttcatg taatctgatg ttctaaatgg   2957

ttctcttatt gaaggaggtt aaagaattag gtttcttaca gtttttggct ggccatgaca   3017

tgtataaaat gtatattaag gaggaattat aaagtacttt aatttgaatg ctagtggcaa   3077

ttgatcatta agaaagtact ttaaagcaaa aggttaatgg gtcatctggg aaaaatactg   3137

aagtatcaaa ggtatttgca tgtgaatgtg ggttatgttc ttctatccca ccttgtagca   3197

tattctatga aagttgagtt aaatgatagc taaaatatct gtttcaacag catgtaaaaa   3257

gttattttaa ctgttacaag tcattataca attttgaatg ttctgtagtt tctttttaac   3317

agtttaggta caaaggtctg ttttcattct ggtgcttttt attaattttg atagtatgat   3377

gtcacttcct attgaaatgt aagctagcgt gtaccttaga atgtgagctc catgagagca   3437

ggtaccttgt ttgtcttcac tgctgtatct attcccaacg cctcatgaca gtgcctggca   3497
```

```
catagtaggc actcaataaa tacttgttga atgaatgaaa aaaaaaaaaa a          3548


<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365
```

```
Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690
```

<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)

<400> SEQUENCE: 27

```
cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
```

-continued

```
                  Met Pro Ser Ala Thr Ser His Ser Gly Ser Gly
                  1               5                   10

agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315
```

-continued

```
gtt gaa aca gtt gag gtt gta aac tca ctc cag cag caa cct cag gct      1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag      1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa      1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct      1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc      1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc      1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635
```

```
ggt tac cgc cct tca ttc tcg aac act cca aac agt ggt tat tca cag     2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga     2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga     2187
Tyr Gln Gln Asn Phe Lys Arg Gly Ser Gly Gln Ser Gly Pro Arg Gly
        670                 675                 680

gcc cca cga ggt aat ata ttg tgg tgg tga tcctagctcc tatgtggagc       2237
Ala Pro Arg Gly Asn Ile Leu Trp Trp
    685                 690

ttctgttctg gccttggaag aactgttcat agtccgcatg taggttacat gttaggaata   2297

catttatctt ttccagactt gttgctaaag attaaatgaa atgctctgtt tctaaaattt   2357

catcttgaat ccaaatttta atttttgaat gactttccct gctgttgtct tcaaaatcag   2417

aacattttct ctgcctcaga aaagcgtttt tccaactgga aatttatttt tcaggtctta   2477

aaacctgcta aatgttttta ggaagtacct actgaaactt tttgtaagac atttttggaa   2537

cgagcttgaa catttatata aatttattac cctctttgat ttttgaaaca tgcatattat   2597

atttaggctg agaagccctt caaatggcca gataagccac agttttagct agagaaccat   2657

ttagaattga cataactaat ctaaacttga acacttttag gaccaatgtt agtgttctaa   2717

ataccaacat atttctgatg tttaaacaga tctcccaaat tcttaggacc ttgatgtcat   2777

taaaatttag aatgacaagc ttaagaggct ttagtttcat ttgtttttca agtaatgaaa   2837

aataatttct tacatgggca gatagttaat ttgttgaaca attacaggta gcatttcatg   2897

taatctgatg ttctaaatgg ttctcttatt gaaggaggtt aaagaattag gtttcttaca   2957

gtttttggct ggccatgaca tgtataaaat gtatattaag gaggaattat aaagtacttt   3017

aatttgaatg ctagtggcaa ttgatcatta agaaagtact ttaaagcaaa aggttaatgg   3077

gtcatctggg aaaaatactg aagtatcaaa ggtatttgca tgtgaatgtg ggttatgttc   3137

ttctatccca ccttgtagca tattctatga aagttgagtt aaatgatagc taaaatatct   3197

gtttcaacag catgtaaaaa gttattttaa ctgttacaag tcattataca attttgaatg   3257

ttctgtagtt tctttttaac agtttaggta caaaggtctg ttttcattct ggtgcttttt   3317

attaattttg atagtatgat gtcacttcct attgaaatgt aagctagcgt gtaccttaga   3377

atgtgagctc catgagagca ggtaccttgt ttgtcttcac tgctgtatct attcccaacg   3437

cctcatgaca gtgcctggca catagtaggc actcaataaa tacttgttga atgaatgaaa   3497

aaaaaaaaaa a                                                        3508
```

```
<210> SEQ ID NO 28
<211> LENGTH: 692
<212> TYPE: PRT
<213> ORGANISM: Mus musculus

<400> SEQUENCE: 28

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
```

```
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480
```

```
Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)

<400> SEQUENCE: 29

atg ccc tcg gct acc aac ggc acc atg gcg agc agc agc ggg aag gcg       48
Met Pro Ser Ala Thr Asn Gly Thr Met Ala Ser Ser Ser Gly Lys Ala
1               5                   10                  15

ggc ccg ggc ggc aac gag cag gcc ccg gcg gcg gca gcg gcg gcc ccg       96
Gly Pro Gly Gly Asn Glu Gln Ala Pro Ala Ala Ala Ala Ala Ala Pro
            20                  25                  30

cag gcg tcg ggc ggc agc atc acc tcg gtt cag acc gag gcc atg aag      144
Gln Ala Ser Gly Gly Ser Ile Thr Ser Val Gln Thr Glu Ala Met Lys
        35                  40                  45

cag atc ttg gga gtg atc gac aaa aag ctc cgc aac ctc gag aag aaa      192
Gln Ile Leu Gly Val Ile Asp Lys Lys Leu Arg Asn Leu Glu Lys Lys
    50                  55                  60

aag agc aaa ctt gac gat tac cag gaa cga atg aac aag ggg gaa cgt      240
Lys Ser Lys Leu Asp Asp Tyr Gln Glu Arg Met Asn Lys Gly Glu Arg
65                  70                  75                  80

cta aat caa gat caa ctg gat gca gtg tca aaa tac cag gaa gtg aca      288
Leu Asn Gln Asp Gln Leu Asp Ala Val Ser Lys Tyr Gln Glu Val Thr
                85                  90                  95

aat aac ctg gaa ttc gct aaa gaa ctg cag agg agc ttt atg gca ctg      336
```

```
Asn Asn Leu Glu Phe Ala Lys Glu Leu Gln Arg Ser Phe Met Ala Leu
            100                 105                 110

agc caa gat atc cag aaa aca ata aaa aag acg gct cgc agg gag cag      384
Ser Gln Asp Ile Gln Lys Thr Ile Lys Lys Thr Ala Arg Arg Glu Gln
        115                 120                 125

ctg atg aga gaa gag gct gag cag aag cgt tta aag act gtg cta gag      432
Leu Met Arg Glu Glu Ala Glu Gln Lys Arg Leu Lys Thr Val Leu Glu
    130                 135                 140

ctg cag ttc att ttg gac aag ttg ggt gac gat gaa gtg cgc agt gac      480
Leu Gln Phe Ile Leu Asp Lys Leu Gly Asp Asp Glu Val Arg Ser Asp
145                 150                 155                 160

ttg aaa caa gga tca aat gga gta ccg gta ctg aca gag gag gaa ctg      528
Leu Lys Gln Gly Ser Asn Gly Val Pro Val Leu Thr Glu Glu Glu Leu
                165                 170                 175

aca atg ctg gat gaa ttt tac aag cta gtt tac cct gaa agg gac atg      576
Thr Met Leu Asp Glu Phe Tyr Lys Leu Val Tyr Pro Glu Arg Asp Met
            180                 185                 190

aac atg agg ttg aat gag cag tat gag caa gca tct gtt cac ctg tgg      624
Asn Met Arg Leu Asn Glu Gln Tyr Glu Gln Ala Ser Val His Leu Trp
        195                 200                 205

gac tta ctg gaa ggg aag gaa aaa ccc gtt tgt gga aca acc tat aaa      672
Asp Leu Leu Glu Gly Lys Glu Lys Pro Val Cys Gly Thr Thr Tyr Lys
    210                 215                 220

gcc ctg aag gag gtt gtt gaa cgt att ctt caa act agt tac ttt gat      720
Ala Leu Lys Glu Val Val Glu Arg Ile Leu Gln Thr Ser Tyr Phe Asp
225                 230                 235                 240

agc acc cat aac cat cag aac ggg tta tgt gag gaa gaa gag gca gca      768
Ser Thr His Asn His Gln Asn Gly Leu Cys Glu Glu Glu Glu Ala Ala
                245                 250                 255

ccc aca cct gca gta gaa gac act gta gca gaa gct gag cct gat cca      816
Pro Thr Pro Ala Val Glu Asp Thr Val Ala Glu Ala Glu Pro Asp Pro
            260                 265                 270

gca gaa gaa ttt act gaa cct act gaa gtt gaa tcg act gag tat gta      864
Ala Glu Glu Phe Thr Glu Pro Thr Glu Val Glu Ser Thr Glu Tyr Val
        275                 280                 285

aac aga caa ttc atg gca gag act cag ttc agc agt agt gag aag gaa      912
Asn Arg Gln Phe Met Ala Glu Thr Gln Phe Ser Ser Ser Glu Lys Glu
    290                 295                 300

cag gta gat gag tgg aca gtt gaa acg gtt gag gtt gta aat tca ctg      960
Gln Val Asp Glu Trp Thr Val Glu Thr Val Glu Val Val Asn Ser Leu
305                 310                 315                 320

cag caa caa aca caa gct aca tct cct cca gtt cct gaa cct cat aca     1008
Gln Gln Gln Thr Gln Ala Thr Ser Pro Pro Val Pro Glu Pro His Thr
                325                 330                 335

ctc act act gtg gct caa gca gat cct ctt gtt aga aga cag aga gta     1056
Leu Thr Thr Val Ala Gln Ala Asp Pro Leu Val Arg Arg Gln Arg Val
            340                 345                 350

cag gac ctt atg gcc cag atg cag ggt cca tat aac ttc atg cag gac     1104
Gln Asp Leu Met Ala Gln Met Gln Gly Pro Tyr Asn Phe Met Gln Asp
        355                 360                 365

tct atg ctg gag ttt gag aac cag aca ctt gat cct gcc att gta tct     1152
Ser Met Leu Glu Phe Glu Asn Gln Thr Leu Asp Pro Ala Ile Val Ser
    370                 375                 380

gca cag ccc atg aat cca gca cag aat ttg gac atg ccg caa atg gtc     1200
Ala Gln Pro Met Asn Pro Ala Gln Asn Leu Asp Met Pro Gln Met Val
385                 390                 395                 400

tgc cct cca gtt cat act gag tca aga ctt gcc cag cct aat caa gtt     1248
Cys Pro Pro Val His Thr Glu Ser Arg Leu Ala Gln Pro Asn Gln Val
                405                 410                 415
```

```
cct gtg caa cca gaa gct acg cag gtt ccc ttg gtt tca tct aca agt      1296
Pro Val Gln Pro Glu Ala Thr Gln Val Pro Leu Val Ser Ser Thr Ser
            420                 425                 430

gag gga tat aca gcc tcc cag ccc atg tat cag cct tct cat acc aca      1344
Glu Gly Tyr Thr Ala Ser Gln Pro Met Tyr Gln Pro Ser His Thr Thr
        435                 440                 445

gag caa cgg cca cag aag gaa tcc att gac cag att cag gct tca atg      1392
Glu Gln Arg Pro Gln Lys Glu Ser Ile Asp Gln Ile Gln Ala Ser Met
    450                 455                 460

tca ctg aat gca gac cag acc ccg tca tca tca tca ctt ccc act gca      1440
Ser Leu Asn Ala Asp Gln Thr Pro Ser Ser Ser Ser Leu Pro Thr Ala
465                 470                 475                 480

tcc cag ccg caa gtt ttc caa gct gga tct agc aaa cct ttg cat agc      1488
Ser Gln Pro Gln Val Phe Gln Ala Gly Ser Ser Lys Pro Leu His Ser
                485                 490                 495

agc gga atc aat gtt aat gca gct cca ttc caa tcc atg caa aca gta      1536
Ser Gly Ile Asn Val Asn Ala Ala Pro Phe Gln Ser Met Gln Thr Val
            500                 505                 510

ttc aac atg aat gca cct gtt cct cct gtt aat gag cca gaa gcc ctt      1584
Phe Asn Met Asn Ala Pro Val Pro Pro Val Asn Glu Pro Glu Ala Leu
        515                 520                 525

aag caa caa aat cag tac cag gcc agt tac aac cag agt ttc tcc aat      1632
Lys Gln Gln Asn Gln Tyr Gln Ala Ser Tyr Asn Gln Ser Phe Ser Asn
    530                 535                 540

cag cca cac caa gta gaa caa tca gat ctt cag caa gaa cag ctc cag      1680
Gln Pro His Gln Val Glu Gln Ser Asp Leu Gln Gln Glu Gln Leu Gln
545                 550                 555                 560

aca gtg gtt ggt act tac cat ggt tct ccg gac cag acc cat caa gtg      1728
Thr Val Val Gly Thr Tyr His Gly Ser Pro Asp Gln Thr His Gln Val
                565                 570                 575

gca gga aac cac cag caa cct ccc cag cag aat act gga ttt cca cgc      1776
Ala Gly Asn His Gln Gln Pro Pro Gln Gln Asn Thr Gly Phe Pro Arg
            580                 585                 590

aac agt cag cct tat tac aac agt cgg gga gtg tct cgt ggt gga tca      1824
Asn Ser Gln Pro Tyr Tyr Asn Ser Arg Gly Val Ser Arg Gly Gly Ser
        595                 600                 605

cgt ggg act cgt gga ttg atg aat ggt tac agg gga cct gca aat gga      1872
Arg Gly Thr Arg Gly Leu Met Asn Gly Tyr Arg Gly Pro Ala Asn Gly
    610                 615                 620

ttt aga gga gga tat gat ggc tac cgt cct tca ttt tcc aac act ccg      1920
Phe Arg Gly Gly Tyr Asp Gly Tyr Arg Pro Ser Phe Ser Asn Thr Pro
625                 630                 635                 640

aac agt ggt tac acg cag ccc caa ttt aat gct cct cga gat tat tca      1968
Asn Ser Gly Tyr Thr Gln Pro Gln Phe Asn Ala Pro Arg Asp Tyr Ser
                645                 650                 655

aac tac cag cgg gat gga tat cag cag aac ttc aaa cgt ggt tct gga      2016
Asn Tyr Gln Arg Asp Gly Tyr Gln Gln Asn Phe Lys Arg Gly Ser Gly
            660                 665                 670

caa agt ggg cct cgg gga gct cct cga ggt cgt gga ggg ccc cca aga      2064
Gln Ser Gly Pro Arg Gly Ala Pro Arg Gly Arg Gly Gly Pro Pro Arg
        675                 680                 685

cca aac aga ggg atg cct caa atg aac gct cag caa gtg aat taa          2109
Pro Asn Arg Gly Met Pro Gln Met Asn Ala Gln Gln Val Asn
    690                 695                 700


<210> SEQ ID NO 30
<211> LENGTH: 702
<212> TYPE: PRT
<213> ORGANISM: Gallus gallus

<400> SEQUENCE: 30
```

```
Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Glu Ala Ala
                245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Ser Glu Lys Glu
    290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
        355                 360                 365

Ser Met Leu Glu Phe Glu Asn Gln Thr Leu Asp Pro Ala Ile Val Ser
    370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415
```

```
Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
        435                 440                 445

Glu Gln Arg Pro Gln Lys Glu Ser Ile Asp Gln Ile Gln Ala Ser Met
    450                 455                 460

Ser Leu Asn Ala Asp Gln Thr Pro Ser Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
            500                 505                 510

Phe Asn Met Asn Ala Pro Val Pro Pro Val Asn Glu Pro Glu Ala Leu
        515                 520                 525

Lys Gln Gln Asn Gln Tyr Gln Ala Ser Tyr Asn Gln Ser Phe Ser Asn
    530                 535                 540

Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
        595                 600                 605

Arg Gly Thr Arg Gly Leu Met Asn Gly Tyr Arg Gly Pro Ala Asn Gly
    610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
                645                 650                 655

Asn Tyr Gln Arg Asp Gly Tyr Gln Gln Asn Phe Lys Arg Gly Ser Gly
            660                 665                 670

Gln Ser Gly Pro Arg Gly Ala Pro Arg Gly Arg Gly Gly Pro Pro Arg
        675                 680                 685

Pro Asn Arg Gly Met Pro Gln Met Asn Ala Gln Gln Val Asn
    690                 695                 700


<210> SEQ ID NO 31
<211> LENGTH: 63
<212> TYPE: PRT
<213> ORGANISM: Homo sapiens

<400> SEQUENCE: 31

Glu Glu Tyr Thr Glu Gln Ser Glu Val Glu Ser Thr Glu Tyr Val Asn
1               5                   10                  15

Arg Gln Phe Met Ala Glu Thr Gln Phe Thr Ser Gly Glu Lys Glu Gln
            20                  25                  30

Val Asp Glu Trp Thr Val Glu Thr Val Glu Val Val Asn Ser Leu Gln
        35                  40                  45

Gln Gln Pro Gln Ala Ala Ser Pro Ser Val Pro Glu Pro His Ser
    50                  55                  60


<210> SEQ ID NO 32
<211> LENGTH: 18
<212> TYPE: PRT
<213> ORGANISM: Homo sapiens
```

<400> SEQUENCE: 32

```
Val Phe Asn Met Asn Ala Pro Val Pro Pro Val Asn Glu Pro Glu Thr
1               5                   10                  15

Leu Lys
```

<210> SEQ ID NO 33
<211> LENGTH: 16
<212> TYPE: PRT
<213> ORGANISM: Homo sapiens

<400> SEQUENCE: 33

```
Ala Thr Gln Val Pro Leu Val Ser Ser Thr Ser Glu Gly Tyr Thr Ala
1               5                   10                  15
```

<210> SEQ ID NO 34
<211> LENGTH: 25
<212> TYPE: PRT
<213> ORGANISM: Homo sapiens

<400> SEQUENCE: 34

```
Gln Ile Leu Gly Val Ile Asp Lys Lys Leu Arg Asn Leu Glu Lys Lys
1               5                   10                  15

Lys Gly Lys Leu Asp Asp Tyr Gln Glu
            20                  25
```

<210> SEQ ID NO 35
<211> LENGTH: 23
<212> TYPE: PRT
<213> ORGANISM: Homo sapiens

<400> SEQUENCE: 35

```
Pro Arg Gly Arg Gly Gly Pro Pro Arg Pro Asn Arg Gly Met Pro Gln
1               5                   10                  15

Met Asn Thr Gln Gln Val Asn
            20
```

<210> SEQ ID NO 36
<211> LENGTH: 5
<212> TYPE: PRT
<213> ORGANISM: Gallus gallus

<400> SEQUENCE: 36

```
Ser Tyr Gln Met Asn
1               5
```

<210> SEQ ID NO 37
<211> LENGTH: 17
<212> TYPE: PRT
<213> ORGANISM: Gallus gallus

<400> SEQUENCE: 37

```
Ala Ile Asn Lys Phe Gly Asn Ser Thr Gly His Gly Ala Ala Val Lys
1               5                   10                  15

Gly
```

<210> SEQ ID NO 38
<211> LENGTH: 19
<212> TYPE: PRT
<213> ORGANISM: Gallus gallus

<400> SEQUENCE: 38

```
His Ala Tyr Gly Tyr Cys Gly Ser Gly Thr Trp Cys Ala Ala Gly Glu
1               5                   10                  15

Ile Asp Ala


<210> SEQ ID NO 39
<211> LENGTH: 128
<212> TYPE: PRT
<213> ORGANISM: Gallus gallus

<400> SEQUENCE: 39

Ala Val Thr Leu Asp Glu Ser Gly Gly Gly Leu Gln Met Ser Arg Gly
1               5                   10                  15

Gly Leu Ser Leu Val Cys Lys Ala Ser Gly Phe Asp Phe Ser Ser Tyr
            20                  25                  30

Gln Met Asn Trp Ile Arg Gln Ala Pro Gly Lys Gly Leu Glu Phe Val
        35                  40                  45

Ala Ala Ile Asn Lys Phe Gly Asn Ser Thr Gly His Gly Ala Ala Val
    50                  55                  60

Lys Gly Arg Val Thr Ile Ser Arg Asp Asn Gly Gln Ser Thr Val Arg
65                  70                  75                  80

Leu Gln Leu Asn Asn Leu Arg Ala Glu Asp Thr Ala Ile Tyr Phe Cys
            85                  90                  95

Thr Lys His Ala Tyr Gly Tyr Cys Gly Ser Gly Thr Trp Cys Ala Ala
            100                 105                 110

Gly Glu Ile Asp Ala Trp Gly His Gly Thr Glu Val Ile Val Ser Ser
        115                 120                 125


<210> SEQ ID NO 40
<211> LENGTH: 9
<212> TYPE: PRT
<213> ORGANISM: Gallus gallus

<400> SEQUENCE: 40

Ser Gly Gly Gly Ser Tyr Ser Tyr Gly
1               5


<210> SEQ ID NO 41
<211> LENGTH: 7
<212> TYPE: PRT
<213> ORGANISM: Gallus gallus

<400> SEQUENCE: 41

Asn Asn Lys Arg Pro Ser Asp
1               5


<210> SEQ ID NO 42
<211> LENGTH: 10
<212> TYPE: PRT
<213> ORGANISM: Gallus gallus

<400> SEQUENCE: 42

Ser Gly Asp Ser Thr Asp Thr Ala Val Phe
1               5                   10


<210> SEQ ID NO 43
<211> LENGTH: 108
<212> TYPE: PRT
<213> ORGANISM: Gallus gallus

<400> SEQUENCE: 43

Gln Ala Ala Ser Thr Gln Pro Ser Ser Val Ser Ala Asn Pro Gly Glu
```

-continued

```
1               5                   10                  15

Thr Val Glu Ile Thr Cys Ser Gly Gly Gly Ser Tyr Ser Tyr Gly Trp
            20                  25                  30

Phe Gln Gln Lys Ser Pro Gly Ser Ala Pro Val Thr Val Ile Tyr Tyr
        35                  40                  45

Asn Asn Lys Arg Pro Ser Asp Ile Pro Ser Arg Phe Ser Gly Ser Lys
    50                  55                  60

Ser Gly Ser Thr Gly Thr Leu Thr Ile Thr Gly Val Gln Ala Asp Asp
65                  70                  75                  80

Glu Ala Val Tyr Tyr Cys Gly Ser Gly Asp Ser Thr Asp Thr Ala Val
                85                  90                  95

Phe Gly Ala Gly Thr Thr Leu Thr Val Leu Gly Gln
            100                 105


<210> SEQ ID NO 44
<211> LENGTH: 5
<212> TYPE: PRT
<213> ORGANISM: Rabbit

<400> SEQUENCE: 44

Ser His Ser Leu Gly
1               5


<210> SEQ ID NO 45
<211> LENGTH: 16
<212> TYPE: PRT
<213> ORGANISM: Rabbit

<400> SEQUENCE: 45

Asp Ile Arg Ser Gly Gly Ser Ala Tyr Tyr Ala Asn Trp Ala Lys Gly
1               5                   10                  15


<210> SEQ ID NO 46
<211> LENGTH: 13
<212> TYPE: PRT
<213> ORGANISM: Rabbit

<400> SEQUENCE: 46

Thr Asn Gly Pro Ser Asp Leu Thr Asn Arg Leu Asp Leu
1               5                   10


<210> SEQ ID NO 47
<211> LENGTH: 121
<212> TYPE: PRT
<213> ORGANISM: Homo sapiens

<400> SEQUENCE: 47

Glu Gln Ser Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95
```

```
Arg Thr Asn Gly Pro Ser Asp Leu Thr Asn Arg Leu Asp Leu Trp Gly
            100                 105                 110

Gln Gly Thr Leu Val Thr Val Ser Ser
        115                 120


<210> SEQ ID NO 48
<211> LENGTH: 13
<212> TYPE: PRT
<213> ORGANISM: Rabbit

<400> SEQUENCE: 48

Gln Ala Ser Gln Ser Leu Tyr Asn Asn Glu Asn Leu Ala
1               5                   10


<210> SEQ ID NO 49
<211> LENGTH: 7
<212> TYPE: PRT
<213> ORGANISM: Rabbit

<400> SEQUENCE: 49

Gly Ala Ser Thr Leu Ala Ser
1               5


<210> SEQ ID NO 50
<211> LENGTH: 13
<212> TYPE: PRT
<213> ORGANISM: Rabbit

<400> SEQUENCE: 50

Leu Gly Glu Phe Ser Cys Gly Ser Ala Asp Cys Phe Ala
1               5                   10


<210> SEQ ID NO 51
<211> LENGTH: 112
<212> TYPE: PRT
<213> ORGANISM: Homo sapiens

<400> SEQUENCE: 51

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Leu Tyr Asn Asn Glu
            20                  25                  30

Asn Leu Ala Trp Phe Gln Gln Lys Pro Gly Lys Val Pro Lys Arg Leu
        35                  40                  45

Ile Tyr Gly Ala Ser Thr Leu Ala Ser Gly Val Ser Ser Arg Phe Ser
    50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95

Ser Ala Asp Cys Phe Ala Phe Gly Gly Gly Thr Lys Val Glu Ile Lys
            100                 105                 110


<210> SEQ ID NO 52
<211> LENGTH: 4
<212> TYPE: PRT
<213> ORGANISM: Gallus gallus

<400> SEQUENCE: 52

Phe Asp Met Gly
1
```

```
<210> SEQ ID NO 53
<211> LENGTH: 17
<212> TYPE: PRT
<213> ORGANISM: Gallus gallus

<400> SEQUENCE: 53

Gln Ile Asn Asp Ala Gly Ser Arg Thr Trp Tyr Ala Thr Ala Val Lys
1               5                   10                  15

Gly


<210> SEQ ID NO 54
<211> LENGTH: 12
<212> TYPE: PRT
<213> ORGANISM: Gallus gallus

<400> SEQUENCE: 54

Gly Ser Gly Tyr Val Gly Ala Gly Ala Ile Asp Ala
1               5                   10


<210> SEQ ID NO 55
<211> LENGTH: 120
<212> TYPE: PRT
<213> ORGANISM: Gallus gallus

<400> SEQUENCE: 55

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Phe
            20                  25                  30

Asp Met Gly Trp Val Arg Gln Ala Pro Gly Lys Gly Leu Glu Phe Val
        35                  40                  45

Ala Gln Ile Asn Asp Ala Gly Ser Arg Thr Trp Tyr Ala Thr Ala Val
    50                  55                  60

Lys Gly Arg Ala Thr Ile Ser Arg Asp Asn Gly Gln Thr Thr Val Arg
65                  70                  75                  80

Leu Gln Leu Asn Asn Leu Arg Ala Glu Asp Thr Gly Thr Tyr Tyr Cys
                85                  90                  95

Thr Arg Gly Ser Gly Tyr Val Gly Ala Gly Ala Ile Asp Ala Trp Gly
            100                 105                 110

His Gly Thr Glu Val Ile Val Ser
        115                 120


<210> SEQ ID NO 56
<211> LENGTH: 8
<212> TYPE: PRT
<213> ORGANISM: Gallus gallus

<400> SEQUENCE: 56

Ser Gly Gly Ser Gly Tyr Tyr Gly
1               5


<210> SEQ ID NO 57
<211> LENGTH: 7
<212> TYPE: PRT
<213> ORGANISM: Gallus gallus

<400> SEQUENCE: 57

Asn Asp Lys Arg Pro Ser Asp
1               5
```

<210> SEQ ID NO 58
<211> LENGTH: 10
<212> TYPE: PRT
<213> ORGANISM: Gallus gallus

<400> SEQUENCE: 58

```
Arg Tyr Asp Ser Thr Asp Ser Gly Ile Phe
1               5                   10
```

<210> SEQ ID NO 59
<211> LENGTH: 105
<212> TYPE: PRT
<213> ORGANISM: Gallus gallus

<400> SEQUENCE: 59

```
Ala Ala Leu Thr Gln Pro Ser Ser Val Ser Ala Asn Pro Gly Glu Thr
1               5                   10                  15

Val Lys Ile Thr Cys Ser Gly Gly Ser Gly Tyr Tyr Gly Trp Tyr Gln
            20                  25                  30

Gln Gln Lys Ser Pro Gly Ser Ala Pro Val Thr Val Ile Tyr Gln Asn
        35                  40                  45

Asp Lys Arg Pro Ser Asp Ile Pro Ser Arg Phe Ser Gly Ser Gly Ser
    50                  55                  60

Gly Ser Thr Asn Thr Leu Thr Ile Thr Gly Val Gln Ala Glu Asp Glu
65                  70                  75                  80

Ala Val Tyr Phe Cys Gly Arg Tyr Asp Ser Thr Asp Ser Gly Ile Phe
                85                  90                  95

Gly Ala Gly Thr Thr Leu Thr Val Leu
            100                 105
```

<210> SEQ ID NO 60
<211> LENGTH: 6
<212> TYPE: PRT
<213> ORGANISM: Oryctolagus cuniculus

<400> SEQUENCE: 60

```
Gly Ser Tyr Tyr Met Ser
1               5
```

<210> SEQ ID NO 61
<211> LENGTH: 17
<212> TYPE: PRT
<213> ORGANISM: Oryctolagus cuniculus

<400> SEQUENCE: 61

```
Tyr Ile Tyr Ile Gly Asp Gly Val Thr Ala Tyr Ala Asn Trp Ala Lys
1               5                   10                  15

Gly
```

<210> SEQ ID NO 62
<211> LENGTH: 4
<212> TYPE: PRT
<213> ORGANISM: Oryctolagus cuniculus

<400> SEQUENCE: 62

```
Gly Asn Lys Leu
1
```

<210> SEQ ID NO 63
<211> LENGTH: 112
<212> TYPE: PRT
<213> ORGANISM: Oryctolagus cuniculus

<400> SEQUENCE: 63

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Gly Ser Tyr
            20                  25                  30

Tyr Met Ser Trp Val Arg Gln Ala Pro Gly Lys Gly Leu Glu Trp Ile
        35                  40                  45

Ala Tyr Ile Tyr Ile Gly Asp Gly Val Thr Ala Tyr Ala Asn Trp Ala
    50                  55                  60

Lys Gly Arg Phe Thr Ile Ser Lys Ala Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Asn Lys Leu Trp Gly Pro Gly Thr Leu Val Thr Val Ser Ser
            100                 105                 110
```

<210> SEQ ID NO 64
<211> LENGTH: 11
<212> TYPE: PRT
<213> ORGANISM: Oryctolagus cuniculus

<400> SEQUENCE: 64

```
Gln Ala Ser Gln Ser Ile Ser Ser Tyr Leu Ala
1               5                   10
```

<210> SEQ ID NO 65
<211> LENGTH: 7
<212> TYPE: PRT
<213> ORGANISM: Oryctolagus cuniculus

<400> SEQUENCE: 65

```
Asp Ala Ser Asn Leu Asp Ser
1               5
```

<210> SEQ ID NO 66
<211> LENGTH: 14
<212> TYPE: PRT
<213> ORGANISM: Oryctolagus cuniculus

<400> SEQUENCE: 66

```
Gln Cys Thr Ala Val Ser Ser Ala Thr Ile Tyr Gly Asn Ala
1               5                   10
```

<210> SEQ ID NO 67
<211> LENGTH: 112
<212> TYPE: PRT
<213> ORGANISM: Oryctolagus cuniculus

<400> SEQUENCE: 67

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Arg Leu Ile
        35                  40                  45

Tyr Asp Ala Ser Asn Leu Asp Ser Gly Val Pro Ser Arg Phe Lys Gly
    50                  55                  60

Ser Gly Ser Gly Thr Asp Phe Thr Ile Thr Ile Ser Asp Leu Glu Cys
65                  70                  75                  80
```

```
Ala Asp Ala Ala Thr Tyr Tyr Cys Gln Cys Thr Ala Val Ser Ser Ala
                85                  90                  95

Thr Ile Tyr Gly Asn Ala Phe Gly Gly Gly Thr Glu Val Val Val Lys
            100                 105                 110


<210> SEQ ID NO 68
<211> LENGTH: 127
<212> TYPE: PRT
<213> ORGANISM: Gallus gallus

<400> SEQUENCE: 68

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Gly Tyr
            20                  25                  30

Asp Met Leu Trp Val Arg Gln Ala Pro Gly Lys Gly Leu Glu Trp Val
        35                  40                  45

Ala Gly Ile Gly Ser Thr Gly Gly Gly Thr Asp Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Val Ala Gly Gly Cys Asn Ser Gly Tyr Cys Arg Asp Ser Pro
            100                 105                 110

Gly Ser Ile Asp Ala Trp Gly His Gly Thr Glu Val Ile Val Ser
        115                 120                 125


<210> SEQ ID NO 69
<211> LENGTH: 107
<212> TYPE: PRT
<213> ORGANISM: Gallus gallus

<400> SEQUENCE: 69

Ala Val Thr Gln Gln Pro Ala Ser Val Ser Ala Asn Pro Gly Glu Thr
1               5                   10                  15

Val Lys Ile Thr Cys Ser Gly Gly Gly Ser Arg Asn Tyr Tyr Gly Trp
            20                  25                  30

Tyr Gln Gln Lys Ser Pro Gly Ser Val Pro Val Thr Val Ile Tyr Tyr
        35                  40                  45

Asp Asp Gln Arg Pro Ser Asn Ile Pro Ser Arg Phe Ser Gly Ala Leu
    50                  55                  60

Ser Gly Ser Thr Ser Thr Leu Thr Ile Thr Gly Val Gln Ala Asp Asp
65                  70                  75                  80

Glu Ala Val Tyr Phe Cys Gly Ser Ala Asp Ser Asn Thr Tyr Glu Gly
                85                  90                  95

Ser Phe Gly Ala Gly Thr Thr Leu Thr Val Leu
            100                 105


<210> SEQ ID NO 70
<211> LENGTH: 148
<212> TYPE: PRT
<213> ORGANISM: Mus musculus

<400> SEQUENCE: 70

Met Glu Trp Ser Gly Val Phe Ile Phe Leu Leu Ser Gly Thr Ala Gly
1               5                   10                  15
```

```
Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145


<210> SEQ ID NO 71
<211> LENGTH: 105
<212> TYPE: PRT
<213> ORGANISM: Mus musculus

<400> SEQUENCE: 71

Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Arg Ser Asn
            100                 105


<210> SEQ ID NO 72
<211> LENGTH: 109
<212> TYPE: PRT
<213> ORGANISM: Mus musculus

<400> SEQUENCE: 72

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80
```

```
Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105


<210> SEQ ID NO 73
<211> LENGTH: 94
<212> TYPE: PRT
<213> ORGANISM: Mus musculus

<400> SEQUENCE: 73

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90


<210> SEQ ID NO 74
<211> LENGTH: 118
<212> TYPE: PRT
<213> ORGANISM: Mus musculus

<400> SEQUENCE: 74

Ala Ala Glu Leu Val Arg Pro Gly Thr Ser Val Lys Val Ser Cys Lys
1               5                   10                  15

Ala Ser Gly Tyr Ala Phe Thr Asn Tyr Leu Ile Val Trp Ile Lys Gln
            20                  25                  30

Arg Pro Gly Gln Gly Leu Glu Trp Ile Gly Val Ile Ser Pro Gly Ser
        35                  40                  45

Gly Gly Thr Asn Tyr Asn Glu Lys Phe Lys Gly Lys Ala Ile Leu Thr
    50                  55                  60

Ala Asp Lys Ser Ser Ser Thr Ala Tyr Met Gln Leu Ser Ser Leu Thr
65                  70                  75                  80

Ser Asp Glu Phe Ala Val Tyr Phe Cys Ala Arg Glu Lys Ile Tyr Asp
                85                  90                  95

Asp Tyr Tyr Glu Gly Tyr Phe Asp Val Trp Gly Ala Gly Pro Arg His
            100                 105                 110

Leu Leu Ala Ser Leu Ser
        115


<210> SEQ ID NO 75
<211> LENGTH: 107
<212> TYPE: PRT
<213> ORGANISM: Mus musculus

<400> SEQUENCE: 75

Gly Thr Arg Cys Asp Ile Arg Leu Thr Gln Thr Thr Ser Ser Leu Ser
1               5                   10                  15

Ala Ser Leu Gly Asp Arg Val Thr Ile Ser Cys Ser Ala Ser Leu Gly
            20                  25                  30

Ile Gly Asn Tyr Leu Asn Trp Tyr Gln Gln Lys Pro Asp Gly Thr Val
```

```
        35                  40                  45

Lys Leu Leu Ile Tyr Tyr Thr Ser Asn Leu His Ser Gly Val Pro Ser
    50                  55                  60

Arg Phe Ser Gly Ser Gly Ser Gly Thr Asp Tyr Ser Leu Thr Ile Ser
65                  70                  75                  80

Asn Leu Glu Pro Glu Asp Ile Ala Thr Tyr Tyr Cys Gln His Tyr Ser
                85                  90                  95

Lys Leu Pro Leu Thr Phe Gly Ala Gly Pro Ser
            100                 105


<210> SEQ ID NO 76
<211> LENGTH: 113
<212> TYPE: PRT
<213> ORGANISM: Mus musculus

<400> SEQUENCE: 76

Gly Ala Glu Leu Val Arg Ser Gly Ala Ser Val Lys Met Ser Cys Lys
1               5                   10                  15

Ala Ser Gly Tyr Ser Phe Thr Asp Tyr Asn Met Tyr Trp Val Lys Gln
            20                  25                  30

Thr Pro Gly Gln Gly Leu Glu Trp Ile Gly Tyr Ile Tyr Pro Gly Asn
        35                  40                  45

Gly Gly Thr Asn Tyr Asn Gln Lys Phe Lys Gly Lys Ala Thr Leu Thr
    50                  55                  60

Ala Asp Thr Ser Ser Ser Thr Ala Tyr Met Gln Ile Ser Ser Leu Thr
65                  70                  75                  80

Ser Glu Asp Ser Ala Val Tyr Phe Cys Ala Arg Asp Tyr Asp Asp Gly
                85                  90                  95

Gly Tyr Ala Met Asp Tyr Trp Gly Gln Gly Thr Thr Val Thr Val Ser
            100                 105                 110

Ser


<210> SEQ ID NO 77
<211> LENGTH: 117
<212> TYPE: PRT
<213> ORGANISM: Mus musculus

<400> SEQUENCE: 77

Leu Leu Leu Trp Leu Thr Gly Ala Arg Cys Asp Ile Gln Met Thr Gln
1               5                   10                  15

Ser Pro Ala Ser Leu Ser Ala Ser Val Gly Glu Thr Val Thr Ile Thr
            20                  25                  30

Cys Arg Ala Ser Gly Asn Ile His Asn Tyr Leu Thr Trp Tyr Gln Gln
        35                  40                  45

Lys Gln Gly Lys Ser Pro Gln Leu Leu Val Tyr Asn Ala Lys Thr Leu
    50                  55                  60

Ala Asp Gly Val Pro Ser Arg Phe Ser Gly Ser Gly Ser Gly Thr Gln
65                  70                  75                  80

Tyr Ser Leu Lys Ile Asn Arg Leu Gln Pro Glu Asp Phe Gly Ser Tyr
                85                  90                  95

Tyr Cys Gln His Phe Trp Asn Ile Pro Trp Thr Phe Gly Gly Gly Thr
            100                 105                 110

Lys Leu Asn Ser Arg
        115


<210> SEQ ID NO 78
```

```
<211> LENGTH: 114
<212> TYPE: PRT
<213> ORGANISM: Mus musculus

<400> SEQUENCE: 78

Asp Ala Glu Leu Val Lys Pro Gly Ala Ser Val Lys Ile Ser Cys Lys
1               5                   10                  15

Ala Ser Gly Tyr Thr Phe Thr Asp His Ser Ile His Trp Val Gln Gln
            20                  25                  30

Lys Pro Glu Gln Gly Leu Glu Trp Ile Gly Tyr Ile Ser Pro Gly Asn
        35                  40                  45

Gly Asn Ile Lys Tyr Asn Glu Lys Phe Lys Gly Lys Ala Thr Leu Thr
    50                  55                  60

Ala Asp Lys Ser Ser Ser Thr Ala Tyr Met Gln Leu Asn Ser Leu Thr
65                  70                  75                  80

Ser Glu Asp Ser Ala Val Tyr Phe Cys Lys Arg Ser Leu Gly Arg Gly
                85                  90                  95

Gly Pro Tyr Tyr Phe Asp Tyr Trp Gly Gln Gly Thr Thr Val Thr Val
            100                 105                 110

Ser Ser


<210> SEQ ID NO 79
<211> LENGTH: 108
<212> TYPE: PRT
<213> ORGANISM: Mus musculus

<400> SEQUENCE: 79

Asp Ile Val Leu Thr Gln Ala Ala Pro Ser Leu Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Arg Glu Tyr Pro Val Thr Phe Gly Ser Gly Pro Asn
            100                 105


<210> SEQ ID NO 80
<211> LENGTH: 111
<212> TYPE: PRT
<213> ORGANISM: Mus musculus

<400> SEQUENCE: 80

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
```

```
65                  70                  75                  80

Met Gln Leu Ser Ser Leu Thr Ser Glu Asp Ser Ala Val Tyr Tyr Cys
                85                  90                  95

Ala Ser Tyr Tyr Trp Tyr Phe Asp Val Trp Ala Gln Asp His Val
            100                 105                 110


<210> SEQ ID NO 81
<211> LENGTH: 109
<212> TYPE: PRT
<213> ORGANISM: Mus musculus

<400> SEQUENCE: 81

Ile Val Met Thr Gln Ala Ala Phe Ser Asn Pro Val Thr Leu Gly Thr
1               5                   10                  15

Ser Ala Ser Ile Ser Cys Arg Ser Ser Lys Asn Leu Leu His Ser Asn
            20                  25                  30

Gly Ile Thr Tyr Leu Tyr Trp Tyr Leu Gln Arg Pro Gly Gln Ser Pro
        35                  40                  45

Gln Leu Leu Ile Tyr Arg Val Ser Asn Leu Ala Ser Gly Val Pro Asn
    50                  55                  60

Arg Phe Ser Gly Ser Glu Ser Gly Thr Asp Phe Thr Leu Arg Ile Ser
65                  70                  75                  80

Arg Val Glu Ala Glu Asp Val Gly Val Tyr Tyr Cys Ala Gln Leu Leu
                85                  90                  95

Glu Leu Pro Tyr Thr Ser Glu Gly Thr Lys Arg Trp Glu
            100                 105


<210> SEQ ID NO 82
<211> LENGTH: 109
<212> TYPE: PRT
<213> ORGANISM: Mus musculus

<400> SEQUENCE: 82

Gly Gly Gly Leu Val Lys Pro Gly Gly Ser Leu Lys Leu Ser Cys Ala
1               5                   10                  15

Ala Ser Gly Phe Ala Phe Ser Ser Tyr Asp Met Ser Trp Ile Arg Gln
            20                  25                  30

Thr Pro Glu Lys Arg Leu Glu Trp Val Ala Tyr Ile Ser Ser Gly Ala
        35                  40                  45

Gly Ser Thr Tyr Tyr Pro Asp Thr Val Lys Gly Arg Phe Thr Val Ser
    50                  55                  60

Arg Asp Asn Ala Lys Asn Thr Leu Tyr Leu Gln Met Ser Ser Leu Lys
65                  70                  75                  80

Ser Glu Asp Thr Ala Met Tyr Tyr Cys Ala Arg His Phe Tyr Arg Phe
                85                  90                  95

Asp Tyr Trp Gly Gln Gly Thr Thr Val Thr Val Ser Ser
            100                 105


<210> SEQ ID NO 83
<211> LENGTH: 113
<212> TYPE: PRT
<213> ORGANISM: Mus musculus

<400> SEQUENCE: 83

Leu Leu Leu Cys Val Ser Gly Ala Pro Gly Ser Ile Val Met Thr Gln
1               5                   10                  15

Thr Pro Lys Phe Leu Leu Val Ser Ala Gly Asp Arg Ile Thr Ile Thr
            20                  25                  30
```

```
Cys Lys Ala Ser Gln Ser Val Ser Asn Asp Val Ala Trp Tyr Gln Gln
        35                  40                  45

Lys Pro Gly Gln Ser Pro Lys Leu Leu Ile Tyr Tyr Ala Ser Asn Arg
    50                  55                  60

Tyr Thr Gly Val Pro Asp Arg Phe Thr Gly Ser Gly Tyr Gly Thr Asp
65                  70                  75                  80

Phe Thr Phe Thr Ile Ser Thr Val Gln Ala Glu Asp Leu Ala Val Tyr
                85                  90                  95

Phe Cys Gln Gln Asp Asp Arg Phe Pro Leu Thr Phe Gly Ala Gly Pro
            100                 105                 110

Ser


<210> SEQ ID NO 84
<211> LENGTH: 112
<212> TYPE: PRT
<213> ORGANISM: Mus musculus

<400> SEQUENCE: 84

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Thr Gly Ala Trp Phe Ala Tyr Trp Ala Lys Asp Ser Ser Arg His
            100                 105                 110


<210> SEQ ID NO 85
<211> LENGTH: 107
<212> TYPE: PRT
<213> ORGANISM: Mus musculus

<400> SEQUENCE: 85

Gly Val Glu Gly Asp Ile Val Met Thr Gln Ser His Lys Phe Met Ser
1               5                   10                  15

Thr Ser Val Gly Asp Arg Val Ser Ile Thr Cys Lys Ala Ser Gln Asp
            20                  25                  30

Val Gly Thr Ala Val Ala Trp Tyr Gln Gln Lys Pro Gly Gln Ser Pro
        35                  40                  45

Lys Leu Leu Ile Tyr Trp Ala Ser Thr Arg His Thr Gly Val Pro Asp
    50                  55                  60

Arg Phe Thr Gly Ser Gly Ser Gly Thr Asp Phe Thr Leu Thr Ile Ser
65                  70                  75                  80

Asn Val Gln Ser Glu Asp Leu Ala Asp Tyr Phe Cys Gln Gln Tyr Ser
                85                  90                  95

Ser Tyr Pro Leu Thr Phe Gly Ala Gly Pro Ser
            100                 105


<210> SEQ ID NO 86
<211> LENGTH: 118
```

```
<212> TYPE: PRT
<213> ORGANISM: Mus musculus

<400> SEQUENCE: 86

Gly Gly Gly Leu Val Gln Pro Gly Gly Ser Met Lys Val Ser Cys Val
1               5                   10                  15

Ala Ser Gly Phe Ser Phe Ile Asp Phe Trp Met Asn Trp Val Arg Gln
            20                  25                  30

Ser Pro Glu Lys Gly Leu Glu Trp Val Ala Glu Ile Arg Leu Lys Ser
        35                  40                  45

Asn Asn Tyr Ala Thr His Tyr Ala Glu Ser Val Lys Gly Arg Phe Thr
    50                  55                  60

Ile Ser Arg Asp Asp Ser Lys Ser Ser Val Tyr Leu Gln Met Asn Asn
65                  70                  75                  80

Leu Arg Pro Glu Asp Thr Gly Ile Tyr Tyr Cys Thr Ser Leu Phe Tyr
                85                  90                  95

Tyr Tyr Asp Gly Thr Ser Gly Phe Ala Tyr Trp Gly Gln Gly Thr Thr
            100                 105                 110

Val Thr Val Leu Leu Lys
        115


<210> SEQ ID NO 87
<211> LENGTH: 109
<212> TYPE: PRT
<213> ORGANISM: Mus musculus

<400> SEQUENCE: 87

Asp Ile Val Met Thr Gln Ser Pro Ser Ser Leu Thr Val Thr Ala Gly
1               5                   10                  15

Glu Lys Val Thr Met His Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Asp Tyr Pro Leu Thr Phe Gly Ala Gly Pro Ser
            100                 105


<210> SEQ ID NO 88
<211> LENGTH: 148
<212> TYPE: PRT
<213> ORGANISM: Mus musculus

<400> SEQUENCE: 88

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
```

```
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145
```

<210> SEQ ID NO 89
<211> LENGTH: 139
<212> TYPE: PRT
<213> ORGANISM: Mus musculus

<400> SEQUENCE: 89

```
Met Ser Val Leu Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Leu Thr Phe Gly Ala Gly Thr Lys Leu Glu Leu Lys Arg Ala
        115                 120                 125

Asp Ala Ala Pro Thr Val Ser Asn Pro Tyr Asp
    130                 135
```

<210> SEQ ID NO 90
<211> LENGTH: 100
<212> TYPE: PRT
<213> ORGANISM: Mus musculus

<400> SEQUENCE: 90

```
Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
```

100

<210> SEQ ID NO 91
<211> LENGTH: 90
<212> TYPE: PRT
<213> ORGANISM: Mus musculus

<400> SEQUENCE: 91

Asp Arg Val Ser Ile Thr Cys Lys Ala Ser Gln Asn Val Arg Thr Ala
1 5 10 15

Val Ala Trp Tyr Gln Gln Lys Pro Arg Gln Ser Pro Lys Ala Leu Ile
20 25 30

Tyr Leu Ala Ser Asn Arg Asp Thr Gly Leu Pro Asp Arg Phe Pro Gly
35 40 45

Arg Gly Ser Gly Thr Asp Phe Thr Leu Asn Ile Thr Asn Val Gln Ser
50 55 60

Glu Asp Leu Glu Asp Tyr Phe Cys Leu Gln His Cys Asn Tyr Pro Asn
65 70 75 80

Glu Phe Arg Gly Cys Thr Lys Val Pro Ile
85 90

<210> SEQ ID NO 92
<211> LENGTH: 116
<212> TYPE: PRT
<213> ORGANISM: Mus musculus

<400> SEQUENCE: 92

Leu Gln Glu Ser Gly Ala Glu Leu Ala Arg Pro Gly Ala Ser Val Lys
1 5 10 15

Leu Ser Cys Lys Ala Ser Gly Tyr Thr Phe Thr Ser Tyr Trp Met Gln
20 25 30

Trp Val Lys Gln Arg Pro Gly Gln Gly Leu Glu Trp Ile Gly Ala Ile
35 40 45

Tyr Pro Gly Asp Gly Asp Thr Arg Tyr Thr Gln Lys Phe Lys Gly Lys
50 55 60

Ala Thr Leu Thr Ala Asp Lys Ser Ser Ser Thr Ala Tyr Met Gln Leu
65 70 75 80

Ser Ser Leu Ala Ser Glu Asp Ser Ala Val Tyr Tyr Cys Ala Arg Gly
85 90 95

Glu Tyr Gly Asn Tyr Phe Ala Tyr Trp Gly Gln Gly Thr Thr Val Thr
100 105 110

Val Ser Ser Asn
115

<210> SEQ ID NO 93
<211> LENGTH: 100
<212> TYPE: PRT
<213> ORGANISM: Mus musculus

<400> SEQUENCE: 93

Thr Ser Asp Ala Ser Leu Gly Glu Arg Val Thr Ile Thr Cys Lys Ala
1 5 10 15

Ser Gln Asp Ile Asn Ser Tyr Leu Ser Trp Phe Gln Gln Lys Pro Gly
20 25 30

Lys Ser Pro Lys Thr Leu Ile Tyr Arg Ala Asn Arg Leu Val Asp Gly
35 40 45

Val Pro Ser Arg Phe Ser Gly Ser Gly Ser Gly Gln Asp Tyr Ser Leu
50 55 60

```
Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys
            100


<210> SEQ ID NO 94
<211> LENGTH: 108
<212> TYPE: PRT
<213> ORGANISM: Mus musculus

<400> SEQUENCE: 94

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
            20                  25                  30

Trp Ile Gly Arg Ile Asp Pro Ala Asn Gly Asn Thr Lys Tyr Asp Pro
        35                  40                  45

Lys Phe Gln Gly Lys Ala Thr Ile Thr Ala Asp Thr Ser Ser Asn Thr
    50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Tyr Gly Ser Ser Leu Ala Tyr
                85                  90                  95

Trp Gly Gln Gly Thr Thr Val Thr Val Ser Ser Lys
            100                 105


<210> SEQ ID NO 95
<211> LENGTH: 104
<212> TYPE: PRT
<213> ORGANISM: Mus musculus

<400> SEQUENCE: 95

Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
            20                  25                  30

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100


<210> SEQ ID NO 96
<211> LENGTH: 109
<212> TYPE: PRT
<213> ORGANISM: Mus musculus

<400> SEQUENCE: 96

Pro Arg Ala Ser Leu Gly Val Ser Glu Thr Leu Leu Cys Thr Ser Gly
1               5                   10                  15
```

```
Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105


<210> SEQ ID NO 97
<211> LENGTH: 94
<212> TYPE: PRT
<213> ORGANISM: Mus musculus

<400> SEQUENCE: 97

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90


<210> SEQ ID NO 98
<211> LENGTH: 111
<212> TYPE: PRT
<213> ORGANISM: Mus musculus

<400> SEQUENCE: 98

Pro Ala Cys Leu Pro Gly Gly Ser Leu Arg Leu Ser Cys Ala Thr Ser
1               5                   10                  15

Gly Phe Thr Phe Thr Asp Tyr Tyr Met Ser Trp Val Arg Gln Pro Pro
            20                  25                  30

Gly Lys Ala Leu Glu Trp Leu Gly Phe Ile Arg Asn Lys Ala Asn Gly
        35                  40                  45

Tyr Thr Thr Glu Tyr Ser Ala Ser Val Lys Gly Arg Phe Thr Ile Ser
    50                  55                  60

Arg Asp Asn Ser Gln Ser Ile Leu Tyr Leu Gln Met Asn Thr Leu Arg
65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
            100                 105                 110


<210> SEQ ID NO 99
<211> LENGTH: 102
<212> TYPE: PRT
<213> ORGANISM: Mus musculus
```

<400> SEQUENCE: 99

```
Arg Leu Pro Phe Tyr Ser Leu Glu Gln Arg Ala Thr Ile Ser Tyr Arg
1               5                   10                  15

Ala Ser Lys Asn Val Ser Thr Ser Gly Tyr Ser Tyr Met His Trp Asn
            20                  25                  30

Gln Gln Lys Pro Gly Gln Pro Pro Lys Leu Leu Ile Tyr Leu Val Ser
        35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Glu Asp Ala Ala
65                  70                  75                  80

Thr Tyr Tyr Cys Gln His Ile Arg Glu Leu Thr Arg Ser Glu Leu Val
                85                  90                  95

Pro Ser Trp Lys Ser Asn
            100
```

<210> SEQ ID NO 100
<211> LENGTH: 101
<212> TYPE: PRT
<213> ORGANISM: Mus musculus

<400> SEQUENCE: 100

```
Val Ser Cys Lys Ala Ser Gly Tyr Thr Phe Thr Ser Tyr Trp Met His
1               5                   10                  15

Trp Val Lys Gln Arg Pro Gly Gln Gly Leu Glu Trp Ile Gly Met Ile
            20                  25                  30

Asp Pro Ser Asn Ser Glu Thr Arg Leu Asn Gln Lys Phe Lys Asp Lys
        35                  40                  45

Ala Thr Leu Asn Val Asp Lys Ser Ser Asn Thr Ala Tyr Met Gln Leu
    50                  55                  60

Ser Ser Leu Thr Ser Glu Asp Ser Ala Val Tyr Tyr Cys Ala Arg Gly
65                  70                  75                  80

Leu Arg His Tyr Trp Tyr Phe Asp Val Trp Gly Gln Gly Thr Thr Val
                85                  90                  95

Thr Val Ser Ser Lys
            100
```

<210> SEQ ID NO 101
<211> LENGTH: 99
<212> TYPE: PRT
<213> ORGANISM: Mus musculus

<400> SEQUENCE: 101

```
Thr Ile Leu Trp Arg Glu Gly Pro Phe Ser Tyr Arg Ala Ser Lys Ser
1               5                   10                  15

Val Ser Thr Ser Gly Tyr Ser Tyr Met His Trp Asn Gln Gln Lys Pro
            20                  25                  30

Gly Gln Pro Pro Arg Leu Leu Ile Tyr Leu Val Ser Asn Leu Glu Ser
        35                  40                  45

Gly Val Pro Ala Arg Phe Ser Gly Ser Gly Ser Gly Thr Asp Phe Thr
    50                  55                  60

Leu Asn Ile His Pro Val Glu Glu Glu Asp Ala Ala Thr Tyr Tyr Cys
65                  70                  75                  80

Gln His Ile Arg Glu Leu Thr Arg Ser Glu Glu Val Pro Ser Trp Arg
                85                  90                  95

Ser Asn Lys
```

<210> SEQ ID NO 102
<211> LENGTH: 110
<212> TYPE: PRT
<213> ORGANISM: Mus musculus

<400> SEQUENCE: 102

```
Gly Gly Gly Leu Val Lys Pro Gly Gly Ser Leu Lys Leu Ser Cys Ala
1               5                   10                  15

Ala Ser Gly Phe Thr Phe Ser Ser Tyr Gly Met Ser Trp Val Arg Gln
            20                  25                  30

Thr Pro Glu Lys Arg Leu Glu Trp Val Ala Thr Ile Ser Ser Gly Gly
        35                  40                  45

Ser Tyr Thr Tyr Tyr Pro Asp Ser Val Lys Gly Arg Phe Thr Ile Ser
    50                  55                  60

Arg Asp Asn Ala Lys Asn Thr Leu Tyr Leu Gln Met Ser Ser Leu Arg
65                  70                  75                  80

Ser Glu Asp Thr Ala Met Tyr Tyr Cys Ala Ser Leu Ala Ser Tyr Tyr
                85                  90                  95

Phe Asp Tyr Trp Gly Gln Gly Thr Thr Leu Thr Val Ser Ser
            100                 105                 110
```

<210> SEQ ID NO 103
<211> LENGTH: 113
<212> TYPE: PRT
<213> ORGANISM: Mus musculus

<400> SEQUENCE: 103

```
Gly Ala Arg Cys Asp Val Gln Met Ile Gln Ser Pro Ser Ser Leu Ser
1               5                   10                  15

Ala Ser Leu Gly Asp Ile Val Thr Met Thr Cys Gln Ala Ser Gln Gly
            20                  25                  30

Thr Ser Ile Asn Leu Asn Trp Phe Gln Gln Lys Pro Gly Lys Ala Pro
        35                  40                  45

Lys Leu Leu Ile Tyr Gly Ala Ser Ser Leu Glu Asp Gly Val Pro Ser
    50                  55                  60

Arg Phe Ser Gly Ser Cys Phe Gly Thr Asp Phe Thr Leu Thr Ile Ser
65                  70                  75                  80

Ser Leu Glu Asp Glu Asp Met Ala Thr Tyr Phe Cys Leu Gln His Ser
                85                  90                  95

Tyr Leu Pro Pro Leu Thr Phe Gly Ala Gly Thr Lys Leu Glu Leu Lys
            100                 105                 110

Arg
```

<210> SEQ ID NO 104
<211> LENGTH: 111
<212> TYPE: PRT
<213> ORGANISM: Mus musculus

<400> SEQUENCE: 104

```
Gly Pro Gly Leu Val Gln Pro Ser Gln Ser Leu Ser Ile Thr Cys Thr
1               5                   10                  15

Val Ser Gly Phe Ser Leu Thr Thr Tyr Asp Leu His Trp Val Arg Gln
            20                  25                  30

Ser Pro Gly Lys Gly Leu Glu Trp Leu Gly Val Ile Trp Ser Gly Gly
        35                  40                  45

Ser Thr Asp Tyr Asn Ala Ala Phe Ile Ser Arg Leu Ser Ile Ser Lys
```

```
    50                  55                  60

Asp Asn Ser Lys Ser Gln Val Phe Phe Lys Met Asn Ser Leu Gln Ala
65                  70                  75                  80

Asn Asp Thr Ala Ile Tyr Tyr Cys Ala Arg Asn Tyr Gly Tyr Ser Ala
                85                  90                  95

Trp Phe Ala Tyr Trp Gly Gln Gly Thr Leu Val Thr Val Ser Ala
            100                 105                 110


<210> SEQ ID NO 105
<211> LENGTH: 118
<212> TYPE: PRT
<213> ORGANISM: Mus musculus

<400> SEQUENCE: 105

Pro Ala Ser Ser Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Leu Thr Phe Gly Ala Gly Thr
            100                 105                 110

Lys Leu Glu Leu Lys Arg
        115


<210> SEQ ID NO 106
<211> LENGTH: 114
<212> TYPE: PRT
<213> ORGANISM: Mus musculus

<400> SEQUENCE: 106

Gly Phe Glu Leu Lys Lys Pro Gly Glu Thr Val Lys Ile Ser Cys Lys
1               5                   10                  15

Ala Ser Gly Tyr Thr Phe Thr Ala Tyr Ser Met His Trp Val Lys Gln
            20                  25                  30

Thr Pro Gly Lys Gly Leu Lys Trp Leu Gly Trp Ile Asn Thr Glu Thr
        35                  40                  45

Gly Glu Pro Thr Tyr Thr Asp Asp Phe Lys Gly Arg Phe Thr Phe Ser
    50                  55                  60

Leu Glu Thr Ser Ala Arg Ile Ala Tyr Leu Gln Ile Asn Asp Leu Lys
65                  70                  75                  80

Asn Glu Asp Thr Ala Thr Tyr Phe Cys Ala Arg Arg Ile Tyr Tyr Phe
                85                  90                  95

Gly Arg Gly Gly Phe Asp Tyr Trp Gly Gln Gly Thr Thr Val Thr Val
            100                 105                 110

Ser Ser


<210> SEQ ID NO 107
<211> LENGTH: 118
<212> TYPE: PRT
<213> ORGANISM: Mus musculus
```

<400> SEQUENCE: 107

```
Pro Ala Ser Ser Ser Asp Val Leu Met Thr Gln Thr Pro Leu Ser Leu
1               5                   10                  15

Pro Val Arg Leu Gly Asp Gln Ser Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Pro Glu Asp Leu Gly Val Tyr
                85                  90                  95

Tyr Cys Phe Gln Gly Ser His Val Pro Tyr Thr Ser Glu Gly Asp Gln
            100                 105                 110

Ala Glu Ile Lys Leu Ala
        115
```

<210> SEQ ID NO 108
<211> LENGTH: 114
<212> TYPE: PRT
<213> ORGANISM: Mus musculus

<400> SEQUENCE: 108

```
Gly Gly Gly Leu Val Gln Pro Gly Gly Ser Met Arg Leu Ser Cys Val
1               5                   10                  15

Ala Ser Gly Phe Thr Phe Ser Asn Ser Trp Phe Asn Trp Val Arg Gln
            20                  25                  30

Ser Pro Glu Lys Gly Leu Glu Trp Val Ala Glu Ile Arg Leu Thr Ser
        35                  40                  45

Asp Asn Tyr Ala Ile Tyr Tyr Ala Glu Ser Val Lys Gly Arg Phe Thr
    50                  55                  60

Ile Ser Arg Asp Asp Ser Lys Ser Ser Val Tyr Leu Gln Met Asn Asn
65                  70                  75                  80

Leu Arg Ala Glu Asp Thr Gly Ile Tyr Tyr Cys Thr Arg Pro Glu Thr
                85                  90                  95

Ala Arg Ala Thr Phe Ala Tyr Trp Gly Gln Gly Thr Thr Val Thr Val
            100                 105                 110

Ser Ser
```

<210> SEQ ID NO 109
<211> LENGTH: 118
<212> TYPE: PRT
<213> ORGANISM: Mus musculus

<400> SEQUENCE: 109

```
Pro Ala Ser Thr Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Val Leu Ile Tyr Lys Val Phe Asn Arg
    50                  55                  60

Phe Ser Gly Val Pro Asp Arg Phe Ser Gly Ser Gly Ser Gly Thr Asp
```

```
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Arg Thr Phe Gly Gly Gly Thr
            100                 105                 110

Lys Leu Asn Gln Thr Gly
        115


<210> SEQ ID NO 110
<211> LENGTH: 111
<212> TYPE: PRT
<213> ORGANISM: Mus musculus

<400> SEQUENCE: 110

Gly Pro Asp Leu Val Lys Pro Gly Ala Ser Val Lys Ile Ser Cys Lys
1               5                   10                  15

Ala Ser Gly Tyr Ser Phe Thr Ala Tyr Tyr Met His Trp Val Lys Gln
            20                  25                  30

Ser His Gly Lys Ser Leu Glu Trp Ile Gly Arg Val Asn Pro Asn Asn
        35                  40                  45

Gly Gly Thr Thr Tyr Asn Gln Lys Phe Lys Gly Lys Ala Ile Leu Thr
    50                  55                  60

Val Asp Lys Ser Ser Ser Thr Ala Tyr Met Glu Leu Arg Ser Leu Thr
65                  70                  75                  80

Phe Glu Asp Ser Ala Val Tyr Tyr Cys Ala Arg Arg Ile Tyr Tyr Gly
                85                  90                  95

Tyr Phe Asp Tyr Trp Gly Gln Gly Thr Thr Val Thr Val Ser Ser
            100                 105                 110


<210> SEQ ID NO 111
<211> LENGTH: 104
<212> TYPE: PRT
<213> ORGANISM: Mus musculus

<400> SEQUENCE: 111

Ala Phe Phe Ala Val Ser Leu Gly Gln Arg Ala Thr Ile Ser Cys Lys
1               5                   10                  15

Ala Ser Gln Ser Val Asp Tyr Asp Gly Asp Ser Tyr Met Asn Trp Tyr
            20                  25                  30

Gln Gln Lys Pro Gly Gln Pro Pro Lys Leu Leu Ile Tyr Val Ala Ser
        35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Glu Asp Ala Ala
65                  70                  75                  80

Thr Tyr Tyr Cys Gln Gln Ser Asn Glu Asp Pro Tyr Thr Phe Gly Gly
                85                  90                  95

Gly Thr Lys Leu Glu Ile Lys Gln
            100


<210> SEQ ID NO 112
<211> LENGTH: 106
<212> TYPE: PRT
<213> ORGANISM: Mus musculus

<400> SEQUENCE: 112

Gly Ala Glu Leu Val Lys Pro Gly Ala Ser Val Lys Leu Ser Cys Thr
1               5                   10                  15
```

```
Ala Ser Gly Leu Asn Ile Arg Asp Ile Tyr Met His Trp Val Lys Gln
            20                  25                  30

Arg Pro Glu Gln Gly Leu Glu Trp Ile Gly Lys Ile Asp Pro Ala Asn
        35                  40                  45

Gly Asn Thr Lys Tyr Asp Pro Lys Phe Gln Gly Lys Ala Thr Ile Thr
    50                  55                  60

Ala Asp Thr Ser Ser Asn Thr Ala Tyr Val Gln Leu Ser Ser Leu Thr
65                  70                  75                  80

Ser Glu Asp Thr Ala Val Tyr Tyr Cys Ala Gly Thr Gly Asp Tyr Trp
                85                  90                  95

Gly Gln Gly Thr Thr Val Thr Val Ser Ser
            100                 105


<210> SEQ ID NO 113
<211> LENGTH: 112
<212> TYPE: PRT
<213> ORGANISM: Mus musculus

<400> SEQUENCE: 113

Gly Thr Cys Gly Asp Ile Val Met Ser Gln Ser Pro Ser Ser Leu Ala
1               5                   10                  15

Val Ser Ala Gly Glu Lys Val Thr Met Ser Cys Lys Ser Ser Gln Ser
            20                  25                  30

Leu Leu Asn Ser Arg Thr Arg Lys Asn Tyr Leu Ala Trp Val Gln His
        35                  40                  45

Lys Pro Gly Gln Ser Pro Arg Leu Leu Ile Tyr Trp Ala Ser Thr Arg
    50                  55                  60

Glu Ser Gly Val Pro Asp Arg Phe Thr Gly Ser Gly Ser Gly Thr Asp
65                  70                  75                  80

Phe Thr Leu Thr Ile Ser Ser Val Gln Ala Glu Asp Leu Ala Val Tyr
                85                  90                  95

Tyr Cys Arg Gln Ser Tyr Asn Leu Val Thr Phe Gly Ala Gly Pro Ser
            100                 105                 110


<210> SEQ ID NO 114
<211> LENGTH: 112
<212> TYPE: PRT
<213> ORGANISM: Mus musculus

<400> SEQUENCE: 114

Gly Pro Glu Leu Val Lys Pro Gly Ala Ser Val Lys Met Ser Cys Lys
1               5                   10                  15

Ala Ser Gly Tyr Thr Phe Thr Ser Tyr Val Met His Trp Val Lys Gln
            20                  25                  30

Lys Pro Gly Gln Gly Leu Glu Trp Ile Gly Tyr Ile Asn Pro Tyr Asn
        35                  40                  45

Asp Gly Thr Lys Tyr Asn Glu Lys Phe Lys Gly Lys Ala Thr Leu Thr
    50                  55                  60

Ser Asp Lys Ser Ser Ser Thr Ala Tyr Met Glu Leu Ser Ser Leu Thr
65                  70                  75                  80

Ser Glu Asp Ser Ala Val Tyr Tyr Cys Ala Arg Arg Tyr Tyr Tyr Gly
                85                  90                  95

Ser Ser Gly Gly Tyr Phe Asp Val Trp Ala Gln Asp His Val Arg Thr
            100                 105                 110


<210> SEQ ID NO 115
```

<211> LENGTH: 108
<212> TYPE: PRT
<213> ORGANISM: Mus musculus

<400> SEQUENCE: 115

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys Arg
            100                 105
```

<210> SEQ ID NO 116
<211> LENGTH: 113
<212> TYPE: PRT
<213> ORGANISM: Mus musculus

<400> SEQUENCE: 116

```
Gly Pro Glu Leu Val Lys Pro Gly Ala Ser Val Lys Ile Ser Cys Lys
1               5                   10                  15

Ala Ser Gly Tyr Ser Phe Thr Gly Tyr Phe Met Asn Trp Val Met Gln
            20                  25                  30

Ser His Gly Lys Ser Leu Glu Trp Ile Gly Arg Ile Asn Pro Tyr Asn
        35                  40                  45

Gly Asp Thr Phe Tyr Asn Gln Lys Phe Lys Gly Lys Ala Thr Leu Thr
    50                  55                  60

Val Asp Lys Ser Ser Ser Thr Ala His Met Glu Leu Arg Ser Leu Ala
65                  70                  75                  80

Ser Glu Asp Ser Ala Val Tyr Tyr Cys Ala Arg Arg Ile His Tyr Tyr
                85                  90                  95

Tyr Gly Ser Ser Tyr Tyr Ala Met Asp Tyr Trp Gly Gln Glu Pro His
            100                 105                 110

His
```

<210> SEQ ID NO 117
<211> LENGTH: 108
<212> TYPE: PRT
<213> ORGANISM: Mus musculus

<400> SEQUENCE: 117

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
```

```
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys Arg
            100                 105


<210> SEQ ID NO 118
<211> LENGTH: 113
<212> TYPE: PRT
<213> ORGANISM: Mus musculus

<400> SEQUENCE: 118

Gly Ala Gly Leu Val Lys Pro Gly Ala Ser Val Lys Leu Ser Cys Lys
1               5                   10                  15

Ala Ser Gly Tyr Thr Phe Thr Glu Tyr Ile Ile His Trp Val Lys Gln
            20                  25                  30

Arg Ser Gly Gln Gly Leu Glu Trp Ile Gly Trp Phe Tyr Pro Gly Ser
        35                  40                  45

Gly Ser Ile Lys Tyr Asn Glu Lys Phe Lys Asp Lys Ala Thr Leu Thr
    50                  55                  60

Ala Asp Lys Ser Ser Ser Thr Val Tyr Met Glu Leu Ser Arg Leu Thr
65                  70                  75                  80

Ser Glu Asp Ser Ala Val Tyr Phe Cys Ala Arg His Glu Val Tyr Tyr
                85                  90                  95

Asp Tyr Asp Lys Ser Met Leu Trp Thr Thr Gly Val Lys Asn Leu Ile
            100                 105                 110

Arg


<210> SEQ ID NO 119
<211> LENGTH: 108
<212> TYPE: PRT
<213> ORGANISM: Mus musculus

<400> SEQUENCE: 119

Ser Pro Ser Ser Leu Ala Val Ser Val Gly Glu Lys Val Thr Met Ser
1               5                   10                  15

Cys Lys Ser Ser Gln Ser Leu Leu Tyr Ser Ser Asn Gln Lys Asn Tyr
            20                  25                  30

Leu Ala Trp Tyr Gln Gln Lys Pro Gly Gln Ser Pro Lys Leu Leu Ile
        35                  40                  45

Tyr Trp Ala Ser Thr Arg Glu Ser Gly Val Pro Asp Arg Phe Thr Gly
    50                  55                  60

Ser Gly Ser Gly Thr Asp Phe Thr Leu Thr Ile Ser Ser Val Lys Ala
65                  70                  75                  80

Glu Asp Leu Ala Val Tyr Tyr Cys Gln Gln Tyr Tyr Ser Tyr Pro Tyr
                85                  90                  95

Thr Phe Gly Gly Gly Thr Lys Leu Glu Ile Lys Arg
            100                 105


<210> SEQ ID NO 120
<211> LENGTH: 113
<212> TYPE: PRT
<213> ORGANISM: Mus musculus

<400> SEQUENCE: 120

Gly Ala Glu Leu Val Arg Pro Gly Thr Ser Val Lys Val Ser Cys Lys
1               5                   10                  15
```

```
Ala Ser Val Tyr Ala Phe Thr Asn Tyr Leu Ile Glu Trp Val Lys Gln
            20                  25                  30

Arg Pro Gly Gln Gly Leu Glu Trp Ile Gly Val Ile Asn Pro Lys Ser
        35                  40                  45

Gly Gly Thr Lys Tyr Asn Glu Lys Phe Arg Gly Lys Ala Thr Leu Thr
    50                  55                  60

Ala Asp Lys Ser Ser Ser Thr Ala Tyr Met Gln Leu Ser Ser Leu Thr
65                  70                  75                  80

Ser Gly Asp Ser Ala Val Tyr Phe Cys Ala Ile Thr Gly Thr Asp Tyr
                85                  90                  95

Trp Gly Gln Gly Thr Thr Leu Thr Val Ser Ser Ala Lys Thr Thr Pro
            100                 105                 110

Pro
```

<210> SEQ ID NO 121
<211> LENGTH: 113
<212> TYPE: PRT
<213> ORGANISM: Mus musculus

<400> SEQUENCE: 121

```
Gln Gly Thr Arg Cys Asp Ile Gln Met Thr Gln Thr Thr Ser Ser Leu
1               5                   10                  15

Ser Ala Ser Leu Gly Asp Arg Val Thr Ile Ser Cys Ser Ala Ser Gln
            20                  25                  30

Gly Ile Asn Asn Tyr Leu Asn Trp Tyr Gln Gln Lys Pro Asp Gly Thr
        35                  40                  45

Val Lys Leu Leu Ile Tyr Tyr Thr Ser Ser Leu Arg Ser Gly Val Pro
    50                  55                  60

Ser Arg Phe Ser Gly Ser Gly Ser Gly Thr Asp Tyr Ser Leu Thr Ile
65                  70                  75                  80

Ser Asn Leu Glu Pro Glu Asp Val Ala Thr Tyr Tyr Cys Gln Gln Tyr
                85                  90                  95

Ser Lys Leu Pro Arg Thr Phe Gly Gly Gly Thr Lys Leu Glu Ile Lys
            100                 105                 110

Arg
```

<210> SEQ ID NO 122
<211> LENGTH: 121
<212> TYPE: PRT
<213> ORGANISM: Homo sapiens

<400> SEQUENCE: 122

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110
```

```
Gln Gly Thr Leu Val Thr Val Ser Ser
        115                 120


<210> SEQ ID NO 123
<211> LENGTH: 112
<212> TYPE: PRT
<213> ORGANISM: Homo sapiens

<400> SEQUENCE: 123

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Leu Tyr Asn Asn Glu
            20                  25                  30

Asn Leu Ala Trp Phe Gln Gln Lys Pro Gly Lys Val Pro Lys Arg Leu
        35                  40                  45

Ile Tyr Gly Ala Ser Thr Leu Ala Ser Gly Val Ser Ser Arg Phe Ser
    50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95

Ser Ala Asp Cys Phe Ala Phe Gly Gly Gly Thr Lys Val Glu Ile Lys
            100                 105                 110


<210> SEQ ID NO 124
<211> LENGTH: 121
<212> TYPE: PRT
<213> ORGANISM: Homo sapiens

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120


<210> SEQ ID NO 125
<211> LENGTH: 112
<212> TYPE: PRT
<213> ORGANISM: Homo sapiens

<400> SEQUENCE: 125

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Leu Tyr Asn Asn Glu
            20                  25                  30
```

```
Asn Leu Ala Trp Phe Gln Gln Lys Pro Gly Lys Val Pro Lys Arg Leu
        35                  40                  45

Ile Tyr Gly Ala Ser Thr Leu Ala Ser Gly Val Ser Ser Arg Phe Ser
    50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95

Ser Ala Asp Cys Phe Ala Phe Gly Gly Gly Thr Lys Val Glu Ile Lys
            100                 105                 110
```

<210> SEQ ID NO 126
<211> LENGTH: 121
<212> TYPE: PRT
<213> ORGANISM: Homo sapiens

<400> SEQUENCE: 126

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120
```

<210> SEQ ID NO 127
<211> LENGTH: 113
<212> TYPE: PRT
<213> ORGANISM: Homo sapiens

<400> SEQUENCE: 127

```
Glu Gln Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys
```

<210> SEQ ID NO 128
<211> LENGTH: 121
<212> TYPE: PRT
<213> ORGANISM: Homo sapiens

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120
```

<210> SEQ ID NO 129
<211> LENGTH: 113
<212> TYPE: PRT
<213> ORGANISM: Homo sapiens

<400> SEQUENCE: 129

```
Glu Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Thr Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys
```

<210> SEQ ID NO 130
<211> LENGTH: 121
<212> TYPE: PRT
<213> ORGANISM: Homo sapiens

<400> SEQUENCE: 130

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45
```

```
Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120


<210> SEQ ID NO 131
<211> LENGTH: 113
<212> TYPE: PRT
<213> ORGANISM: Homo sapiens

<400> SEQUENCE: 131

Glu Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Thr Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys


<210> SEQ ID NO 132
<211> LENGTH: 121
<212> TYPE: PRT
<213> ORGANISM: Homo sapiens

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120
```

<210> SEQ ID NO 133
<211> LENGTH: 113
<212> TYPE: PRT
<213> ORGANISM: Homo sapiens

<400> SEQUENCE: 133

```
Glu Gln Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys
```

<210> SEQ ID NO 134
<211> LENGTH: 5
<212> TYPE: PRT
<213> ORGANISM: Gallus gallus

<400> SEQUENCE: 134

```
Gly Tyr Asp Met Leu
1               5
```

<210> SEQ ID NO 135
<211> LENGTH: 17
<212> TYPE: PRT
<213> ORGANISM: Gallus gallus

<400> SEQUENCE: 135

```
Gly Ile Gly Ser Thr Gly Gly Gly Thr Asp Tyr Gly Ala Ala Val Lys
1               5                   10                  15

Gly
```

<210> SEQ ID NO 136
<211> LENGTH: 19
<212> TYPE: PRT
<213> ORGANISM: Gallus gallus

<400> SEQUENCE: 136

```
Val Ala Gly Gly Cys Asn Ser Gly Tyr Cys Arg Asp Ser Pro Gly Ser
1               5                   10                  15

Ile Asp Ala
```

<210> SEQ ID NO 137
<211> LENGTH: 10
<212> TYPE: PRT
<213> ORGANISM: Gallus gallus

<400> SEQUENCE: 137

```
Ser Gly Gly Gly Ser Arg Asn Tyr Tyr Gly
1               5                   10
```

<210> SEQ ID NO 138
<211> LENGTH: 7
<212> TYPE: PRT
<213> ORGANISM: Gallus gallus

<400> SEQUENCE: 138

Asp Asp Gln Arg Pro Ser Asn
1               5

<210> SEQ ID NO 139
<211> LENGTH: 11
<212> TYPE: PRT
<213> ORGANISM: Gallus gallus

<400> SEQUENCE: 139

Ser Ala Asp Ser Asn Thr Tyr Glu Gly Ser Phe
1               5                   10

<210> SEQ ID NO 140
<211> LENGTH: 5
<212> TYPE: PRT
<213> ORGANISM: Mus musculus

<400> SEQUENCE: 140

Asp Tyr Asn Met Asp
1               5

<210> SEQ ID NO 141
<211> LENGTH: 17
<212> TYPE: PRT
<213> ORGANISM: Mus musculus

<400> SEQUENCE: 141

Asp Ile Asn Pro Asn Tyr Asp Ser Thr Ser Tyr Asn Gln Lys Phe Lys
1               5                   10                  15

Gly

<210> SEQ ID NO 142
<211> LENGTH: 11
<212> TYPE: PRT
<213> ORGANISM: Mus musculus

<400> SEQUENCE: 142

Ser Arg Ser Tyr Asp Tyr Glu Gly Phe Ala Tyr
1               5                   10

<210> SEQ ID NO 143
<211> LENGTH: 11
<212> TYPE: PRT
<213> ORGANISM: Mus musculus

<400> SEQUENCE: 143

Leu Ser Ile Val Asn Arg Tyr His Tyr Met Ser
1               5                   10

<210> SEQ ID NO 144
<211> LENGTH: 6
<212> TYPE: PRT
<213> ORGANISM: Mus musculus

<400> SEQUENCE: 144

Glu Ala Ser Ile Thr Lys
1               5

<210> SEQ ID NO 145
<211> LENGTH: 9
<212> TYPE: PRT
<213> ORGANISM: Mus musculus

<400> SEQUENCE: 145

Gln His Asn Arg Gly Ser Phe Leu Pro
1               5

<210> SEQ ID NO 146
<211> LENGTH: 5
<212> TYPE: PRT
<213> ORGANISM: Mus musculus

<400> SEQUENCE: 146

Asp Tyr Tyr Met Ser
1               5

<210> SEQ ID NO 147
<211> LENGTH: 17
<212> TYPE: PRT
<213> ORGANISM: Mus musculus

<400> SEQUENCE: 147

Arg Asn Lys Ala Asn Gly Tyr Thr Thr Glu Tyr Ser Ala Ser Val Lys
1               5                   10                  15

Gly

<210> SEQ ID NO 148
<211> LENGTH: 9
<212> TYPE: PRT
<213> ORGANISM: Mus musculus

<400> SEQUENCE: 148

Ala Arg Ala Asn Trp Ala Phe Asp Tyr
1               5

<210> SEQ ID NO 149
<211> LENGTH: 11
<212> TYPE: PRT
<213> ORGANISM: Mus musculus

<400> SEQUENCE: 149

Arg Ala Ser Gln Ser Ile Ser Asn Tyr Leu His
1               5                   10

<210> SEQ ID NO 150
<211> LENGTH: 7
<212> TYPE: PRT
<213> ORGANISM: Mus musculus

<400> SEQUENCE: 150

Tyr Ala Ser Gln Ser Ile Ser
1               5

<210> SEQ ID NO 151
<211> LENGTH: 7
<212> TYPE: PRT
<213> ORGANISM: Mus musculus

<400> SEQUENCE: 151

Tyr Ala Ser Gln Ser Ile Ser
1               5

<210> SEQ ID NO 152
<211> LENGTH: 5
<212> TYPE: PRT
<213> ORGANISM: Mus musculus

<400> SEQUENCE: 152

Asn Tyr Leu Ile Val
1               5

<210> SEQ ID NO 153
<211> LENGTH: 17
<212> TYPE: PRT
<213> ORGANISM: Mus musculus

<400> SEQUENCE: 153

Val Ile Ser Pro Gly Ser Gly Gly Thr Asn Tyr Asn Glu Lys Phe Lys
1               5                   10                  15

Gly

<210> SEQ ID NO 154
<211> LENGTH: 11
<212> TYPE: PRT
<213> ORGANISM: Mus musculus

<400> SEQUENCE: 154

Glu Lys Ile Tyr Asp Asp Tyr Tyr Glu Gly Tyr
1               5                   10

<210> SEQ ID NO 155
<211> LENGTH: 15
<212> TYPE: PRT
<213> ORGANISM: Mus musculus

<400> SEQUENCE: 155

Thr Ile Ser Cys Ser Ala Ser Leu Gly Ile Gly Asn Tyr Leu Asn
1               5                   10                  15

<210> SEQ ID NO 156
<211> LENGTH: 7
<212> TYPE: PRT
<213> ORGANISM: Mus musculus

<400> SEQUENCE: 156

Thr Ser Asn Leu His Ser Gly
1               5

<210> SEQ ID NO 157
<211> LENGTH: 9
<212> TYPE: PRT
<213> ORGANISM: Mus musculus

<400> SEQUENCE: 157

His Tyr Ser Lys Leu Pro Leu Thr Phe
1               5

<210> SEQ ID NO 158
<211> LENGTH: 5
<212> TYPE: PRT
<213> ORGANISM: Mus musculus

<400> SEQUENCE: 158

Asp Tyr Asn Met Tyr
1               5

<210> SEQ ID NO 159
<211> LENGTH: 17
<212> TYPE: PRT
<213> ORGANISM: Mus musculus

<400> SEQUENCE: 159

```
Tyr Ile Tyr Pro Gly Asn Gly Gly Thr Asn Tyr Asn Gln Lys Phe Lys
1               5                   10                  15

Gly
```

<210> SEQ ID NO 160
<211> LENGTH: 11
<212> TYPE: PRT
<213> ORGANISM: Mus musculus

<400> SEQUENCE: 160

```
Asp Tyr Asp Asp Gly Gly Tyr Ala Met Asp Tyr
1               5                   10
```

<210> SEQ ID NO 161
<211> LENGTH: 15
<212> TYPE: PRT
<213> ORGANISM: Mus musculus

<400> SEQUENCE: 161

```
Ser Val Gly Glu Thr Val Thr Ile Thr Cys Arg Ala Ser Gly Asn
1               5                   10                  15
```

<210> SEQ ID NO 162
<211> LENGTH: 7
<212> TYPE: PRT
<213> ORGANISM: Mus musculus

<400> SEQUENCE: 162

```
Asn Ala Lys Thr Leu Ala Asp
1               5
```

<210> SEQ ID NO 163
<211> LENGTH: 9
<212> TYPE: PRT
<213> ORGANISM: Mus musculus

<400> SEQUENCE: 163

```
Gln His Phe Trp Asn Ile Pro Trp Thr
1               5
```

<210> SEQ ID NO 164
<211> LENGTH: 5
<212> TYPE: PRT
<213> ORGANISM: Mus musculus

<400> SEQUENCE: 164

```
Asp His Ser Ile His
1               5
```

<210> SEQ ID NO 165
<211> LENGTH: 17
<212> TYPE: PRT
<213> ORGANISM: Mus musculus

<400> SEQUENCE: 165

```
Tyr Ile Ser Pro Gly Asn Gly Asn Ile Lys Tyr Asn Glu Lys Phe Lys
1               5                   10                  15

Gly
```

<210> SEQ ID NO 166
<211> LENGTH: 12
<212> TYPE: PRT
<213> ORGANISM: Mus musculus

<400> SEQUENCE: 166

```
Ser Leu Gly Arg Gly Gly Pro Tyr Tyr Phe Asp Tyr
1               5                   10
```

<210> SEQ ID NO 167
<211> LENGTH: 16
<212> TYPE: PRT
<213> ORGANISM: Mus musculus

<400> SEQUENCE: 167

```
Arg Ser Ser Lys Ser Leu Leu His Ser Asn Gly Asn Thr Tyr Leu Tyr
1               5                   10                  15
```

<210> SEQ ID NO 168
<211> LENGTH: 7
<212> TYPE: PRT
<213> ORGANISM: Mus musculus

<400> SEQUENCE: 168

```
Arg Met Ser Asn Leu Ala Ser
1               5
```

<210> SEQ ID NO 169
<211> LENGTH: 9
<212> TYPE: PRT
<213> ORGANISM: Mus musculus

<400> SEQUENCE: 169

```
Met Gln His Arg Glu Tyr Pro Val Thr
1               5
```

<210> SEQ ID NO 170
<211> LENGTH: 5
<212> TYPE: PRT
<213> ORGANISM: Mus musculus

<400> SEQUENCE: 170

```
Ser Tyr Trp Ile Glu
1               5
```

<210> SEQ ID NO 171
<211> LENGTH: 17
<212> TYPE: PRT
<213> ORGANISM: Mus musculus

<400> SEQUENCE: 171

```
Glu Ile Leu Pro Gly Ser Gly Ser Thr Asn Tyr Asn Glu Lys Phe Lys
1               5                   10                  15

Gly
```

<210> SEQ ID NO 172
<211> LENGTH: 11
<212> TYPE: PRT
<213> ORGANISM: Mus musculus

<400> SEQUENCE: 172

```
Tyr Tyr Trp Tyr Phe Asp Val Trp Ala Gln Asp
1               5                   10
```

<210> SEQ ID NO 173
<211> LENGTH: 15
<212> TYPE: PRT
<213> ORGANISM: Mus musculus

<400> SEQUENCE: 173

Ser Ser Lys Asn Leu Leu His Ser Asn Gly Ile Thr Tyr Leu Tyr
1 5 10 15

<210> SEQ ID NO 174
<211> LENGTH: 7
<212> TYPE: PRT
<213> ORGANISM: Mus musculus

<400> SEQUENCE: 174

Arg Val Ser Asn Leu Ala Ser
1 5

<210> SEQ ID NO 175
<211> LENGTH: 9
<212> TYPE: PRT
<213> ORGANISM: Mus musculus

<400> SEQUENCE: 175

Ala Gln Leu Leu Glu Leu Pro Tyr Thr
1 5

<210> SEQ ID NO 176
<211> LENGTH: 5
<212> TYPE: PRT
<213> ORGANISM: Mus musculus

<400> SEQUENCE: 176

Ser Tyr Asp Met Ser
1 5

<210> SEQ ID NO 177
<211> LENGTH: 17
<212> TYPE: PRT
<213> ORGANISM: Mus musculus

<400> SEQUENCE: 177

Tyr Ile Ser Ser Gly Ala Gly Ser Thr Tyr Tyr Pro Asp Thr Val Lys
1 5 10 15

Gly

<210> SEQ ID NO 178
<211> LENGTH: 11
<212> TYPE: PRT
<213> ORGANISM: Mus musculus

<400> SEQUENCE: 178

His Phe Tyr Arg Phe Asp Tyr Trp Gly Gln Gly
1 5 10

<210> SEQ ID NO 179
<211> LENGTH: 15
<212> TYPE: PRT
<213> ORGANISM: Mus musculus

<400> SEQUENCE: 179

Ser Ala Gly Asp Arg Ile Thr Ile Thr Cys Lys Ala Ser Gln Ser
1 5 10 15

<210> SEQ ID NO 180
<211> LENGTH: 7
<212> TYPE: PRT
<213> ORGANISM: Mus musculus

<400> SEQUENCE: 180

Tyr Ala Ser Asn Arg Tyr Thr
1 5

<210> SEQ ID NO 181
<211> LENGTH: 9
<212> TYPE: PRT
<213> ORGANISM: Mus musculus

<400> SEQUENCE: 181

Gln Gln Asp Asp Arg Phe Pro Leu Thr
1 5

<210> SEQ ID NO 182
<211> LENGTH: 5
<212> TYPE: PRT
<213> ORGANISM: Mus musculus

<400> SEQUENCE: 182

Asn Tyr Gly Met Asn
1 5

<210> SEQ ID NO 183
<211> LENGTH: 17
<212> TYPE: PRT
<213> ORGANISM: Mus musculus

<400> SEQUENCE: 183

Trp Ile Asn Thr Tyr Thr Gly Glu Pro Thr Tyr Ala Asp Asp Phe Lys
1 5 10 15

Gly

<210> SEQ ID NO 184
<211> LENGTH: 11
<212> TYPE: PRT
<213> ORGANISM: Mus musculus

<400> SEQUENCE: 184

Gly Ala Trp Phe Ala Tyr Trp Ala Lys Asp Ser
1 5 10

<210> SEQ ID NO 185
<211> LENGTH: 15
<212> TYPE: PRT
<213> ORGANISM: Mus musculus

<400> SEQUENCE: 185

Ser Ile Thr Cys Lys Ala Ser Gln Asp Val Gly Thr Ala Val Ala
1 5 10 15

<210> SEQ ID NO 186
<211> LENGTH: 7
<212> TYPE: PRT
<213> ORGANISM: Mus musculus

<400> SEQUENCE: 186

Trp Ala Ser Thr Arg His Thr
1 5

<210> SEQ ID NO 187
<211> LENGTH: 9
<212> TYPE: PRT
<213> ORGANISM: Mus musculus

<400> SEQUENCE: 187

```
Gln Gln Tyr Ser Ser Tyr Pro Leu Thr
1               5
```

<210> SEQ ID NO 188
<211> LENGTH: 5
<212> TYPE: PRT
<213> ORGANISM: Mus musculus

<400> SEQUENCE: 188

```
Asp Phe Trp Met Asn
1               5
```

<210> SEQ ID NO 189
<211> LENGTH: 19
<212> TYPE: PRT
<213> ORGANISM: Mus musculus

<400> SEQUENCE: 189

```
Glu Ile Arg Leu Lys Ser Asn Asn Tyr Ala Thr His Tyr Ala Glu Ser
1               5                   10                  15

Val Lys Gly
```

<210> SEQ ID NO 190
<211> LENGTH: 13
<212> TYPE: PRT
<213> ORGANISM: Mus musculus

<400> SEQUENCE: 190

```
Leu Phe Tyr Tyr Tyr Asp Gly Thr Ser Gly Phe Ala Tyr
1               5                   10
```

<210> SEQ ID NO 191
<211> LENGTH: 17
<212> TYPE: PRT
<213> ORGANISM: Mus musculus

<400> SEQUENCE: 191

```
Lys Ser Ser Gln Ser Leu Leu Asn Ser Gly Asp Gln Lys Asn Tyr Leu
1               5                   10                  15

Thr
```

<210> SEQ ID NO 192
<211> LENGTH: 7
<212> TYPE: PRT
<213> ORGANISM: Mus musculus

<400> SEQUENCE: 192

```
Trp Ala Ser Thr Arg Glu Ser
1               5
```

<210> SEQ ID NO 193
<211> LENGTH: 9
<212> TYPE: PRT
<213> ORGANISM: Mus musculus

<400> SEQUENCE: 193

Gln Asn Asp Tyr Asp Tyr Pro Leu Thr
1 5

<210> SEQ ID NO 194
<211> LENGTH: 5
<212> TYPE: PRT
<213> ORGANISM: Mus musculus

<400> SEQUENCE: 194

Asp Tyr Asn Met Asp
1 5

<210> SEQ ID NO 195
<211> LENGTH: 17
<212> TYPE: PRT
<213> ORGANISM: Mus musculus

<400> SEQUENCE: 195

Asp Ile Asn Pro Asn Tyr Asp Ser Thr Ser Tyr Asn Gln Lys Phe Lys
1 5 10 15

Gly

<210> SEQ ID NO 196
<211> LENGTH: 11
<212> TYPE: PRT
<213> ORGANISM: Mus musculus

<400> SEQUENCE: 196

Ser Arg Ser Tyr Asp Tyr Glu Gly Phe Ala Tyr
1 5 10

<210> SEQ ID NO 197
<211> LENGTH: 11
<212> TYPE: PRT
<213> ORGANISM: Mus musculus

<400> SEQUENCE: 197

Arg Ala Ser Gly Asn Ile His Asn Tyr Leu Ala
1 5 10

<210> SEQ ID NO 198
<211> LENGTH: 7
<212> TYPE: PRT
<213> ORGANISM: Mus musculus

<400> SEQUENCE: 198

Asn Ala Lys Thr Leu Ala Asp
1 5

<210> SEQ ID NO 199
<211> LENGTH: 8
<212> TYPE: PRT
<213> ORGANISM: Mus musculus

<400> SEQUENCE: 199

Gln His Phe Trp Ser Thr Leu Thr
1 5

<210> SEQ ID NO 200
<211> LENGTH: 5
<212> TYPE: PRT
<213> ORGANISM: Mus musculus

<400> SEQUENCE: 200

Gly Tyr Thr Met Asn
1 5

<210> SEQ ID NO 201
<211> LENGTH: 16
<212> TYPE: PRT
<213> ORGANISM: Mus musculus

<400> SEQUENCE: 201

Asn Pro Tyr Asn Gly Gly Thr Ser Tyr Asn Gln Lys Phe Lys Gly Lys
1 5 10 15

<210> SEQ ID NO 202
<211> LENGTH: 9
<212> TYPE: PRT
<213> ORGANISM: Mus musculus

<400> SEQUENCE: 202

Trp Gly Val Trp Ser Ala Met Asp Tyr
1 5

<210> SEQ ID NO 203
<211> LENGTH: 11
<212> TYPE: PRT
<213> ORGANISM: Mus musculus

<400> SEQUENCE: 203

Lys Ala Ser Gln Asn Val Arg Thr Ala Val Ala
1 5 10

<210> SEQ ID NO 204
<211> LENGTH: 7
<212> TYPE: PRT
<213> ORGANISM: Mus musculus

<400> SEQUENCE: 204

Leu Ala Ser Asn Arg Asp Thr
1 5

<210> SEQ ID NO 205
<211> LENGTH: 9
<212> TYPE: PRT
<213> ORGANISM: Mus musculus

<400> SEQUENCE: 205

Leu Gln His Cys Asn Tyr Pro Asn Glu
1 5

<210> SEQ ID NO 206
<211> LENGTH: 5
<212> TYPE: PRT
<213> ORGANISM: Mus musculus

<400> SEQUENCE: 206

Ser Tyr Trp Met Gln
1 5

<210> SEQ ID NO 207
<211> LENGTH: 17
<212> TYPE: PRT
<213> ORGANISM: Mus musculus

<400> SEQUENCE: 207

Ala Ile Tyr Pro Gly Asp Gly Asp Thr Arg Tyr Thr Gln Lys Phe Lys
1 5 10 15

Gly

<210> SEQ ID NO 208
<211> LENGTH: 11
<212> TYPE: PRT
<213> ORGANISM: Mus musculus

<400> SEQUENCE: 208

Ala Arg Gly Glu Tyr Gly Asn Tyr Phe Ala Tyr
1               5                   10

<210> SEQ ID NO 209
<211> LENGTH: 11
<212> TYPE: PRT
<213> ORGANISM: Mus musculus

<400> SEQUENCE: 209

Lys Ala Ser Gln Asp Ile Asn Ser Tyr Leu Ser
1               5                   10

<210> SEQ ID NO 210
<211> LENGTH: 7
<212> TYPE: PRT
<213> ORGANISM: Mus musculus

<400> SEQUENCE: 210

Arg Ala Asn Arg Leu Val Asp
1               5

<210> SEQ ID NO 211
<211> LENGTH: 9
<212> TYPE: PRT
<213> ORGANISM: Mus musculus

<400> SEQUENCE: 211

Leu Gln Tyr Asp Glu Phe Pro Leu Thr
1               5

<210> SEQ ID NO 212
<211> LENGTH: 5
<212> TYPE: PRT
<213> ORGANISM: Mus musculus

<400> SEQUENCE: 212

Asp Thr Tyr Met His
1               5

<210> SEQ ID NO 213
<211> LENGTH: 17
<212> TYPE: PRT
<213> ORGANISM: Mus musculus

<400> SEQUENCE: 213

Arg Ile Asp Pro Ala Asn Gly Asn Thr Lys Tyr Asp Pro Lys Phe Gln
1               5                   10                  15

Gly

<210> SEQ ID NO 214
<211> LENGTH: 14
<212> TYPE: PRT
<213> ORGANISM: Mus musculus

<400> SEQUENCE: 214

```
Ala Arg Pro Ile His Tyr Tyr Tyr Gly Ser Ser Leu Ala Tyr
1               5                   10


<210> SEQ ID NO 215
<211> LENGTH: 11
<212> TYPE: PRT
<213> ORGANISM: Mus musculus

<400> SEQUENCE: 215

Ser Val Asp Ser Tyr Gly Asn Ser Phe Met His
1               5                   10


<210> SEQ ID NO 216
<211> LENGTH: 7
<212> TYPE: PRT
<213> ORGANISM: Mus musculus

<400> SEQUENCE: 216

Arg Ala Ser Asn Leu Glu Ser
1               5


<210> SEQ ID NO 217
<211> LENGTH: 9
<212> TYPE: PRT
<213> ORGANISM: Mus musculus

<400> SEQUENCE: 217

Gln Gln Ser Asn Glu Asp Pro Gly Arg
1               5


<210> SEQ ID NO 218
<211> LENGTH: 5
<212> TYPE: PRT
<213> ORGANISM: Mus musculus

<400> SEQUENCE: 218

Asp Tyr Tyr Met Ser
1               5


<210> SEQ ID NO 219
<211> LENGTH: 17
<212> TYPE: PRT
<213> ORGANISM: Mus musculus

<400> SEQUENCE: 219

Arg Asn Lys Ala Asn Gly Tyr Thr Thr Glu Tyr Ser Ala Ser Val Lys
1               5                   10                  15

Gly


<210> SEQ ID NO 220
<211> LENGTH: 9
<212> TYPE: PRT
<213> ORGANISM: Mus musculus

<400> SEQUENCE: 220

Ala Arg Ala Asn Trp Ala Phe Asp Tyr
1               5


<210> SEQ ID NO 221
<211> LENGTH: 11
<212> TYPE: PRT
<213> ORGANISM: Mus musculus

<400> SEQUENCE: 221
```

```
Arg Ala Ser Gln Ser Ile Ser Asn Tyr Leu His
1               5                   10


<210> SEQ ID NO 222
<211> LENGTH: 7
<212> TYPE: PRT
<213> ORGANISM: Mus musculus

<400> SEQUENCE: 222

Tyr Ala Ser Gln Ser Ile Ser
1               5


<210> SEQ ID NO 223
<211> LENGTH: 9
<212> TYPE: PRT
<213> ORGANISM: Mus musculus

<400> SEQUENCE: 223

Gln Gln Ser Asn Ser Trp Pro Tyr Thr
1               5


<210> SEQ ID NO 224
<211> LENGTH: 5
<212> TYPE: PRT
<213> ORGANISM: Mus musculus

<400> SEQUENCE: 224

Asp Tyr Tyr Met Ser
1               5


<210> SEQ ID NO 225
<211> LENGTH: 17
<212> TYPE: PRT
<213> ORGANISM: Mus musculus

<400> SEQUENCE: 225

Arg Asn Lys Ala Asn Gly Tyr Thr Thr Glu Tyr Ser Ala Ser Val Lys
1               5                   10                  15

Gly


<210> SEQ ID NO 226
<211> LENGTH: 12
<212> TYPE: PRT
<213> ORGANISM: Mus musculus

<400> SEQUENCE: 226

Ala Arg Ala Pro Leu Leu Tyr Tyr Ala Met Asp Tyr
1               5                   10


<210> SEQ ID NO 227
<211> LENGTH: 11
<212> TYPE: PRT
<213> ORGANISM: Mus musculus

<400> SEQUENCE: 227

Asn Val Ser Thr Ser Gly Tyr Ser Tyr Met His
1               5                   10


<210> SEQ ID NO 228
<211> LENGTH: 7
<212> TYPE: PRT
<213> ORGANISM: Mus musculus

<400> SEQUENCE: 228
```

Leu Val Ser Asn Leu Glu Ser
1               5

<210> SEQ ID NO 229
<211> LENGTH: 8
<212> TYPE: PRT
<213> ORGANISM: Mus musculus

<400> SEQUENCE: 229

Gln His Ile Arg Glu Leu Thr Arg
1               5

<210> SEQ ID NO 230
<211> LENGTH: 5
<212> TYPE: PRT
<213> ORGANISM: Mus musculus

<400> SEQUENCE: 230

Ser Tyr Trp Met His
1               5

<210> SEQ ID NO 231
<211> LENGTH: 17
<212> TYPE: PRT
<213> ORGANISM: Mus musculus

<400> SEQUENCE: 231

Met Ile Asp Pro Ser Asn Ser Glu Thr Arg Leu Asn Gln Lys Phe Lys
1               5                   10                  15

Asp

<210> SEQ ID NO 232
<211> LENGTH: 12
<212> TYPE: PRT
<213> ORGANISM: Mus musculus

<400> SEQUENCE: 232

Ala Arg Gly Leu Arg His Tyr Trp Tyr Phe Asp Val
1               5                   10

<210> SEQ ID NO 233
<211> LENGTH: 11
<212> TYPE: PRT
<213> ORGANISM: Mus musculus

<400> SEQUENCE: 233

Ser Val Ser Thr Ser Gly Tyr Ser Tyr Met His
1               5                   10

<210> SEQ ID NO 234
<211> LENGTH: 7
<212> TYPE: PRT
<213> ORGANISM: Mus musculus

<400> SEQUENCE: 234

Leu Val Ser Asn Leu Glu Ser
1               5

<210> SEQ ID NO 235
<211> LENGTH: 9
<212> TYPE: PRT
<213> ORGANISM: Mus musculus

<400> SEQUENCE: 235

Gln His Ile Arg Glu Leu Thr Arg Ser
1 5

<210> SEQ ID NO 236
<211> LENGTH: 5
<212> TYPE: PRT
<213> ORGANISM: Mus musculus

<400> SEQUENCE: 236

Ser Tyr Gly Met Ser
1 5

<210> SEQ ID NO 237
<211> LENGTH: 14
<212> TYPE: PRT
<213> ORGANISM: Mus musculus

<400> SEQUENCE: 237

Trp Val Arg Gln Thr Pro Glu Lys Arg Leu Glu Trp Val Ala
1 5 10

<210> SEQ ID NO 238
<211> LENGTH: 11
<212> TYPE: PRT
<213> ORGANISM: Mus musculus

<400> SEQUENCE: 238

Leu Ala Ser Tyr Tyr Phe Asp Tyr Trp Gly Gln
1 5 10

<210> SEQ ID NO 239
<211> LENGTH: 15
<212> TYPE: PRT
<213> ORGANISM: Mus musculus

<400> SEQUENCE: 239

Thr Met Thr Cys Gln Ala Ser Gln Gly Thr Ser Ile Asn Leu Asn
1 5 10 15

<210> SEQ ID NO 240
<211> LENGTH: 7
<212> TYPE: PRT
<213> ORGANISM: Mus musculus

<400> SEQUENCE: 240

Gly Ala Ser Ser Leu Glu Asp
1 5

<210> SEQ ID NO 241
<211> LENGTH: 11
<212> TYPE: PRT
<213> ORGANISM: Mus musculus

<400> SEQUENCE: 241

Leu Gln His Ser Tyr Leu Pro Pro Leu Thr Phe
1 5 10

<210> SEQ ID NO 242
<211> LENGTH: 5
<212> TYPE: PRT
<213> ORGANISM: Mus musculus

<400> SEQUENCE: 242

Thr Tyr Asp Leu His
1 5

<210> SEQ ID NO 243
<211> LENGTH: 16
<212> TYPE: PRT
<213> ORGANISM: Mus musculus

<400> SEQUENCE: 243

```
Val Ile Trp Ser Gly Gly Ser Thr Asp Tyr Asn Ala Ala Phe Ile Ser
1               5                   10                  15
```

<210> SEQ ID NO 244
<211> LENGTH: 11
<212> TYPE: PRT
<213> ORGANISM: Mus musculus

<400> SEQUENCE: 244

```
Asn Tyr Gly Tyr Ser Ala Trp Phe Ala Tyr Trp
1               5                   10
```

<210> SEQ ID NO 245
<211> LENGTH: 15
<212> TYPE: PRT
<213> ORGANISM: Mus musculus

<400> SEQUENCE: 245

```
Ala Ser Ile Ser Cys Arg Ser Ser Gln Ser Ile Val His Ser Asn
1               5                   10                  15
```

<210> SEQ ID NO 246
<211> LENGTH: 7
<212> TYPE: PRT
<213> ORGANISM: Mus musculus

<400> SEQUENCE: 246

```
Lys Val Ser Asn Arg Phe Ser
1               5
```

<210> SEQ ID NO 247
<211> LENGTH: 9
<212> TYPE: PRT
<213> ORGANISM: Mus musculus

<400> SEQUENCE: 247

```
Phe Gln Gly Ser His Val Pro Leu Thr
1               5
```

<210> SEQ ID NO 248
<211> LENGTH: 5
<212> TYPE: PRT
<213> ORGANISM: Mus musculus

<400> SEQUENCE: 248

```
Ala Tyr Ser Met His
1               5
```

<210> SEQ ID NO 249
<211> LENGTH: 17
<212> TYPE: PRT
<213> ORGANISM: Mus musculus

<400> SEQUENCE: 249

```
Trp Ile Asn Thr Glu Thr Gly Glu Pro Thr Tyr Thr Asp Asp Phe Lys
1               5                   10                  15

Gly
```

<210> SEQ ID NO 250
<211> LENGTH: 11
<212> TYPE: PRT
<213> ORGANISM: Mus musculus

<400> SEQUENCE: 250

Arg Ile Tyr Tyr Phe Gly Arg Gly Gly Phe Asp
1 5 10

<210> SEQ ID NO 251
<211> LENGTH: 15
<212> TYPE: PRT
<213> ORGANISM: Mus musculus

<400> SEQUENCE: 251

Ser Ser Ile Ser Cys Arg Ser Ser Gln Ser Ile Val His Ser Asn
1 5 10 15

<210> SEQ ID NO 252
<211> LENGTH: 7
<212> TYPE: PRT
<213> ORGANISM: Mus musculus

<400> SEQUENCE: 252

Lys Val Ser Asn Arg Phe Ser
1 5

<210> SEQ ID NO 253
<211> LENGTH: 9
<212> TYPE: PRT
<213> ORGANISM: Mus musculus

<400> SEQUENCE: 253

Phe Gln Gly Ser His Val Pro Tyr Thr
1 5

<210> SEQ ID NO 254
<211> LENGTH: 5
<212> TYPE: PRT
<213> ORGANISM: Mus musculus

<400> SEQUENCE: 254

Asn Ser Trp Phe Asn
1 5

<210> SEQ ID NO 255
<211> LENGTH: 19
<212> TYPE: PRT
<213> ORGANISM: Mus musculus

<400> SEQUENCE: 255

Glu Ile Arg Leu Thr Ser Asp Asn Tyr Ala Ile Tyr Tyr Ala Glu Ser
1 5 10 15

Val Lys Gly

<210> SEQ ID NO 256
<211> LENGTH: 11
<212> TYPE: PRT
<213> ORGANISM: Mus musculus

<400> SEQUENCE: 256

Pro Glu Thr Ala Arg Ala Thr Phe Ala Tyr Trp
1 5 10

```
<210> SEQ ID NO 257
<211> LENGTH: 15
<212> TYPE: PRT
<213> ORGANISM: Mus musculus

<400> SEQUENCE: 257

Ala Ser Ile Ser Cys Arg Ser Ser Gln Ser Ile Val His Ser Asn
1               5                   10                  15


<210> SEQ ID NO 258
<211> LENGTH: 7
<212> TYPE: PRT
<213> ORGANISM: Mus musculus

<400> SEQUENCE: 258

Lys Val Phe Asn Arg Phe Ser
1               5


<210> SEQ ID NO 259
<211> LENGTH: 9
<212> TYPE: PRT
<213> ORGANISM: Mus musculus

<400> SEQUENCE: 259

Phe Gln Gly Ser His Val Pro Arg Thr
1               5


<210> SEQ ID NO 260
<211> LENGTH: 5
<212> TYPE: PRT
<213> ORGANISM: Mus musculus

<400> SEQUENCE: 260

Ala Tyr Tyr Met His
1               5


<210> SEQ ID NO 261
<211> LENGTH: 17
<212> TYPE: PRT
<213> ORGANISM: Mus musculus

<400> SEQUENCE: 261

Arg Val Asn Pro Asn Asn Gly Gly Thr Thr Tyr Asn Gln Lys Phe Lys
1               5                   10                  15

Gly


<210> SEQ ID NO 262
<211> LENGTH: 11
<212> TYPE: PRT
<213> ORGANISM: Mus musculus

<400> SEQUENCE: 262

Arg Ile Tyr Tyr Gly Tyr Phe Asp Tyr Trp Gly
1               5                   10


<210> SEQ ID NO 263
<211> LENGTH: 15
<212> TYPE: PRT
<213> ORGANISM: Mus musculus

<400> SEQUENCE: 263

Lys Ala Ser Gln Ser Val Asp Tyr Asp Gly Asp Ser Tyr Met Asn
1               5                   10                  15
```

<210> SEQ ID NO 264
<211> LENGTH: 7
<212> TYPE: PRT
<213> ORGANISM: Mus musculus

<400> SEQUENCE: 264

Val Ala Ser Asn Leu Glu Ser
1 5

<210> SEQ ID NO 265
<211> LENGTH: 9
<212> TYPE: PRT
<213> ORGANISM: Mus musculus

<400> SEQUENCE: 265

Gln Gln Ser Asn Glu Asp Pro Tyr Thr
1 5

<210> SEQ ID NO 266
<211> LENGTH: 4
<212> TYPE: PRT
<213> ORGANISM: Mus musculus

<400> SEQUENCE: 266

Asp Ile Tyr Met
1

<210> SEQ ID NO 267
<211> LENGTH: 17
<212> TYPE: PRT
<213> ORGANISM: Mus musculus

<400> SEQUENCE: 267

Lys Ile Asp Pro Ala Asn Gly Asn Thr Lys Tyr Asp Pro Lys Phe Gln
1 5 10 15

Gly

<210> SEQ ID NO 268
<211> LENGTH: 11
<212> TYPE: PRT
<213> ORGANISM: Mus musculus

<400> SEQUENCE: 268

Thr Gly Asp Tyr Trp Gly Gln Gly Thr Thr Val
1 5 10

<210> SEQ ID NO 269
<211> LENGTH: 15
<212> TYPE: PRT
<213> ORGANISM: Mus musculus

<400> SEQUENCE: 269

Thr Met Ser Cys Lys Ser Ser Gln Ser Leu Leu Asn Ser Arg Thr
1 5 10 15

<210> SEQ ID NO 270
<211> LENGTH: 7
<212> TYPE: PRT
<213> ORGANISM: Mus musculus

<400> SEQUENCE: 270

Trp Ala Ser Thr Arg Glu Ser
1 5

<210> SEQ ID NO 271
<211> LENGTH: 9
<212> TYPE: PRT
<213> ORGANISM: Mus musculus

<400> SEQUENCE: 271

Arg Gln Ser Tyr Asn Leu Val Thr Phe
1               5

<210> SEQ ID NO 272
<211> LENGTH: 5
<212> TYPE: PRT
<213> ORGANISM: Mus musculus

<400> SEQUENCE: 272

Ser Tyr Val Met His
1               5

<210> SEQ ID NO 273
<211> LENGTH: 17
<212> TYPE: PRT
<213> ORGANISM: Mus musculus

<400> SEQUENCE: 273

Tyr Ile Asn Pro Tyr Asn Asp Gly Thr Lys Tyr Asn Glu Lys Phe Lys
1               5                   10                  15

Gly

<210> SEQ ID NO 274
<211> LENGTH: 11
<212> TYPE: PRT
<213> ORGANISM: Mus musculus

<400> SEQUENCE: 274

Arg Tyr Tyr Tyr Gly Ser Ser Gly Gly Tyr Phe
1               5                   10

<210> SEQ ID NO 275
<211> LENGTH: 15
<212> TYPE: PRT
<213> ORGANISM: Mus musculus

<400> SEQUENCE: 275

Arg Ala Ser Lys Ser Ile Ser Lys Tyr Leu Ala Trp Tyr Gln Glu
1               5                   10                  15

<210> SEQ ID NO 276
<211> LENGTH: 7
<212> TYPE: PRT
<213> ORGANISM: Mus musculus

<400> SEQUENCE: 276

Ser Gly Ser Thr Leu Gln Ser
1               5

<210> SEQ ID NO 277
<211> LENGTH: 9
<212> TYPE: PRT
<213> ORGANISM: Mus musculus

<400> SEQUENCE: 277

Gln Gln His Asn Glu Tyr Pro Tyr Thr
1               5

<210> SEQ ID NO 278
<211> LENGTH: 5
<212> TYPE: PRT
<213> ORGANISM: Mus musculus

<400> SEQUENCE: 278

Gly Tyr Phe Met Asn
1               5

<210> SEQ ID NO 279
<211> LENGTH: 17
<212> TYPE: PRT
<213> ORGANISM: Mus musculus

<400> SEQUENCE: 279

Arg Ile Asn Pro Tyr Asn Gly Asp Thr Phe Tyr Asn Gln Lys Phe Lys
1               5                   10                  15

Gly

<210> SEQ ID NO 280
<211> LENGTH: 11
<212> TYPE: PRT
<213> ORGANISM: Mus musculus

<400> SEQUENCE: 280

Arg Ile His Tyr Tyr Tyr Gly Ser Ser Tyr Tyr
1               5                   10

<210> SEQ ID NO 281
<211> LENGTH: 15
<212> TYPE: PRT
<213> ORGANISM: Mus musculus

<400> SEQUENCE: 281

Arg Ala Ser Lys Ser Ile Ser Lys Tyr Leu Ala Trp Tyr Gln Glu
1               5                   10                  15

<210> SEQ ID NO 282
<211> LENGTH: 7
<212> TYPE: PRT
<213> ORGANISM: Mus musculus

<400> SEQUENCE: 282

Ser Gly Ser Thr Leu Gln Ser
1               5

<210> SEQ ID NO 283
<211> LENGTH: 9
<212> TYPE: PRT
<213> ORGANISM: Mus musculus

<400> SEQUENCE: 283

Gln Gln His Asn Glu Tyr Pro Trp Thr
1               5

<210> SEQ ID NO 284
<211> LENGTH: 5
<212> TYPE: PRT
<213> ORGANISM: Mus musculus

<400> SEQUENCE: 284

Glu Tyr Ile Ile His
1               5

<210> SEQ ID NO 285
<211> LENGTH: 17
<212> TYPE: PRT
<213> ORGANISM: Mus musculus

<400> SEQUENCE: 285

Trp Phe Tyr Pro Gly Ser Gly Ser Ile Lys Tyr Asn Glu Lys Phe Lys
1               5                   10                  15

Asp

<210> SEQ ID NO 286
<211> LENGTH: 11
<212> TYPE: PRT
<213> ORGANISM: Mus musculus

<400> SEQUENCE: 286

His Glu Val Tyr Tyr Asp Tyr Asp Lys Ser Met
1               5                   10

<210> SEQ ID NO 287
<211> LENGTH: 15
<212> TYPE: PRT
<213> ORGANISM: Mus musculus

<400> SEQUENCE: 287

Leu Tyr Ser Ser Asn Gln Lys Asn Tyr Leu Ala Trp Tyr Gln Gln
1               5                   10                  15

<210> SEQ ID NO 288
<211> LENGTH: 7
<212> TYPE: PRT
<213> ORGANISM: Mus musculus

<400> SEQUENCE: 288

Trp Ala Ser Thr Arg Glu Ser
1               5

<210> SEQ ID NO 289
<211> LENGTH: 9
<212> TYPE: PRT
<213> ORGANISM: Mus musculus

<400> SEQUENCE: 289

Gln Gln Tyr Tyr Ser Tyr Pro Tyr Thr
1               5

<210> SEQ ID NO 290
<211> LENGTH: 5
<212> TYPE: PRT
<213> ORGANISM: Mus musculus

<400> SEQUENCE: 290

Asn Tyr Leu Ile Glu
1               5

<210> SEQ ID NO 291
<211> LENGTH: 19
<212> TYPE: PRT
<213> ORGANISM: Mus musculus

<400> SEQUENCE: 291

Val Ile Asn Pro Lys Ser Gly Gly Thr Lys Tyr Asn Glu Lys Phe Arg
1               5                   10                  15

Gly Lys Ala

<210> SEQ ID NO 292
<211> LENGTH: 11
<212> TYPE: PRT
<213> ORGANISM: Mus musculus

<400> SEQUENCE: 292

Thr Gly Thr Asp Tyr Trp Gly Gln Gly Thr Thr
1 5 10

<210> SEQ ID NO 293
<211> LENGTH: 10
<212> TYPE: PRT
<213> ORGANISM: Mus musculus

<400> SEQUENCE: 293

Val Thr Ile Ser Cys Ser Ala Ser Gln Gly
1 5 10

<210> SEQ ID NO 294
<211> LENGTH: 7
<212> TYPE: PRT
<213> ORGANISM: Mus musculus

<400> SEQUENCE: 294

Tyr Thr Ser Ser Leu Arg Ser
1 5

<210> SEQ ID NO 295
<211> LENGTH: 9
<212> TYPE: PRT
<213> ORGANISM: Mus musculus

<400> SEQUENCE: 295

Gln Gln Tyr Ser Lys Leu Pro Arg Thr
1 5

<210> SEQ ID NO 296
<211> LENGTH: 12
<212> TYPE: PRT
<213> ORGANISM: Homo sapiens

<400> SEQUENCE: 296

Phe Thr Ser Gly Glu Lys Glu Gln Val Asp Glu Trp
1 5 10

<210> SEQ ID NO 297
<211> LENGTH: 16
<212> TYPE: PRT
<213> ORGANISM: Homo sapiens

<400> SEQUENCE: 297

Ala Glu Gln Lys Arg Leu Lys Thr Val Leu Glu Leu Gln Tyr Val Leu
1 5 10 15

<210> SEQ ID NO 298
<211> LENGTH: 16
<212> TYPE: PRT
<213> ORGANISM: Homo sapiens

<400> SEQUENCE: 298

Val Glu Arg Val Phe Gln Ser Asn Tyr Phe Asp Ser Thr His Asn His
1 5 10 15

<210> SEQ ID NO 299
<211> LENGTH: 16
<212> TYPE: PRT
<213> ORGANISM: Homo sapiens

<400> SEQUENCE: 299

```
Phe Gln Ser Met Gln Thr Val Phe Asn Met Asn Ala Pro Val Pro Pro
1               5                   10                  15
```

<210> SEQ ID NO 300
<211> LENGTH: 5
<212> TYPE: PRT
<213> ORGANISM: Mus musculus

<400> SEQUENCE: 300

```
Thr Asn Ala Met Asn
1               5
```

<210> SEQ ID NO 301
<211> LENGTH: 17
<212> TYPE: PRT
<213> ORGANISM: Mus musculus

<400> SEQUENCE: 301

```
Arg Ile Arg Ser Lys Ser Asn Asn Tyr Ala Thr Tyr Tyr Ala Asp Ser
1               5                   10                  15

Val
```

<210> SEQ ID NO 302
<211> LENGTH: 11
<212> TYPE: PRT
<213> ORGANISM: Mus musculus

<400> SEQUENCE: 302

```
Asp Trp Asp Gly Phe Leu Tyr Phe Asp Tyr Trp
1               5                   10
```

<210> SEQ ID NO 303
<211> LENGTH: 112
<212> TYPE: PRT
<213> ORGANISM: Mus musculus

<400> SEQUENCE: 303

```
Gly Gly Gly Leu Val Gln Pro Lys Gly Ser Leu Lys Leu Ser Cys Ala
1               5                   10                  15

Ala Ser Gly Phe Thr Phe Asn Thr Asn Ala Met Asn Trp Val Arg Gln
            20                  25                  30

Ala Pro Gly Lys Gly Leu Glu Trp Val Ala Arg Ile Arg Ser Lys Ser
        35                  40                  45

Asn Asn Tyr Ala Thr Tyr Tyr Ala Asp Ser Val Lys Asp Arg Phe Thr
    50                  55                  60

Ile Ser Arg Asp Asp Ser Gln Ser Met Leu Tyr Leu Gln Met Asn Asn
65                  70                  75                  80

Leu Lys Thr Glu Asp Thr Ala Met Tyr Tyr Cys Val Arg Asp Trp Asp
                85                  90                  95

Gly Phe Leu Tyr Phe Asp Tyr Trp Ala Lys His His Leu Thr Leu Phe
            100                 105                 110
```

<210> SEQ ID NO 304
<211> LENGTH: 15

<212> TYPE: PRT
<213> ORGANISM: Mus musculus

<400> SEQUENCE: 304

```
Ser Val Ser Thr Ser Gly Tyr Ser Tyr Met His Trp Asn Gln Gln
1               5                   10                  15
```

<210> SEQ ID NO 305
<211> LENGTH: 7
<212> TYPE: PRT
<213> ORGANISM: Mus musculus

<400> SEQUENCE: 305

```
Leu Val Ser Asn Leu Glu Ser
1               5
```

<210> SEQ ID NO 306
<211> LENGTH: 9
<212> TYPE: PRT
<213> ORGANISM: Mus musculus

<400> SEQUENCE: 306

```
Gln His Ile Arg Glu Leu Thr Arg Ser
1               5
```

<210> SEQ ID NO 307
<211> LENGTH: 104
<212> TYPE: PRT
<213> ORGANISM: Mus musculus

<400> SEQUENCE: 307

```
Thr Gln Ser Pro Ala Ser Leu Ala Val Ser Leu Gly Gln Arg Ala Thr
1               5                   10                  15

Ile Ser Tyr Arg Ala Ser Lys Ser Val Ser Thr Ser Gly Tyr Ser Tyr
            20                  25                  30

Met His Trp Asn Gln Gln Lys Pro Gly Gln Pro Pro Arg Leu Leu Ile
        35                  40                  45

Tyr Leu Val Ser Asn Leu Glu Ser Gly Val Pro Ala Arg Phe Ser Gly
    50                  55                  60

Ser Gly Ser Gly Thr Asp Phe Thr Leu Asn Ile His Pro Val Glu Glu
65                  70                  75                  80

Glu Asp Ala Ala Thr Tyr Tyr Cys Gln His Ile Arg Glu Leu Thr Arg
                85                  90                  95

Ser Glu Gly Gly Pro Ser Trp Lys
            100
```

<210> SEQ ID NO 308
<211> LENGTH: 14
<212> TYPE: PRT

```
<213> ORGANISM: Homo sapiens

<400> SEQUENCE: 308

Pro Pro Val Asn Glu Pro Glu Thr Leu Lys Gln Gln Asn Gln
1               5                   10


<210> SEQ ID NO 309
<211> LENGTH: 12
<212> TYPE: PRT
<213> ORGANISM: Homo sapiens

<400> SEQUENCE: 309

Glu Thr Leu Lys Gln Gln Asn Gln Tyr Gln Ala Ser
1               5                   10
```